United States Patent
Graetzel et al.

(10) Patent No.: US 12,029,390 B2
(45) Date of Patent: *Jul. 9, 2024

(54) SYSTEM AND METHOD FOR DRIVING MEDICAL INSTRUMENT

(71) Applicant: Auris Health, Inc., Redwood City, CA (US)

(72) Inventors: Chauncey F. Graetzel, Palo Alto, CA (US); Alexander James Sheehy, Redwood City, CA (US)

(73) Assignee: Auris Health, Inc., Redwood City, CA (US)

( * ) Notice: Subject to any disclaimer, the term of this patent is extended or adjusted under 35 U.S.C. 154(b) by 938 days.

This patent is subject to a terminal disclaimer.

(21) Appl. No.: 16/943,180

(22) Filed: Jul. 30, 2020

(65) Prior Publication Data

US 2020/0352420 A1    Nov. 12, 2020

Related U.S. Application Data

(63) Continuation of application No. 16/273,985, filed on Feb. 12, 2019, now Pat. No. 10,765,303.

(Continued)

(51) Int. Cl.
*A61B 34/00* (2016.01)
*A61B 1/00* (2006.01)
(Continued)

(52) U.S. Cl.
CPC ...... *A61B 1/00149* (2013.01); *A61B 1/00006* (2013.01); *A61B 1/0002* (2013.01);
(Continued)

(58) Field of Classification Search
CPC ..... A61B 19/2203; A61B 34/25; A61B 34/30; A61B 34/74; A61B 46/10; A61B 90/37;
(Continued)

(56) References Cited

U.S. PATENT DOCUMENTS

| | | |
|---|---|---|
| 4,644,237 A | 2/1987 | Frushour et al. |
| 4,745,908 A | 5/1988 | Wardle |

(Continued)

FOREIGN PATENT DOCUMENTS

| | | |
|---|---|---|
| CN | 1511249 | 7/2004 |
| CN | 1846181 | 10/2006 |

(Continued)

OTHER PUBLICATIONS

Final Rejection for U.S. Appl. No. 16/273,985, dated Feb. 10, 2020, 10 pages.

(Continued)

*Primary Examiner* — Mallika D Fairchild
*Assistant Examiner* — Thien Jason Tran
(74) *Attorney, Agent, or Firm* — Chang & Hale LLP

(57) ABSTRACT

Certain aspects relate to systems and techniques for driving a medical instrument having an inner body and an outer body. In one aspect, a system includes a medical instrument comprising an outer body and an inner body configured to be driven through a lumen in the outer body. The system may further include a set of one or more instrument manipulators configured to control movement of the outer and inner bodies and a set of one or more processors configured to: receive a change drive mode command, and in response to receiving the change drive mode command, change a drive mode of the medical instrument from a paired drive mode to an unpaired drive mode.

30 Claims, 33 Drawing Sheets

Related U.S. Application Data

(60) Provisional application No. 62/630,112, filed on Feb. 13, 2018.

(51) Int. Cl.
*A61B 1/005* (2006.01)
*A61B 1/267* (2006.01)
*A61B 1/273* (2006.01)
*A61B 1/307* (2006.01)
*A61B 34/30* (2016.01)
*A61B 90/00* (2016.01)

(52) U.S. Cl.
CPC .......... *A61B 1/0016* (2013.01); *A61B 1/0057* (2013.01); *A61B 1/2676* (2013.01); *A61B 1/2736* (2013.01); *A61B 1/307* (2013.01); *A61B 34/71* (2016.02); *A61B 34/74* (2016.02); *A61B 2034/301* (2016.02); *A61B 2034/303* (2016.02); *A61B 2090/064* (2016.02)

(58) Field of Classification Search
CPC ... A61B 90/40; A61B 19/56; A61B 2090/064; A61B 2090/0813; A61B 2017/00199; A61B 2017/00221; A61B 2017/00902; A61B 2017/22065; A61B 2019/2223
See application file for complete search history.

(56) References Cited

U.S. PATENT DOCUMENTS

| | | |
|---|---|---|
| 4,748,969 A | 6/1988 | Wardle |
| 5,194,791 A | 3/1993 | Cull |
| 5,251,611 A | 10/1993 | Zehel et al. |
| 5,280,781 A | 1/1994 | Oku |
| 5,337,733 A | 8/1994 | Bauerfeind et al. |
| 5,408,263 A | 4/1995 | Kikuchi |
| 5,672,877 A | 9/1997 | Liebig et al. |
| 5,759,151 A | 6/1998 | Sturges |
| 5,769,086 A | 6/1998 | Ritchart |
| 5,899,851 A | 5/1999 | Koninckx |
| 6,004,016 A | 12/1999 | Spector |
| 6,179,776 B1 | 1/2001 | Adams et al. |
| 6,198,974 B1 | 3/2001 | Webster, Jr. |
| 6,246,200 B1 | 6/2001 | Blumenkranz et al. |
| 6,459,926 B1 | 10/2002 | Nowlin |
| 6,690,963 B2 | 2/2004 | Ben-Haim |
| 6,800,056 B2 | 10/2004 | Tartaglia et al. |
| 6,837,846 B2 | 1/2005 | Jaffe |
| 7,197,354 B2 | 3/2007 | Sobe |
| 7,607,440 B2 | 10/2009 | Coste-Maniere et al. |
| 7,763,015 B2 | 7/2010 | Cooper et al. |
| 7,772,541 B2 | 8/2010 | Froggatt et al. |
| 7,963,288 B2 | 6/2011 | Rosenberg et al. |
| 8,335,557 B2 | 12/2012 | Maschke |
| 8,348,931 B2 | 1/2013 | Cooper et al. |
| 8,376,934 B2 | 2/2013 | Takahashi |
| 8,396,595 B2 | 3/2013 | Dariush |
| 8,442,618 B2 | 5/2013 | Strommer et al. |
| 8,469,945 B2 | 6/2013 | Schena |
| 8,498,691 B2 | 7/2013 | Moll et al. |
| 8,506,555 B2 | 8/2013 | Ruiz Morales |
| 8,554,368 B2 | 10/2013 | Fielding et al. |
| 8,720,448 B2 | 5/2014 | Reis et al. |
| 8,738,181 B2 | 5/2014 | Greer et al. |
| 8,827,948 B2 | 9/2014 | Romo et al. |
| 8,894,610 B2 | 11/2014 | MacNamara et al. |
| 8,929,631 B2 | 1/2015 | Pfister et al. |
| 8,945,095 B2 | 2/2015 | Blumenkranz |
| 9,014,851 B2 | 4/2015 | Wong et al. |
| 9,023,060 B2 | 5/2015 | Cooper et al. |
| 9,129,417 B2 | 9/2015 | Zheng et al. |
| 9,173,713 B2 | 11/2015 | Hart et al. |
| 9,199,372 B2 | 12/2015 | Henderson et al. |
| 9,226,796 B2 | 1/2016 | Bowling |
| 9,256,940 B2 | 2/2016 | Carelsen et al. |
| 9,289,578 B2 | 3/2016 | Walker et al. |
| 9,302,702 B1 | 4/2016 | Schepmann |
| 9,314,306 B2 | 4/2016 | Yu |
| 9,345,456 B2 | 5/2016 | Tsonton et al. |
| 9,358,682 B2 | 6/2016 | Ruiz Morales |
| 9,452,276 B2 | 9/2016 | Duindam et al. |
| 9,504,604 B2 | 11/2016 | Alvarez |
| 9,522,034 B2 | 12/2016 | Johnson |
| 9,561,083 B2 | 2/2017 | Yu et al. |
| 9,622,827 B2 | 4/2017 | Yu et al. |
| 9,629,595 B2 | 4/2017 | Walker et al. |
| 9,636,184 B2 | 5/2017 | Lee et al. |
| 9,675,422 B2 | 6/2017 | Hourtash et al. |
| 9,713,509 B2 | 7/2017 | Schuh et al. |
| 9,717,563 B2 | 8/2017 | Tognaccini |
| 9,726,476 B2 | 8/2017 | Ramamurthy et al. |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,789,608 B2 | 10/2017 | Itkowitz et al. |
| 9,844,353 B2 | 12/2017 | Walker et al. |
| 9,844,412 B2 | 12/2017 | Bogusky et al. |
| 9,867,635 B2 | 1/2018 | Alvarez et al. |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 10,016,900 B1 | 7/2018 | Meyer et al. |
| 10,022,192 B1 | 7/2018 | Ummalaneni |
| 10,046,140 B2 | 8/2018 | Kokish et al. |
| 10,080,576 B2 | 9/2018 | Romo et al. |
| 10,136,959 B2 | 11/2018 | Mintz et al. |
| 10,143,526 B2 | 12/2018 | Walker et al. |
| 10,145,747 B1 | 12/2018 | Lin et al. |
| 10,149,720 B2 | 12/2018 | Romo |
| 10,159,532 B1 | 12/2018 | Ummalaneni et al. |
| 10,159,533 B2 | 12/2018 | Moll et al. |
| 10,169,875 B2 | 1/2019 | Mintz et al. |
| 10,213,264 B2 | 2/2019 | Tanner et al. |
| 10,219,874 B2 | 3/2019 | Yu et al. |
| 10,231,793 B2 | 3/2019 | Romo |
| 10,231,867 B2 | 3/2019 | Alvarez et al. |
| 10,244,926 B2 | 4/2019 | Noonan et al. |
| 10,285,574 B2 | 5/2019 | Landey et al. |
| 10,299,870 B2 | 5/2019 | Connolly et al. |
| 10,314,463 B2 | 6/2019 | Agrawal et al. |
| 10,383,765 B2 | 8/2019 | Alvarez et al. |
| 10,398,518 B2 | 9/2019 | Yu et al. |
| 10,405,939 B2 | 9/2019 | Romo et al. |
| 10,405,940 B2 | 9/2019 | Romo |
| 10,426,559 B2 | 10/2019 | Graetzel et al. |
| 10,426,661 B2 | 10/2019 | Kintz |
| 10,434,660 B2 | 10/2019 | Meyer |
| 10,454,347 B2 | 10/2019 | Covington et al. |
| 10,464,209 B2 | 11/2019 | Ho et al. |
| 10,470,830 B2 | 11/2019 | Hill |
| 10,482,599 B2 | 11/2019 | Mintz et al. |
| 10,493,241 B2 | 12/2019 | Jiang |
| 10,500,001 B2 | 12/2019 | Yu et al. |
| 10,517,692 B2 | 12/2019 | Eyre et al. |
| 10,524,866 B2 | 1/2020 | Srinivasan |
| 10,539,478 B2 | 1/2020 | Lin |
| 10,543,048 B2 | 1/2020 | Noonan et al. |
| 10,555,778 B2 | 2/2020 | Ummalaneni et al. |
| 10,583,271 B2 | 3/2020 | Bogusky |
| 10,631,949 B2 | 4/2020 | Schuh et al. |
| 10,639,108 B2 | 5/2020 | Romo et al. |
| 10,639,109 B2 | 5/2020 | Bovay et al. |
| 10,639,114 B2 | 5/2020 | Schuh |
| 10,667,871 B2 | 6/2020 | Romo et al. |
| 10,667,875 B2 | 6/2020 | DeFonzo |
| 10,682,189 B2 | 6/2020 | Schuh et al. |

(56) References Cited

U.S. PATENT DOCUMENTS

| | | |
|---|---|---|
| 10,702,348 B2 | 7/2020 | Moll et al. |
| 10,716,461 B2 | 7/2020 | Jenkins |
| 10,743,751 B2 | 8/2020 | Landey et al. |
| 10,744,035 B2 | 8/2020 | Alvarez et al. |
| 10,751,140 B2 | 8/2020 | Wallace et al. |
| 11,135,023 B2 | 10/2021 | Larkin et al. |
| 2001/0000040 A1 | 3/2001 | Adams et al. |
| 2001/0021843 A1 | 9/2001 | Bosselmann et al. |
| 2002/0035330 A1 | 3/2002 | Cline |
| 2002/0077533 A1 | 6/2002 | Bieger et al. |
| 2002/0161280 A1 | 10/2002 | Chatenever et al. |
| 2002/0173878 A1 | 11/2002 | Watanabe |
| 2003/0045778 A1 | 3/2003 | Ohline |
| 2003/0181809 A1 | 9/2003 | Hall et al. |
| 2003/0182091 A1 | 9/2003 | Kukuk |
| 2004/0072066 A1 | 4/2004 | Cho et al. |
| 2004/0257021 A1 | 12/2004 | Chang et al. |
| 2005/0043718 A1 | 2/2005 | Madhani |
| 2005/0065400 A1 | 3/2005 | Banik |
| 2005/0107917 A1 | 5/2005 | Smith et al. |
| 2005/0222554 A1 | 10/2005 | Wallace et al. |
| 2005/0234293 A1 | 10/2005 | Yamamoto |
| 2005/0256398 A1 | 11/2005 | Hastings |
| 2005/0261551 A1 | 11/2005 | Couvillon |
| 2005/0272975 A1 | 12/2005 | McWeeney et al. |
| 2006/0015096 A1 | 1/2006 | Hauck et al. |
| 2006/0041293 A1 | 2/2006 | Mehdizadeh |
| 2006/0079745 A1 | 4/2006 | Viswanathan |
| 2006/0200026 A1 | 9/2006 | Wallace et al. |
| 2006/0200049 A1 | 9/2006 | Leo et al. |
| 2006/0258938 A1 | 11/2006 | Hoffman et al. |
| 2006/0287769 A1 | 12/2006 | Yanagita et al. |
| 2007/0013336 A1 | 1/2007 | Nowlin et al. |
| 2007/0043455 A1 | 2/2007 | Viswanathan |
| 2007/0135886 A1 | 6/2007 | Maschke |
| 2007/0142971 A1 | 6/2007 | Schena |
| 2007/0150155 A1 | 6/2007 | Kawai |
| 2007/0249911 A1 | 10/2007 | Simon |
| 2007/0253599 A1 | 11/2007 | White et al. |
| 2007/0287992 A1 | 12/2007 | Diolaiti |
| 2007/0299353 A1 | 12/2007 | Harlev et al. |
| 2008/0027313 A1 | 1/2008 | Shachar |
| 2008/0046122 A1 | 2/2008 | Manzo et al. |
| 2008/0108870 A1 | 5/2008 | Wiita et al. |
| 2008/0123921 A1 | 5/2008 | Gielen et al. |
| 2008/0140087 A1 | 6/2008 | Barbagli et al. |
| 2008/0147089 A1 | 6/2008 | Loh |
| 2008/0159653 A1 | 7/2008 | Dunki-Jacobs et al. |
| 2008/0231221 A1 | 9/2008 | Ogawa |
| 2008/0249640 A1 | 10/2008 | Vittor et al. |
| 2008/0255505 A1 | 10/2008 | Carlson et al. |
| 2008/0312771 A1 | 12/2008 | Sugiura |
| 2009/0005768 A1 | 1/2009 | Sharareh |
| 2009/0062813 A1 | 3/2009 | Prisco |
| 2009/0076534 A1 | 3/2009 | Shelton |
| 2009/0184825 A1 | 7/2009 | Anderson |
| 2009/0198298 A1 | 8/2009 | Kaiser et al. |
| 2009/0245600 A1 | 10/2009 | Hoffman |
| 2009/0256905 A1 | 10/2009 | Tashiro |
| 2009/0287354 A1 | 11/2009 | Choi |
| 2009/0324161 A1 | 12/2009 | Prisco |
| 2010/0030061 A1 | 2/2010 | Canfield |
| 2010/0030115 A1 | 2/2010 | Fujimoto |
| 2010/0069920 A1 | 3/2010 | Naylor et al. |
| 2010/0076263 A1 | 3/2010 | Tanaka |
| 2010/0121138 A1 | 5/2010 | Goldenberg et al. |
| 2010/0168918 A1 | 7/2010 | Zhao |
| 2010/0204713 A1 | 8/2010 | Ruiz |
| 2010/0228266 A1 | 9/2010 | Hourtash |
| 2010/0234856 A1 | 9/2010 | Stoianovici et al. |
| 2010/0256812 A1 | 10/2010 | Tsusaka et al. |
| 2011/0009880 A1 | 1/2011 | Prisco |
| 2011/0021926 A1 | 1/2011 | Spencer |
| 2011/0082366 A1 | 4/2011 | Scully et al. |
| 2011/0082462 A1 | 4/2011 | Suarez |
| 2011/0137122 A1 | 6/2011 | Kawai |
| 2011/0153252 A1 | 6/2011 | Govari |
| 2011/0160570 A1 | 6/2011 | Kariv |
| 2011/0196199 A1 | 8/2011 | Donhowe et al. |
| 2011/0218676 A1 | 9/2011 | Okazaki |
| 2011/0257480 A1 | 10/2011 | Takahashi |
| 2011/0258842 A1 | 10/2011 | Dukesherer et al. |
| 2011/0319910 A1 | 12/2011 | Roelle et al. |
| 2012/0000427 A1 | 1/2012 | Nilsson |
| 2012/0046522 A1 | 2/2012 | Naito |
| 2012/0059249 A1 | 3/2012 | Verard et al. |
| 2012/0059392 A1 | 3/2012 | Diolaiti |
| 2012/0069167 A1 | 3/2012 | Liu et al. |
| 2012/0071752 A1 | 3/2012 | Sewell |
| 2012/0071822 A1 | 3/2012 | Romo et al. |
| 2012/0071894 A1 | 3/2012 | Tanner et al. |
| 2012/0123441 A1 | 5/2012 | Au |
| 2012/0130217 A1 | 5/2012 | Kauphusman et al. |
| 2012/0209293 A1 | 8/2012 | Carlson |
| 2012/0215094 A1 | 8/2012 | Rahimian et al. |
| 2012/0253276 A1 | 10/2012 | Govari et al. |
| 2012/0283745 A1 | 11/2012 | Goldberg et al. |
| 2012/0289777 A1 | 11/2012 | Chopra |
| 2012/0302869 A1 | 11/2012 | Koyrakh |
| 2012/0328077 A1 | 12/2012 | Bouvier |
| 2013/0018306 A1 | 1/2013 | Ludwin |
| 2013/0085330 A1 | 4/2013 | Ramamurthy et al. |
| 2013/0090530 A1 | 4/2013 | Ramamurthy |
| 2013/0102846 A1 | 4/2013 | Sjostrom |
| 2013/0131503 A1 | 5/2013 | Schneider et al. |
| 2013/0144116 A1 | 6/2013 | Cooper et al. |
| 2013/0165854 A1 | 6/2013 | Sandhu et al. |
| 2013/0165945 A9 | 6/2013 | Roelle |
| 2013/0204124 A1 | 8/2013 | Duindam |
| 2013/0218005 A1 | 8/2013 | Desai |
| 2013/0303891 A1 | 11/2013 | Chopra |
| 2013/0303892 A1 | 11/2013 | Zhao |
| 2013/0325030 A1 | 12/2013 | Hourtash et al. |
| 2014/0114180 A1 | 4/2014 | Jain |
| 2014/0135985 A1 | 5/2014 | Coste-Maniere et al. |
| 2014/0142591 A1 | 5/2014 | Alvarez et al. |
| 2014/0163664 A1 | 6/2014 | Goldsmith |
| 2014/0222021 A1 | 8/2014 | Diolaiti et al. |
| 2014/0222207 A1 | 8/2014 | Bowling et al. |
| 2014/0235943 A1 | 8/2014 | Paris |
| 2014/0277333 A1 | 9/2014 | Lewis et al. |
| 2014/0296870 A1 | 10/2014 | Stern et al. |
| 2014/0316420 A1 | 10/2014 | Ballard et al. |
| 2014/0343416 A1 | 11/2014 | Panescu |
| 2014/0343569 A1 | 11/2014 | Turner |
| 2014/0357984 A1 | 12/2014 | Wallace et al. |
| 2014/0364870 A1 | 12/2014 | Alvarez et al. |
| 2015/0051592 A1 | 2/2015 | Kintz |
| 2015/0073267 A1 | 3/2015 | Brannan |
| 2015/0088161 A1 | 3/2015 | Hata |
| 2015/0104284 A1 | 4/2015 | Riedel |
| 2015/0119628 A1 | 4/2015 | Bharat et al. |
| 2015/0142013 A1 | 5/2015 | Tanner et al. |
| 2015/0150635 A1 | 6/2015 | Kilroy |
| 2015/0164596 A1 | 6/2015 | Romo et al. |
| 2015/0202015 A1 | 7/2015 | Elhawary |
| 2015/0223902 A1 | 8/2015 | Walker et al. |
| 2015/0255782 A1 | 9/2015 | Kim et al. |
| 2015/0265359 A1 | 9/2015 | Camarillo |
| 2015/0265807 A1 | 9/2015 | Park et al. |
| 2015/0305650 A1 | 10/2015 | Hunter |
| 2015/0311838 A1 | 10/2015 | Moule |
| 2015/0335480 A1 | 11/2015 | Alvarez et al. |
| 2015/0342695 A1 | 12/2015 | He |
| 2015/0359597 A1 | 12/2015 | Gombert et al. |
| 2015/0374956 A1 | 12/2015 | Bogusky |
| 2016/0000414 A1 | 1/2016 | Brown |
| 2016/0000495 A1 | 1/2016 | Elliott |
| 2016/0001038 A1 | 1/2016 | Romo et al. |
| 2016/0005168 A1 | 1/2016 | Merlet |
| 2016/0005220 A1 | 1/2016 | Weingarten |
| 2016/0005576 A1 | 1/2016 | Tsukamoto |
| 2016/0016319 A1 | 1/2016 | Remirez |
| 2016/0045269 A1 | 2/2016 | Elhawary et al. |

(56) References Cited

U.S. PATENT DOCUMENTS

| | | |
|---|---|---|
| 2016/0051221 A1 | 2/2016 | Dickhans et al. |
| 2016/0066794 A1 | 3/2016 | Klinder et al. |
| 2016/0073928 A1 | 3/2016 | Soper |
| 2016/0075030 A1 | 3/2016 | Takahashi |
| 2016/0081568 A1 | 3/2016 | Kolberg |
| 2016/0100772 A1 | 4/2016 | Ikuma |
| 2016/0128781 A1 | 5/2016 | Blohm et al. |
| 2016/0128992 A1 | 5/2016 | Hudson |
| 2016/0183841 A1 | 6/2016 | Duindam et al. |
| 2016/0184032 A1 | 6/2016 | Romo et al. |
| 2016/0206389 A1 | 7/2016 | Miller |
| 2016/0228032 A1 | 8/2016 | Walker et al. |
| 2016/0270865 A1 | 9/2016 | Landey et al. |
| 2016/0278865 A1 | 9/2016 | Capote |
| 2016/0287053 A1 | 10/2016 | Miura |
| 2016/0287111 A1 | 10/2016 | Jacobsen |
| 2016/0287279 A1 | 10/2016 | Bovay et al. |
| 2016/0287346 A1 | 10/2016 | Hyodo et al. |
| 2016/0331469 A1 | 11/2016 | Hall et al. |
| 2016/0338787 A1 | 11/2016 | Popovic |
| 2016/0346038 A1 | 12/2016 | Helgeson |
| 2016/0346924 A1 | 12/2016 | Hasegawa |
| 2016/0354057 A1 | 12/2016 | Hansen et al. |
| 2016/0360947 A1 | 12/2016 | Iida |
| 2016/0360949 A1 | 12/2016 | Hyodo |
| 2016/0372743 A1 | 12/2016 | Cho et al. |
| 2016/0374541 A1 | 12/2016 | Agrawal et al. |
| 2017/0007337 A1 | 1/2017 | Dan |
| 2017/0056215 A1 | 3/2017 | Nagesh et al. |
| 2017/0068796 A1 | 3/2017 | Passerini et al. |
| 2017/0100197 A1 | 4/2017 | Zubiate |
| 2017/0100199 A1 | 4/2017 | Yu et al. |
| 2017/0106904 A1 | 4/2017 | Hanson |
| 2017/0119481 A1 | 5/2017 | Romo et al. |
| 2017/0165011 A1 | 6/2017 | Bovay et al. |
| 2017/0165503 A1 | 6/2017 | Hautvast et al. |
| 2017/0172673 A1 | 6/2017 | Yu et al. |
| 2017/0189118 A1 | 7/2017 | Chopra |
| 2017/0202627 A1 | 7/2017 | Sramek et al. |
| 2017/0209073 A1 | 7/2017 | Sramek et al. |
| 2017/0245854 A1 | 8/2017 | Zemlok |
| 2017/0245885 A1 | 8/2017 | Lenker |
| 2017/0251988 A1 | 9/2017 | Weber et al. |
| 2017/0280978 A1 | 10/2017 | Yamamoto |
| 2017/0281049 A1 | 10/2017 | Yamamoto |
| 2017/0290631 A1 | 10/2017 | Lee et al. |
| 2017/0303889 A1 | 10/2017 | Grim |
| 2017/0304015 A1 | 10/2017 | Tavallaei et al. |
| 2017/0312481 A1 | 11/2017 | Covington et al. |
| 2017/0325715 A1 | 11/2017 | Mehendale et al. |
| 2017/0333679 A1 | 11/2017 | Jiang |
| 2017/0340396 A1 | 11/2017 | Romo et al. |
| 2017/0367782 A1 | 12/2017 | Schuh et al. |
| 2018/0025666 A1 | 1/2018 | Ho et al. |
| 2018/0064498 A1 | 3/2018 | Kapadia |
| 2018/0177383 A1 | 6/2018 | Noonan et al. |
| 2018/0177556 A1 | 6/2018 | Noonan |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0250085 A1 | 9/2018 | Simi |
| 2018/0271604 A1 | 9/2018 | Grout et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289243 A1 | 10/2018 | Landey et al. |
| 2018/0289431 A1 | 10/2018 | Draper et al. |
| 2018/0325499 A1 | 11/2018 | Landey et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000566 A1 | 1/2019 | Graetzel et al. |
| 2019/0000568 A1 | 1/2019 | Connolly et al. |
| 2019/0000576 A1 | 1/2019 | Mintz et al. |
| 2019/0083183 A1 | 3/2019 | Moll et al. |
| 2019/0105776 A1 | 4/2019 | Ho et al. |
| 2019/0107454 A1 | 4/2019 | Lin et al. |
| 2019/0110839 A1 | 4/2019 | Rafii-Tari et al. |
| 2019/0110843 A1 | 4/2019 | Ummalaneni |
| 2019/0151148 A1 | 4/2019 | Alvarez et al. |
| 2019/0167366 A1 | 6/2019 | Ummalaneni |
| 2019/0167367 A1 | 6/2019 | Walker et al. |
| 2019/0175009 A1 | 6/2019 | Mintz |
| 2019/0175062 A1 | 6/2019 | Rafii-Tari et al. |
| 2019/0175287 A1 | 6/2019 | Hill et al. |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0209252 A1 | 7/2019 | Walker et al. |
| 2019/0216548 A1 | 7/2019 | Ummalaneni |
| 2019/0216550 A1 | 7/2019 | Eyre et al. |
| 2019/0216576 A1 | 7/2019 | Eyre |
| 2019/0223974 A1 | 7/2019 | Romo |
| 2019/0228525 A1 | 7/2019 | Mintz et al. |
| 2019/0228528 A1 | 7/2019 | Mintz et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298458 A1 | 10/2019 | Srinivasan et al. |
| 2019/0298460 A1 | 10/2019 | Al-Jadda |
| 2019/0298465 A1 | 10/2019 | Chin |
| 2019/0328213 A1 | 10/2019 | Landey et al. |
| 2019/0336238 A1 | 11/2019 | Yu |
| 2019/0365201 A1 | 12/2019 | Noonan et al. |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0375383 A1 | 12/2019 | Alvarez |
| 2019/0380787 A1 | 12/2019 | Ye |
| 2019/0380797 A1 | 12/2019 | Yu |
| 2020/0000530 A1 | 1/2020 | DeFonzo et al. |
| 2020/0000533 A1 | 1/2020 | Schuh |
| 2020/0008874 A1 | 1/2020 | Barbagli et al. |
| 2020/0022767 A1 | 1/2020 | Hill |
| 2020/0038123 A1 | 2/2020 | Graetzel |
| 2020/0039086 A1 | 2/2020 | Meyer |
| 2020/0046434 A1 | 2/2020 | Graetzel |
| 2020/0054405 A1 | 2/2020 | Schuh et al. |
| 2020/0054408 A1 | 2/2020 | Schuh et al. |
| 2020/0060516 A1 | 2/2020 | Baez |
| 2020/0093549 A1 | 3/2020 | Chin |
| 2020/0093554 A1 | 3/2020 | Schuh |
| 2020/0100845 A1 | 4/2020 | Julian |
| 2020/0100853 A1 | 4/2020 | Ho |
| 2020/0100855 A1 | 4/2020 | Leparmentier |
| 2020/0101264 A1 | 4/2020 | Jiang |
| 2020/0107894 A1 | 4/2020 | Wallace |
| 2020/0121502 A1 | 4/2020 | Kintz |
| 2020/0146769 A1 | 5/2020 | Eyre |
| 2020/0188043 A1 | 6/2020 | Yu |
| 2020/0197112 A1 | 6/2020 | Chin |
| 2020/0206472 A1 | 7/2020 | Ma |
| 2020/0217733 A1 | 7/2020 | Lin |
| 2020/0222134 A1 | 7/2020 | Schuh |
| 2020/0237458 A1 | 7/2020 | DeFonzo |
| 2020/0246591 A1 | 8/2020 | Bogusky |
| 2020/0261172 A1 | 8/2020 | Romo |

FOREIGN PATENT DOCUMENTS

| | | |
|---|---|---|
| CN | 1857877 | 11/2006 |
| CN | 101325920 | 12/2008 |
| CN | 102316817 | 1/2012 |
| CN | 102458295 | 5/2012 |
| CN | 102711586 | 10/2012 |
| CN | 102973317 | 3/2013 |
| CN | 103565529 | 2/2014 |
| CN | 103735313 | 4/2014 |
| CN | 103767659 | 5/2014 |

(56) References Cited

FOREIGN PATENT DOCUMENTS

| | | |
|---|---|---|
| CN | 103930063 | 7/2014 |
| CN | 104684502 | 6/2015 |
| CN | 105030331 | 11/2015 |
| CN | 105559850 | 5/2016 |
| CN | 105559886 | 5/2016 |
| CN | 105611881 | 5/2016 |
| CN | 107028659 | 8/2017 |
| CN | 104931059 | 9/2018 |
| DE | 19729499 | 1/1999 |
| DE | 102013100605 | 7/2014 |
| EP | 1 250 986 | 10/2002 |
| EP | 1 566 150 | 8/2005 |
| EP | 1 800 593 | 6/2007 |
| EP | 2 158 834 | 3/2010 |
| EP | 2 392 435 | 12/2011 |
| EP | 3 025 630 | 6/2016 |
| JP | 2008-528130 | 7/2008 |
| JP | 2009-509654 | 3/2009 |
| JP | 2009-524530 | 7/2009 |
| JP | 2011-088260 | 5/2011 |
| JP | 2013-510662 | 3/2013 |
| JP | 2013510673 A | 3/2013 |
| KR | 20160129311 A | 11/2016 |
| KR | 20170038012 A | 4/2017 |
| RU | 2569699 C2 | 11/2015 |
| WO | WO 01/56457 | 8/2001 |
| WO | 02061371 A1 | 8/2002 |
| WO | WO 04/029782 | 4/2004 |
| WO | 2004114037 A3 | 9/2005 |
| WO | WO 05/087128 | 9/2005 |
| WO | 2006079108 A1 | 7/2006 |
| WO | WO 06/122061 | 11/2006 |
| WO | 2007041094 A1 | 4/2007 |
| WO | 2007114975 A3 | 5/2008 |
| WO | WO 09/120940 | 10/2009 |
| WO | 2010093153 A2 | 8/2010 |
| WO | 2010133733 A1 | 11/2010 |
| WO | 2011100110 A1 | 8/2011 |
| WO | 2011125007 A1 | 10/2011 |
| WO | WO 11/132409 | 10/2011 |
| WO | 2012044334 A2 | 4/2012 |
| WO | WO 12/044334 | 4/2012 |
| WO | 2013071071 A1 | 5/2013 |
| WO | 2014052428 A1 | 4/2014 |
| WO | WO 14/114551 | 7/2014 |
| WO | 2015034906 A1 | 3/2015 |
| WO | WO 15/142957 | 9/2015 |
| WO | 2016018646 A1 | 2/2016 |
| WO | 2016175489 A1 | 11/2016 |
| WO | WO 17/048194 | 3/2017 |

OTHER PUBLICATIONS

JP Office Action for Appl. No. 2020-564810, dated Feb. 22, 2023, 5 pages.
Non-Final Rejection for U.S. Appl. No. 16/273,985, dated Oct. 25, 2019, 10 pages.
Notice of Allowance for U.S. Appl. No. 16/273,985, dated May 6, 2020, 8 pages.
Search report for appl No. 19754817.5, dated Oct. 22, 2021, 8 pages.
KR Office Action for Appl. No. 10-2020-7026388, dated Oct. 10, 2023, 5 pages.
Blankenstein, Jun. 2008, Dynamic Registration and High Speed Visual Servoing in Robot-Assisted Surgery, Katholieke Universiteit Leuven, Leuven, Belgium.
Kukuk, Oct. 5, 2001, TBNA-protocols: Guiding TransBronchial Needle Aspirations Without a Computer in the Operating Room, MICCAI 2001, 2208:997-1006.
Lawton et al., 1999, Ribbons and groups: A thin rod theory for catheters and filaments, J. Phys. A., 1999, 32:1709-1735.
Sturges et al., 1996, 48 A voice-actuated, tendon-controlled device for endoscopy, in Taylor et al. (eds.), Computer-Integrated Surgery: Technology and Clinical Applications, The MIT Press, Cambridge, MA, pp. 603-617.
Sturges et al., Apr. 1993, A flexible, tendon-controlled device for endoscopy, The International Journal of Robotics Research, 12(2):121-131.
Verdaasdonk et al., Jan. 23, 2012, Effect of microsecond pulse length and tip shape on explosive bubble formation of 2.78 µm Er,Cr;YSGG and 2.94 µm Er:YAG laser, Proceedings of SPIE, vol. 8221, 12.
International Search Report and Written Opinion in application No. PCT/US2019/17676, dated Jul. 22, 2019.
Decision to Grant Patent for Appl. No. 10-2020-7026388, dated Apr. 25, 2024, 1 page.

SYSTEM AND METHOD FOR DRIVING MEDICAL INSTRUMENT

CROSS-REFERENCE TO RELATED APPLICATION

This application is a continuation of U.S. application Ser. No. 16/273,985, filed Feb. 12, 2019, which claims the benefit of U.S. Provisional Application No. 62/630,112, filed Feb. 13, 2018, each of which is hereby incorporated by reference in its entirety.

TECHNICAL FIELD

The systems and methods disclosed herein are directed to systems and methods for driving a medical instrument, and more particularly, to techniques for driving a medical instrument in which an inner body is configured to be driven through a lumen of an outer body.

BACKGROUND

Medical procedures such as endoscopy (e.g., bronchoscopy) may involve the insertion of a medical tool into a patient's luminal network (e.g., airways) for diagnostic and/or therapeutic purposes. Surgical robotic systems may be used to control the insertion and/or manipulation of the medical tool during a medical procedure. The surgical robotic system may comprise at least one robotic arm including a manipulator assembly which may be used to control the positioning of the medical tool prior to and during the medical procedure. Certain medical tools may comprise an outer body and an inner body configured to be driven through a lumen of the outer body. For certain medical procedures, it may be desirable to have independent control of the inner and outer bodies of the medical instrument.

SUMMARY

The systems, methods and devices of this disclosure each have several innovative aspects, no single one of which is solely responsible for the desirable attributes disclosed herein.

In one aspect, there is provided a robotic surgical system, comprising: a medical instrument comprising an outer body and an inner body configured to be driven through a lumen in the outer body; a set of one or more robotic arm assemblies instrument manipulators configured to control movement of the outer and inner bodies; a set of one or more user input devices; a set of one or more processors; and at least one computer-readable memory in communication with the set of processors and having stored thereon computer-executable instructions to cause the set of processors to: receive, via the set of user input devices, a change drive mode command; and in response to receiving the change drive mode command, change a drive mode of the medical instrument from a paired drive mode to an unpaired drive mode in which a distance between a distal end of the inner body and a distal end of the outer body is maintained at a predetermined distance in response to receiving a drive command from the set of input devices.

In another aspect, there is provided a robotic surgical system, comprising: a medical instrument comprising an outer body and an inner body configured to be driven through a lumen in the outer body; a set of one or more instrument manipulators configured to control movement of the outer and inner bodies; a set of one or more user input devices; a set of one or more processors; and at least one computer-readable memory in communication with the set of processors and having stored thereon computer-executable instructions to cause the set of processors to: receive, via the set of user input devices, an articulation command to articulate the medical instrument; treat one of the outer and inner bodies as a primary body and the other one of the outer and inner bodies as a secondary body; determine the distance between a distal end of the inner body and a distal end of the outer body; determine a co-articulation factor based on the determined distance; articulate, via the set of instrument manipulators, the primary body based on the articulation command; and articulate, via the set of instrument manipulators, the secondary body based on the articulation command and the co-articulation factor.

In yet another aspect, there is provided a robotic surgical system, comprising: a medical instrument comprising an outer body and an inner body configured to be driven through a lumen in the outer body; a set of one or more instrument manipulators configured to control movement of the outer and inner bodies; a set of one or more feedback devices; a set of one or more processors; at least one computer-readable memory in communication with the set of processors and having stored thereon a model of a mapped portion of the luminal network, a position of a target with respect to the model, and a path along the model from an access point to the target, the memory further storing computer-executable instructions to cause the set of processor to: identify a portion of the luminal network along the path having a shape matching a park assistance signature; and cause, on at least a portion of the set of feedback devices, a parking indication at a position corresponding to the identified portion with respect to the model, the parking indication representing a place to park the distal end of the outer body.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

1. Overview.

Aspects of the present disclosure may be integrated into a robotically-enabled medical system capable of performing a variety of medical procedures, including both minimally invasive, such as laparoscopy, and non-invasive, such as endoscopy, procedures. Among endoscopy procedures, the system may be capable of performing bronchoscopy, ureteroscopy, gastroenterology, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
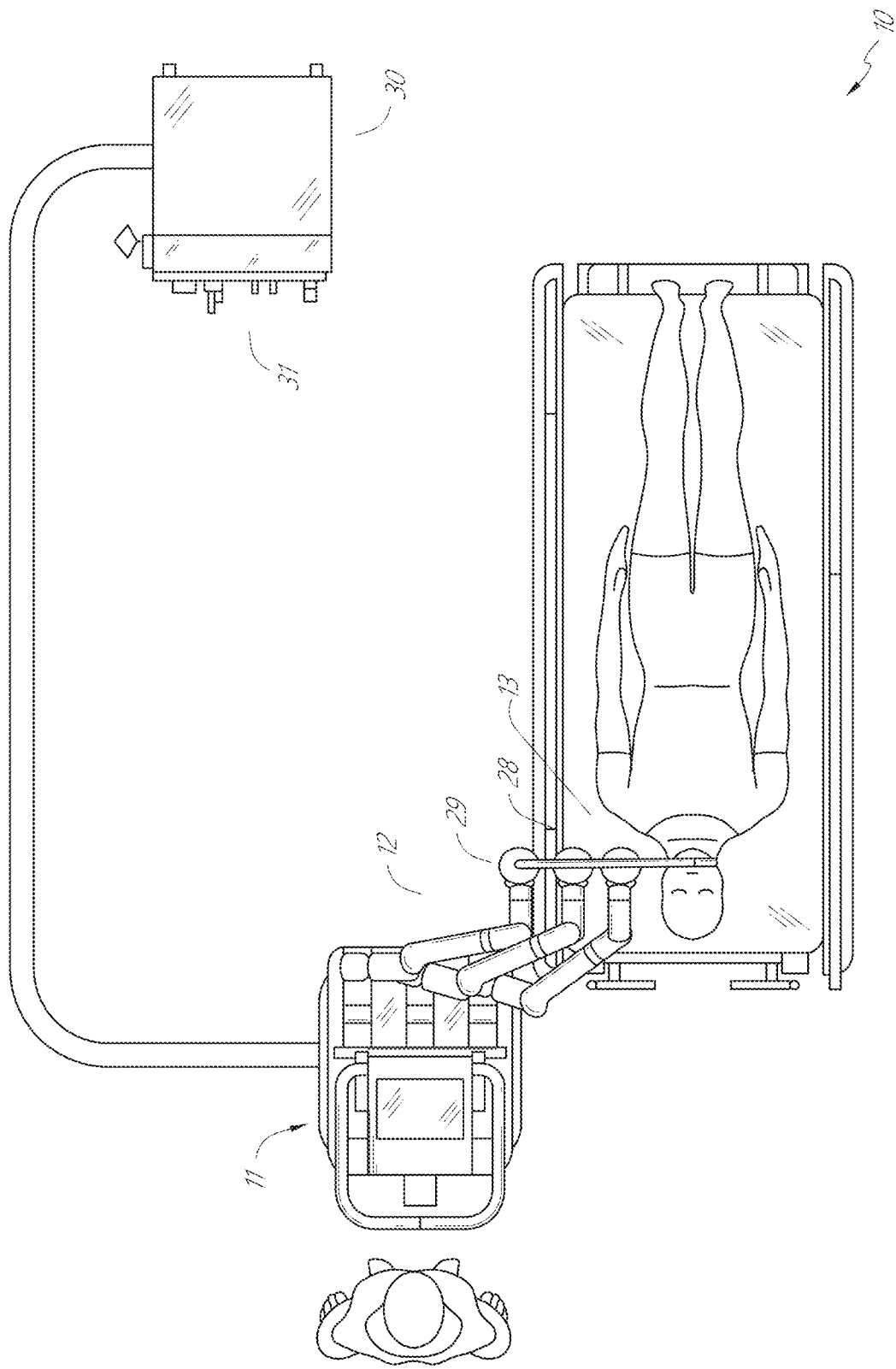
FIG. 1 illustrates an embodiment of a cart-based robotic system arranged for diagnostic and/or therapeutic bronchoscopy procedure(s).
Figure 2:
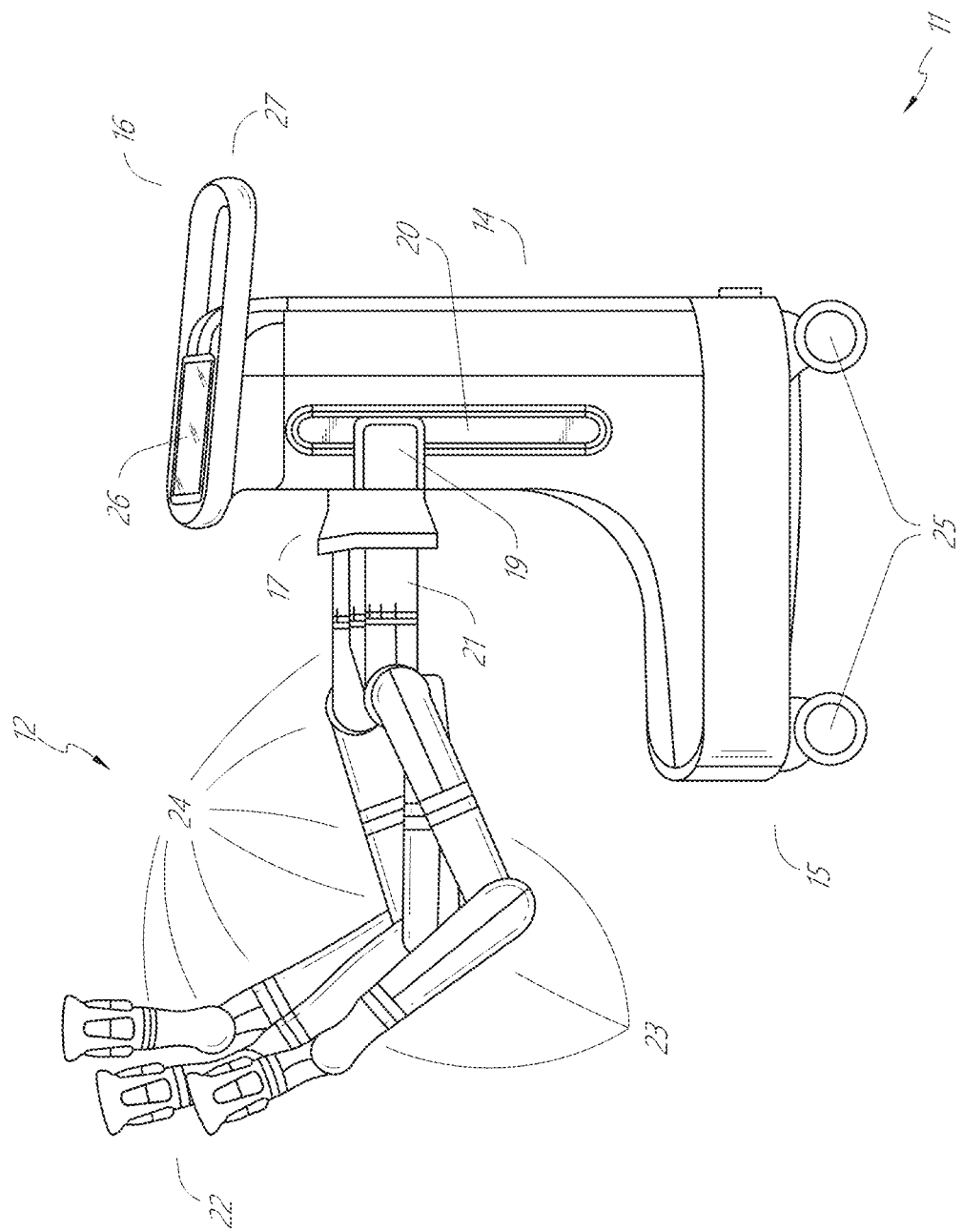
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy procedure. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independent of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments may need to be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to system that may be deployed through the endoscope 13. These components may also be controlled using the computer system of tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include opto-electronics equipment for detecting, receiving, and processing data received from the optical sensors or cameras throughout the robotic system 10. In combination with the control system, such opto-electronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in system 10 are generally designed to provide both robotic controls as well as pre-operative and real-time information of the procedure, such as navigational and localization information of the endoscope 13. When the console 31 is not the only console available to the physician, it may be used by a second operator, such as a nurse, to monitor the health or vitals of the patient and the operation of system, as well as provide procedure-specific data, such as navigational and localization information.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart, the support for controls, optics, fluidics, and/or navigation may be provided through a separate cable.

FIG. 2 provides a detailed illustration of an embodiment of the cart from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm. Each of the arms 12 have seven joints, and thus provide seven degrees of freedom. A multitude of joints result in a multitude of degrees of freedom, allowing for "redundant" degrees of freedom. Redundant degrees of freedom allow the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and arms 12 over the floor. Accordingly, the cart base 15 houses heavier components, such as electronics, motors, power supply, as well as components that either enable movement and/or immobilize the cart. For example, the cart base 15 includes rollable wheel-shaped casters 25 that allow for the cart to easily move around the room prior to a procedure. After reaching the appropriate position, the casters 25 may be immobilized using wheel locks to hold the cart 11 in place during the procedure.

Positioned at the vertical end of column 14, the console 16 allows for both a user interface for receiving user input and a display screen (or a dual-purpose device such as, for example, a touchscreen 26) to provide the physician user with both pre-operative and intra-operative data. Potential pre-operative data on the touchscreen 26 may include pre-operative plans, navigation and mapping data derived from pre-operative computerized tomography (CT) scans, and/or notes from pre-operative patient interviews. Intra-operative data on display may include optical information provided from the tool, sensor and coordinate information from sensors, as well as vital patient statistics, such as respiration, heart rate, and/or pulse. The console 16 may be positioned and tilted to allow a physician to access the console from the side of the column 14 opposite carriage 17. From this position, the physician may view the console 16, robotic arms 12, and patient while operating the console 16 from behind the cart 11. As shown, the console 16 also includes a handle 27 to assist with maneuvering and stabilizing cart 11.

Figure 3:
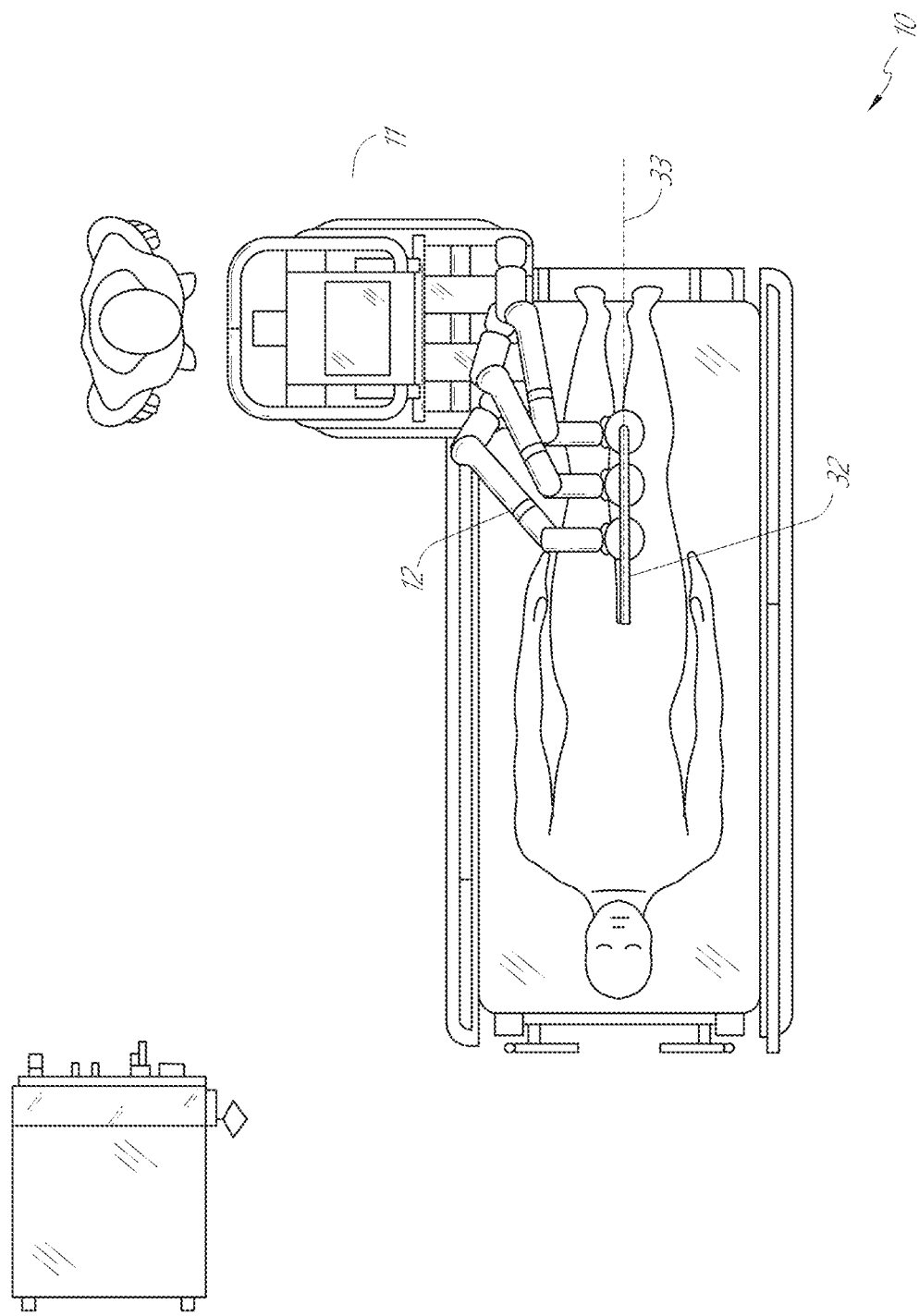
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using laser or ultrasonic lithotripsy device deployed down the working channel of the ureteroscope 32. After lithotripsy is complete, the resulting stone fragments may be removed using baskets deployed down the ureteroscope 32.

Figure 4:
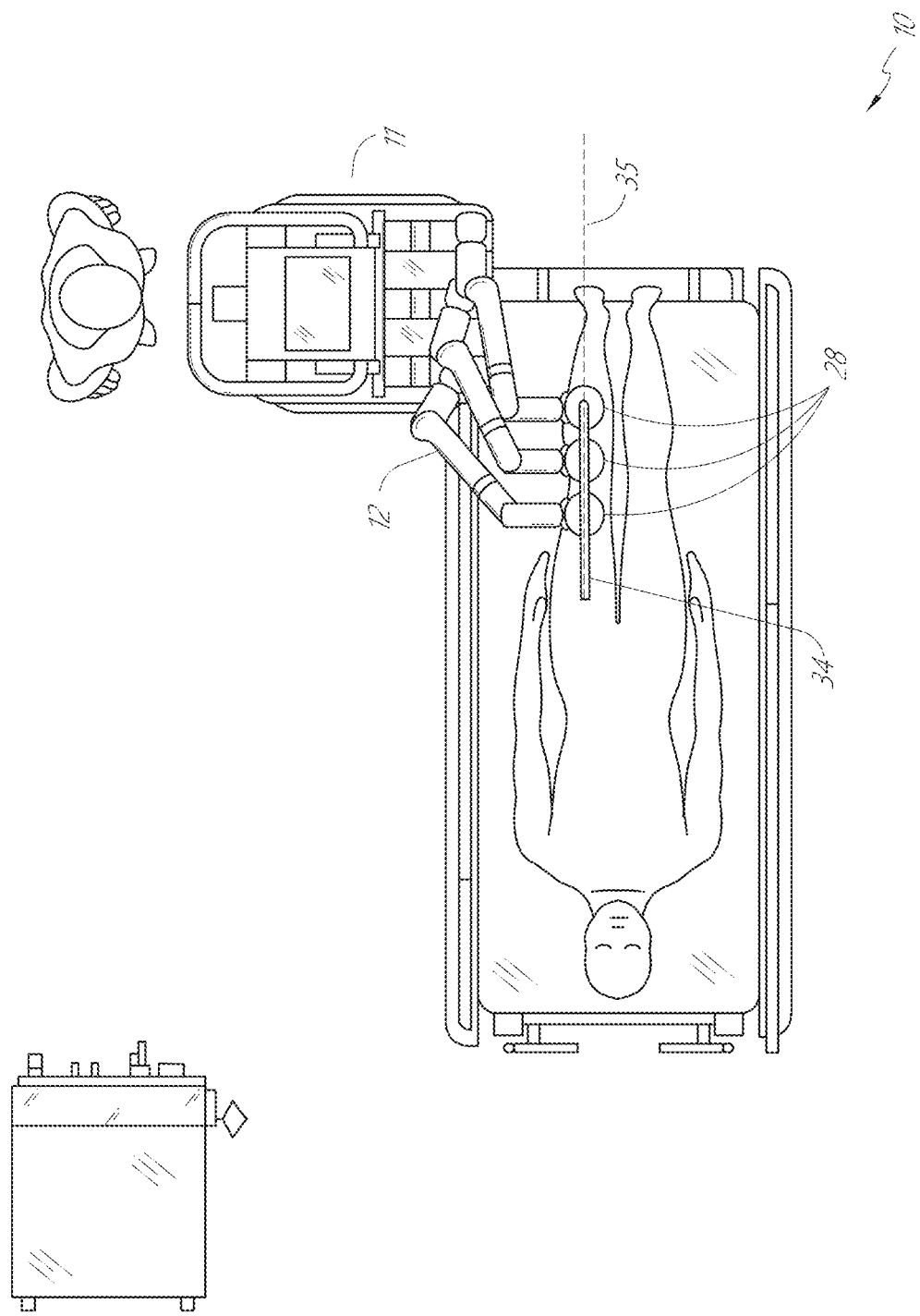
FIG. 4 illustrates an embodiment of the robotic system of FIG. 1 arranged for a vascular procedure.

FIG. 4 illustrates an embodiment of a robotically-enabled system similarly arranged for a vascular procedure. In a vascular procedure, the system 10 may be configured such the cart 11 may deliver a medical instrument 34, such as a steerable catheter, to an access point in the femoral artery in the patient's leg. The femoral artery presents both a larger diameter for navigation as well as relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
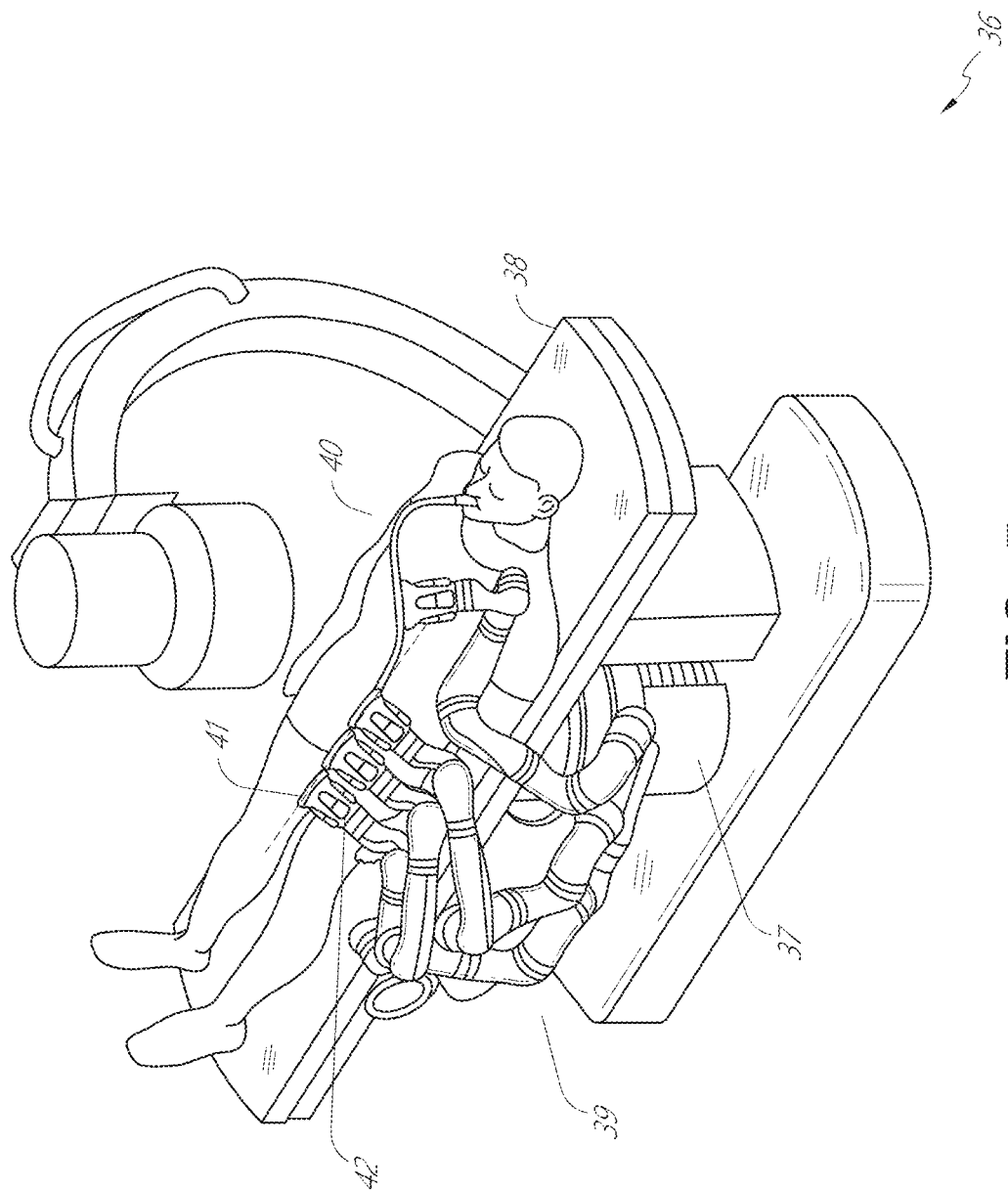
FIG. 5 illustrates an embodiment of a table-based robotic system arranged for a bronchoscopy procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopy procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around table 38.

Figure 6:
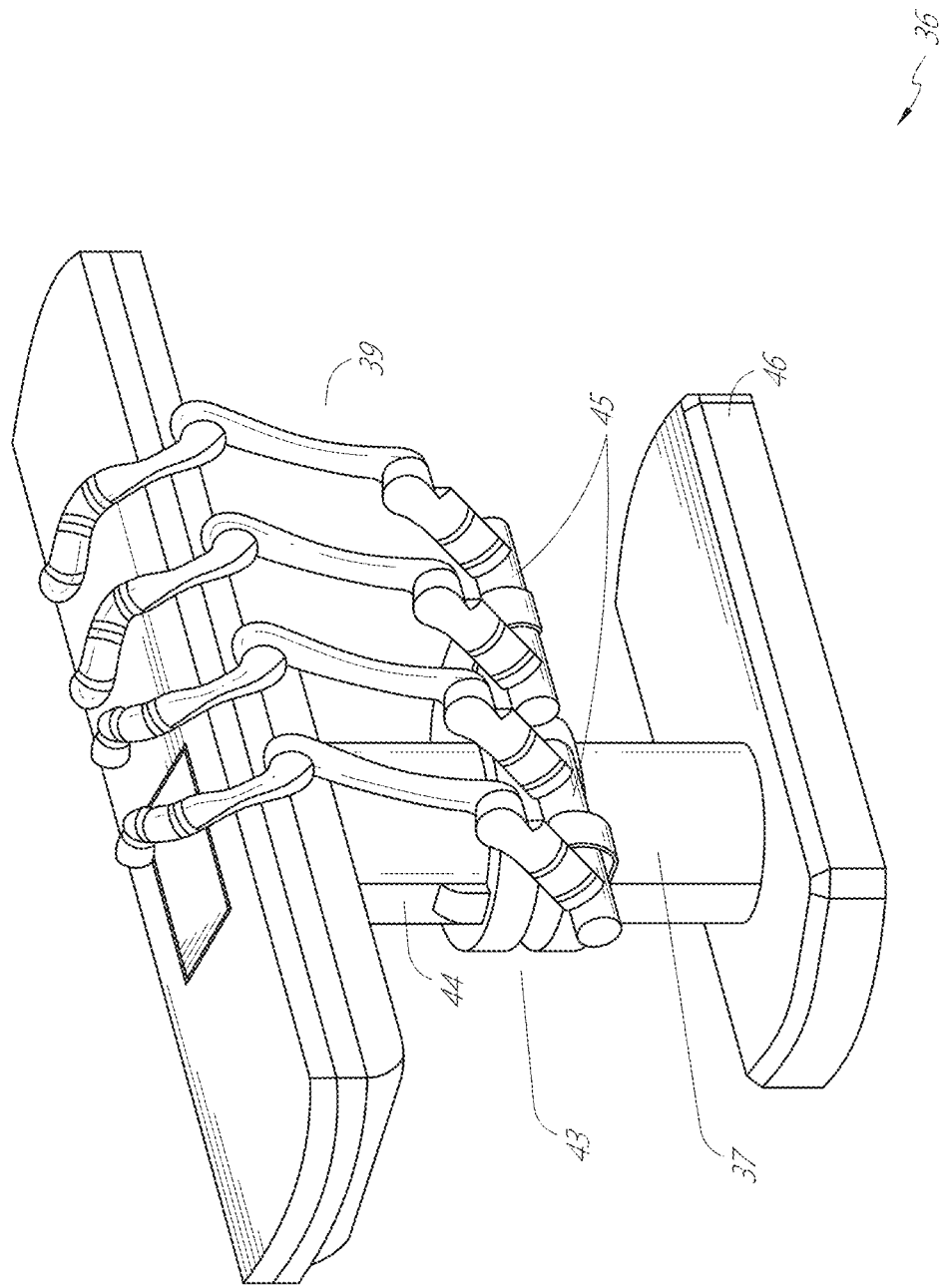
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independent of the other carriages. While carriages 43 need not surround the column 37 or even be circular, the ring-shape as shown facilitates rotation of the carriages 43 around the column 37 while maintaining structural balance. Rotation and translation of the carriages 43 allows the system to align the medical instruments, such as endoscopes and laparoscopes, into different access points on the patient.

Figure 9:
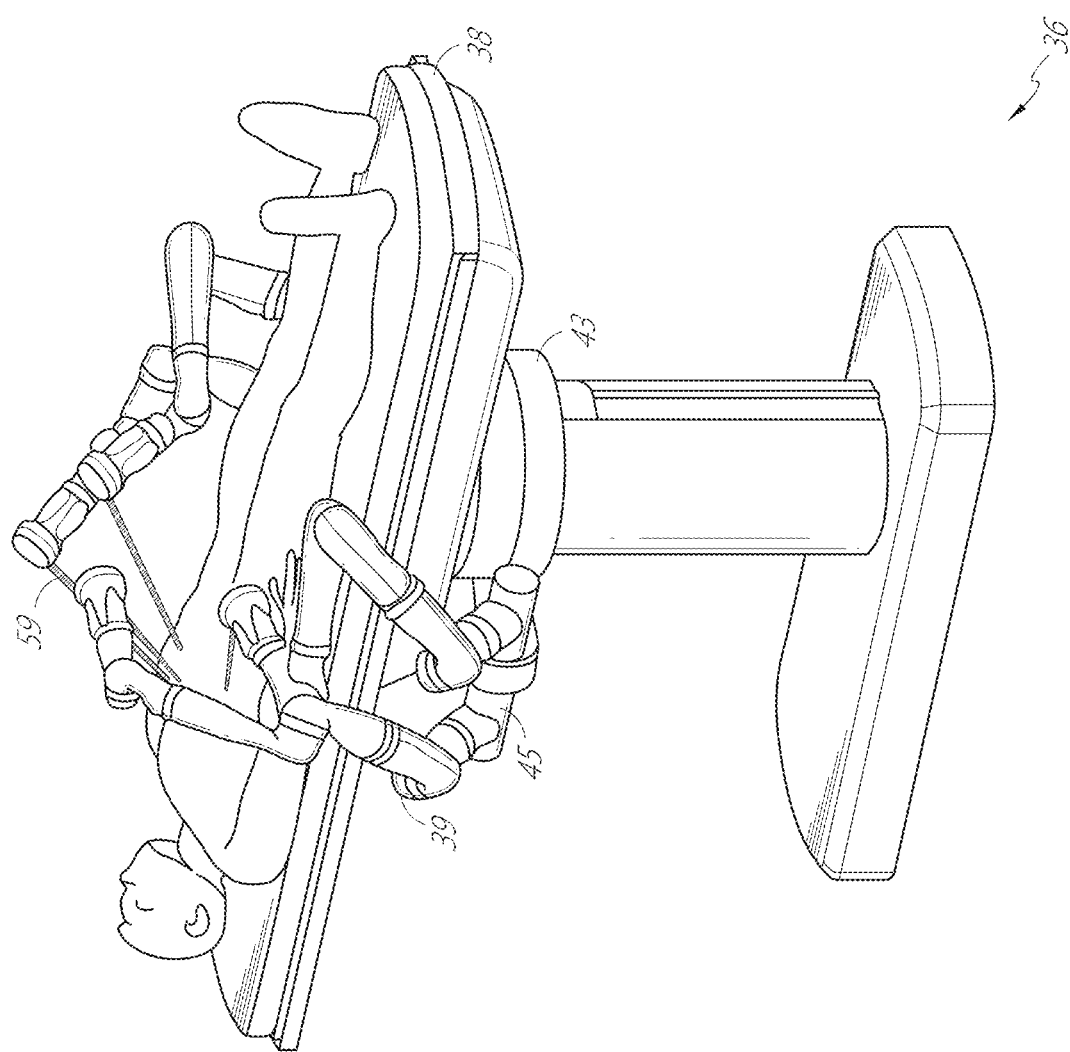
FIG. 9 illustrates an embodiment of a table-based robotic system configured for a laparoscopic procedure.

The arms 39 may be mounted on the carriages through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of table 38 (as shown in FIG. 6), on opposite sides of table 38 (as shown in FIG. 9), or on adjacent sides of the table 38 (not shown).

The column 37 structurally provides support for the table 38, and a path for vertical translation of the carriages. Internally, the column 37 may be equipped with lead screws for guiding vertical translation of the carriages, and motors to mechanize the translation of said carriages based the lead screws. The column 37 may also convey power and control signals to the carriage 43 and robotic arms 39 mounted thereon.

The table base 46 serves a similar function as the cart base 15 in cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

Continuing with FIG. 6, the system 36 may also include a tower (not shown) that divides the functionality of system 36 between table and tower to reduce the form factor and bulk of the table. As in earlier disclosed embodiments, the tower may provide a variety of support functionalities to table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base for potential stowage of the robotic arms. The tower may also include a console that provides both a user interface for user input, such as keyboard and/or pendant, as well as a display screen (or touchscreen) for pre-operative and intra-operative information, such as real-time imaging, navigation, and tracking information.

Figure 7:
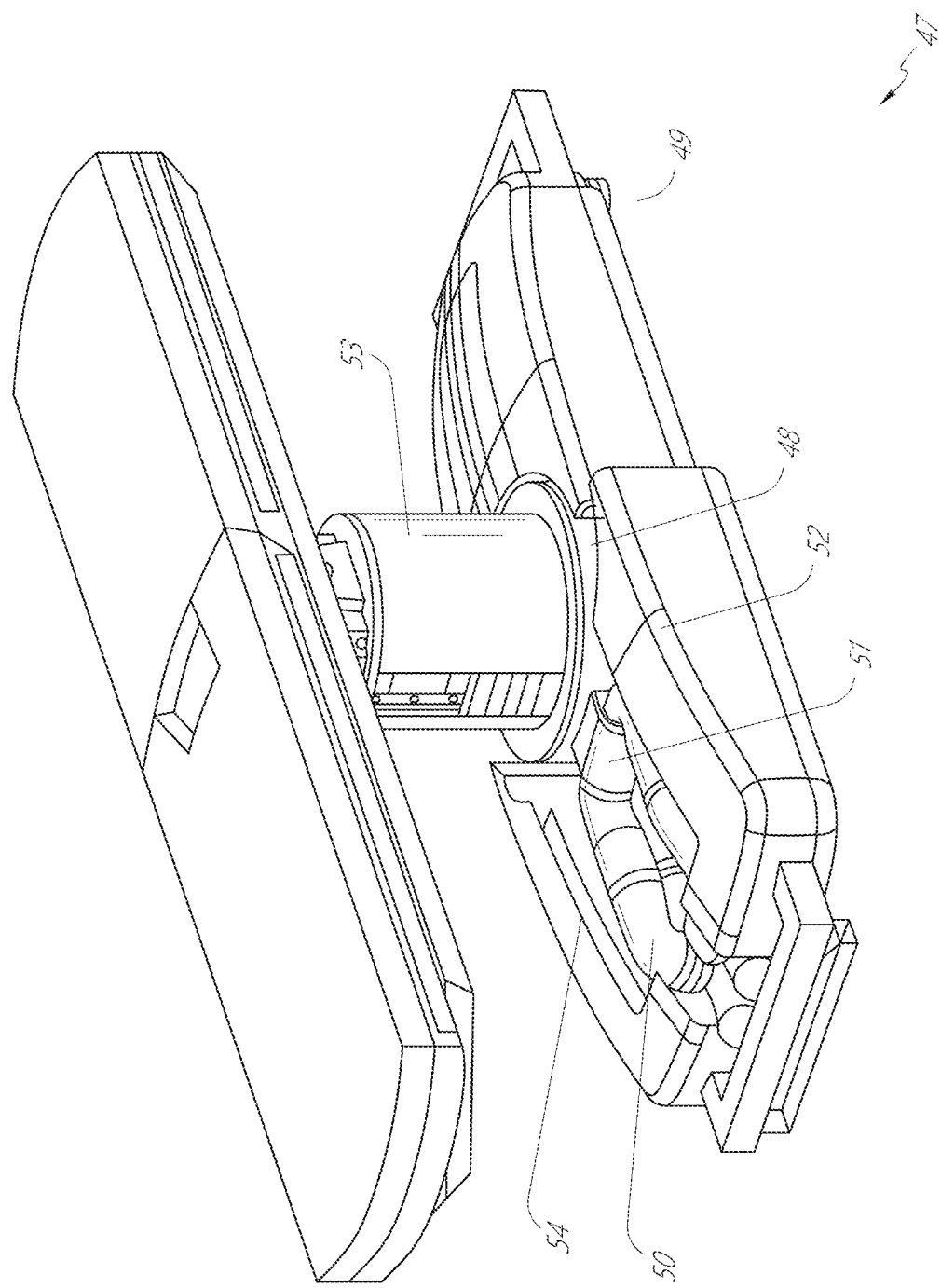
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and arms 50 around column 53, and closed to stow to protect them when not in use. The base covers 52 may be sealed with a membrane 54 along the edges of its opening to prevent dirt and fluid ingress when closed.

Figure 8:
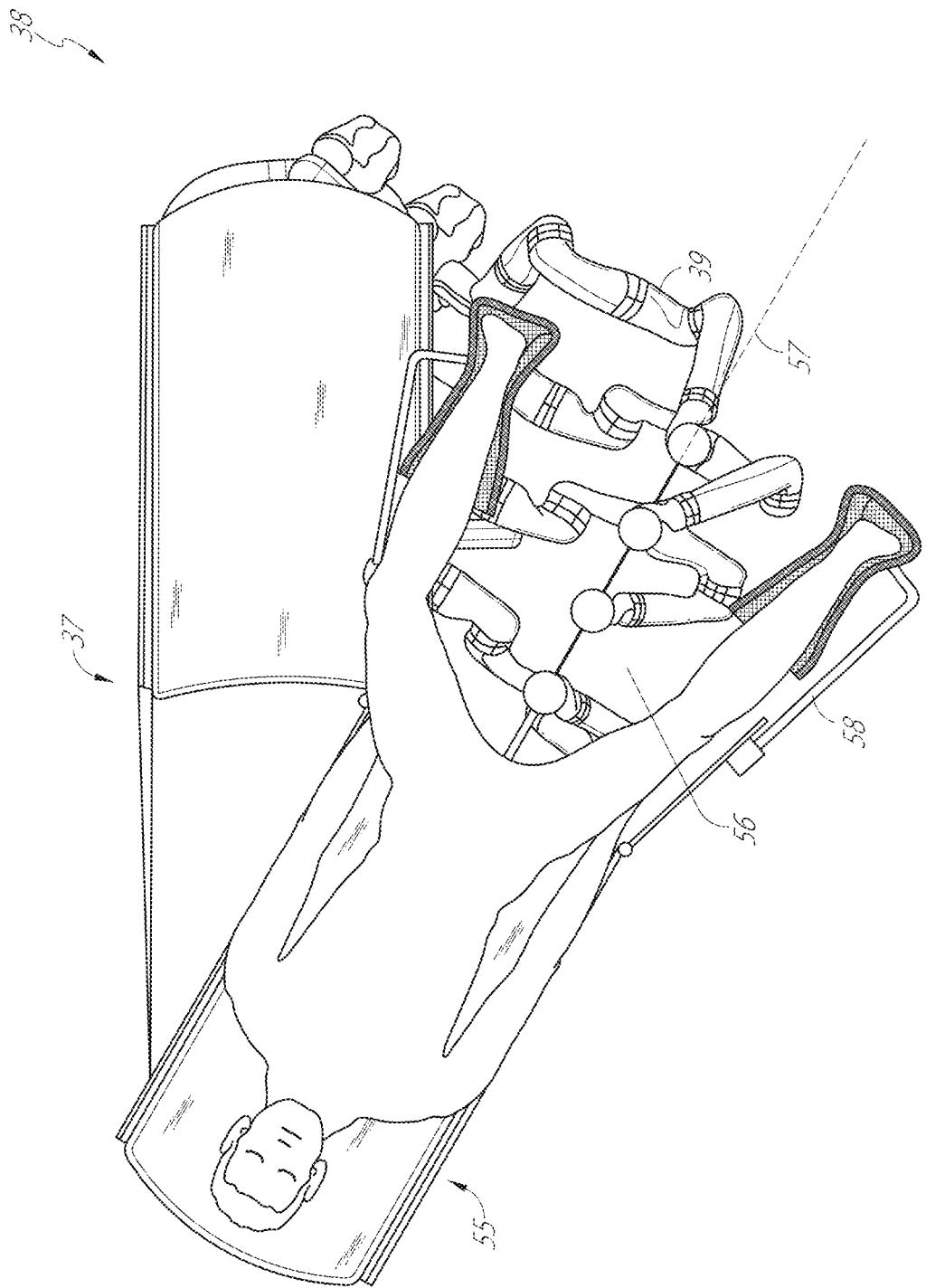
FIG. 8 illustrates an embodiment of a table-based robotic system configured for a ureteroscopy procedure.

FIG. 8 illustrates an embodiment of a robotically-enabled table-based system configured for a ureteroscopy procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments (elongated in shape to accommodate the size of the one or more incisions) may be inserted into the patient's anatomy. After inflation of the patient's abdominal cavity, the instruments, often referred to as laparoscopes, may be directed to perform surgical tasks, such as grasping, cutting, ablating, suturing, etc. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that laparoscopes 59 may be positioned using the arm mounts 45 to be passed through minimal incisions on both sides of the patient to reach his/her abdominal cavity.

Figure 10:
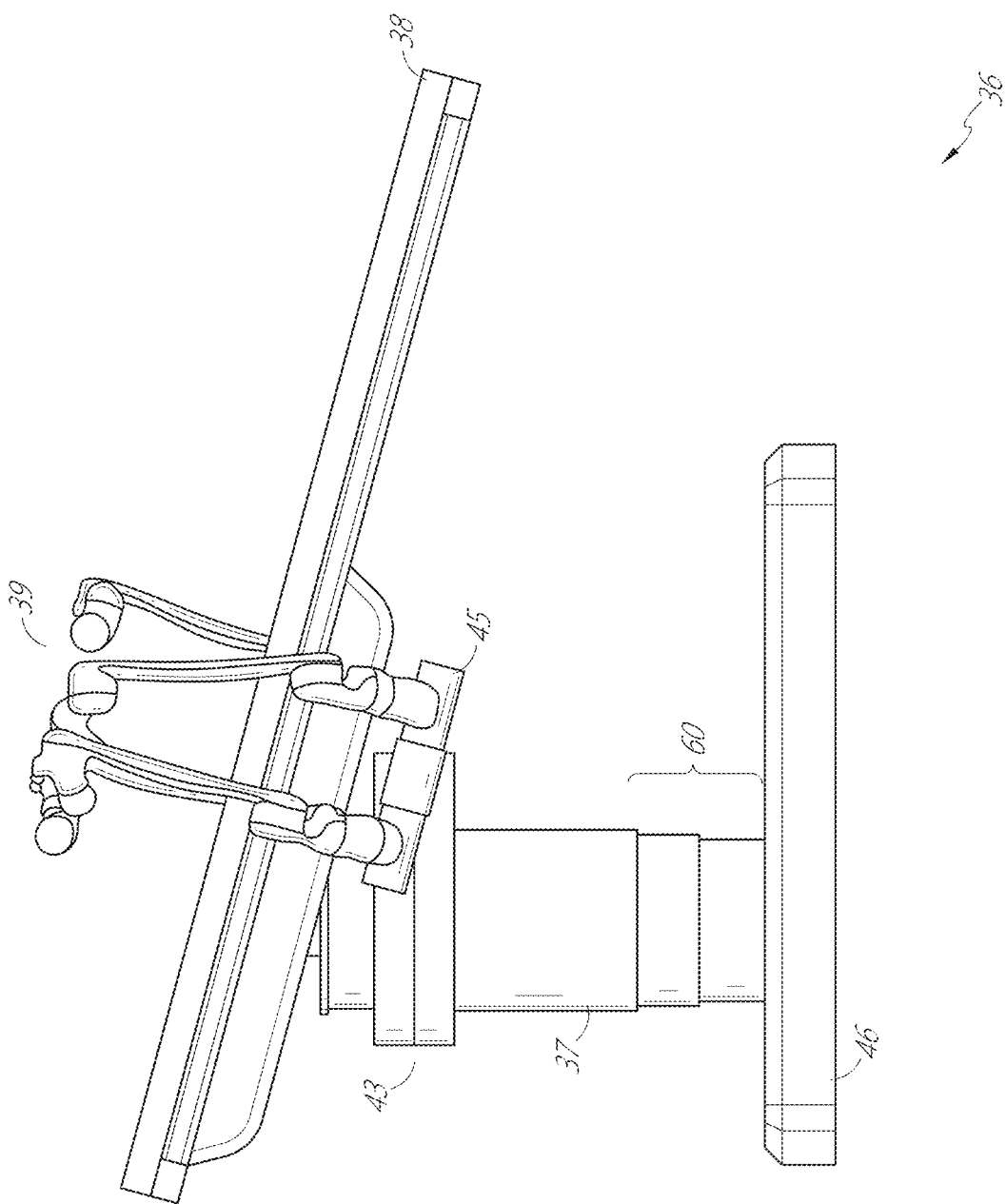
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the arms 39 maintain the same planar relationship with table 38. To accommodate steeper angles, the column 37 may also include telescoping portions 60 that allow vertical extension of column 37 to keep the table 38 from touching the floor or colliding with base 46.

Figure 11:
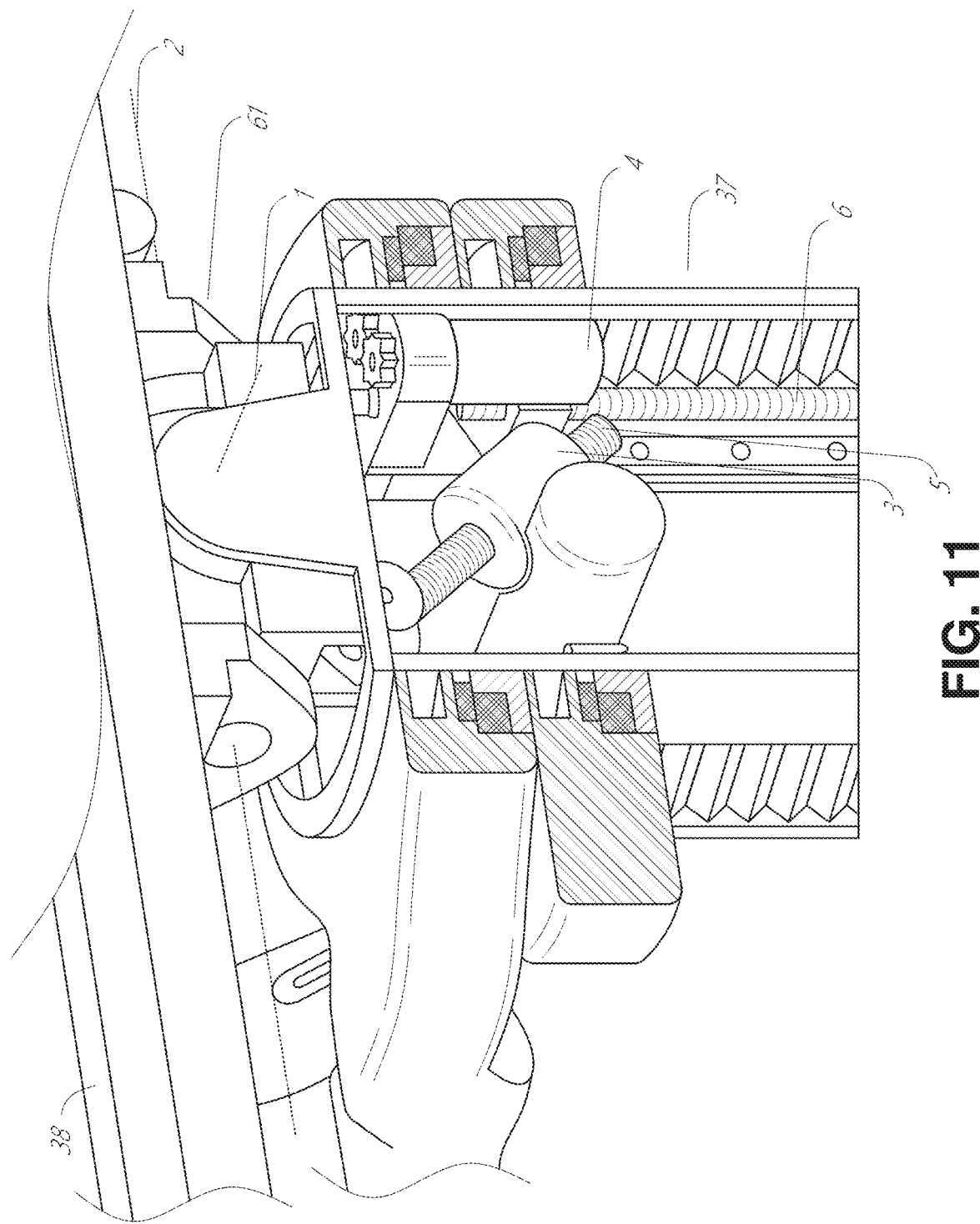
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical procedures, such as laparoscopic prostatectomy.

C. Instrument Driver & Interface.

The end effectors of the system's robotic arms comprise (i) an instrument driver (alternatively referred to as "instrument drive mechanism" or "instrument device manipulator") that incorporate electro-mechanical means for actuating the medical instrument and (ii) a removable or detachable medical instrument which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 12:
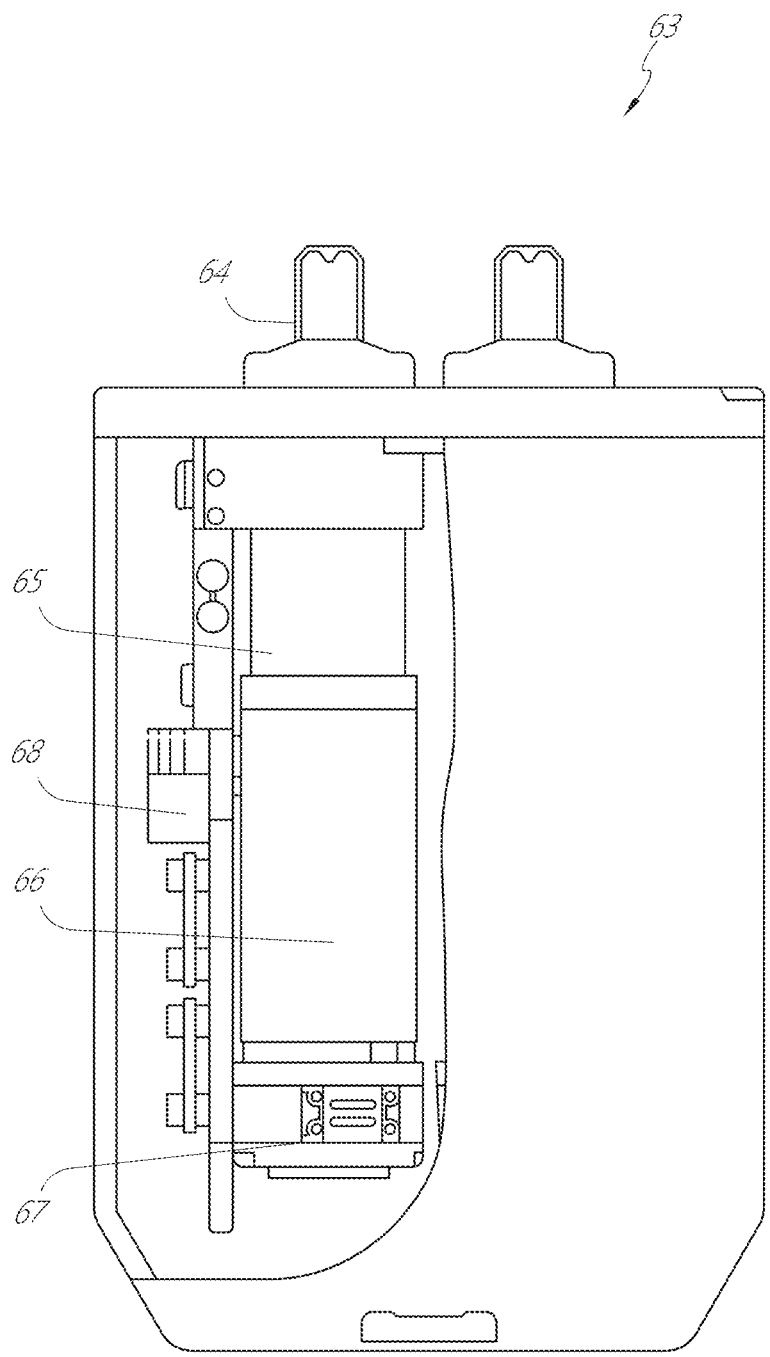
FIG. 12 illustrates an exemplary instrument driver.

FIG. 12 illustrates an example instrument driver. Positioned at the distal end of a robotic arm, instrument driver 62 comprises of one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuitry 68 for receiving control signals and actuating the drive unit. Each drive unit 63 being independent controlled and motorized, the instrument driver 62 may provide multiple (four as shown in FIG. 12) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 13:
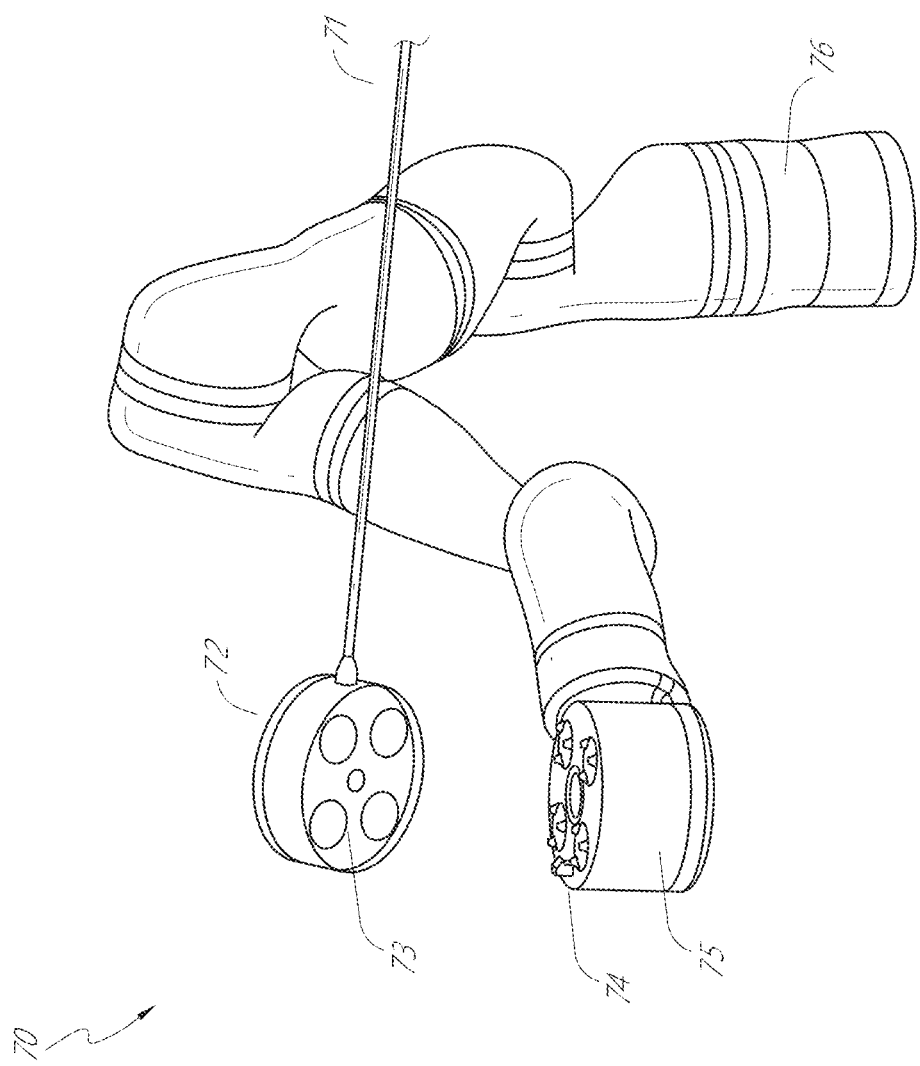
FIG. 13 illustrates an exemplary medical instrument with a paired instrument driver.

FIG. 13 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of instrument base 72 may share axes of rotation with the drive outputs 74 in the instrument driver 75 to allow the transfer of torque from drive outputs 74 to drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 66 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector comprising a jointed wrist formed from a clevis with an axis of rotation and a surgical tool, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons within the shaft 71. These individual tendons, such as pull wires, may be individually anchored to individual drive inputs 73 within the instrument handle 72. From the handle 72, the tendons are directed down one or more pull lumens within the elongated shaft 71 and anchored at the distal portion of the elongated shaft 71. In laparoscopy, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In laparoscopy, the tendon may cause a joint to rotate about an axis, thereby causing the end effector to move in one direction or another. Alternatively, the tendon may be connected to one or more jaws of a grasper at distal end of the elongated shaft 71, where tension from the tendon cause the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft may comprise of a working channel for deploying surgical tools, irrigation, and/or aspiration to the operative region at the distal end of the shaft 71. The shaft 71 may also accommodate wires and/or optical fibers to transfer signals to/from an optical assembly at the distal tip, which may include of an optical camera. The shaft 71 may also accommodate optical fibers to carry light from proximally-located light sources, such as light emitting diodes, to the distal end of the shaft.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 13, the drive shaft axes, and thus the drive input axes, are orthogonal to the axis of the elongated shaft. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongate shaft 71. The resulting entanglement of such tendons may disrupt any control algorithms intended to predict movement of the flexible elongate shaft during an endoscopic procedure.

Figure 14:
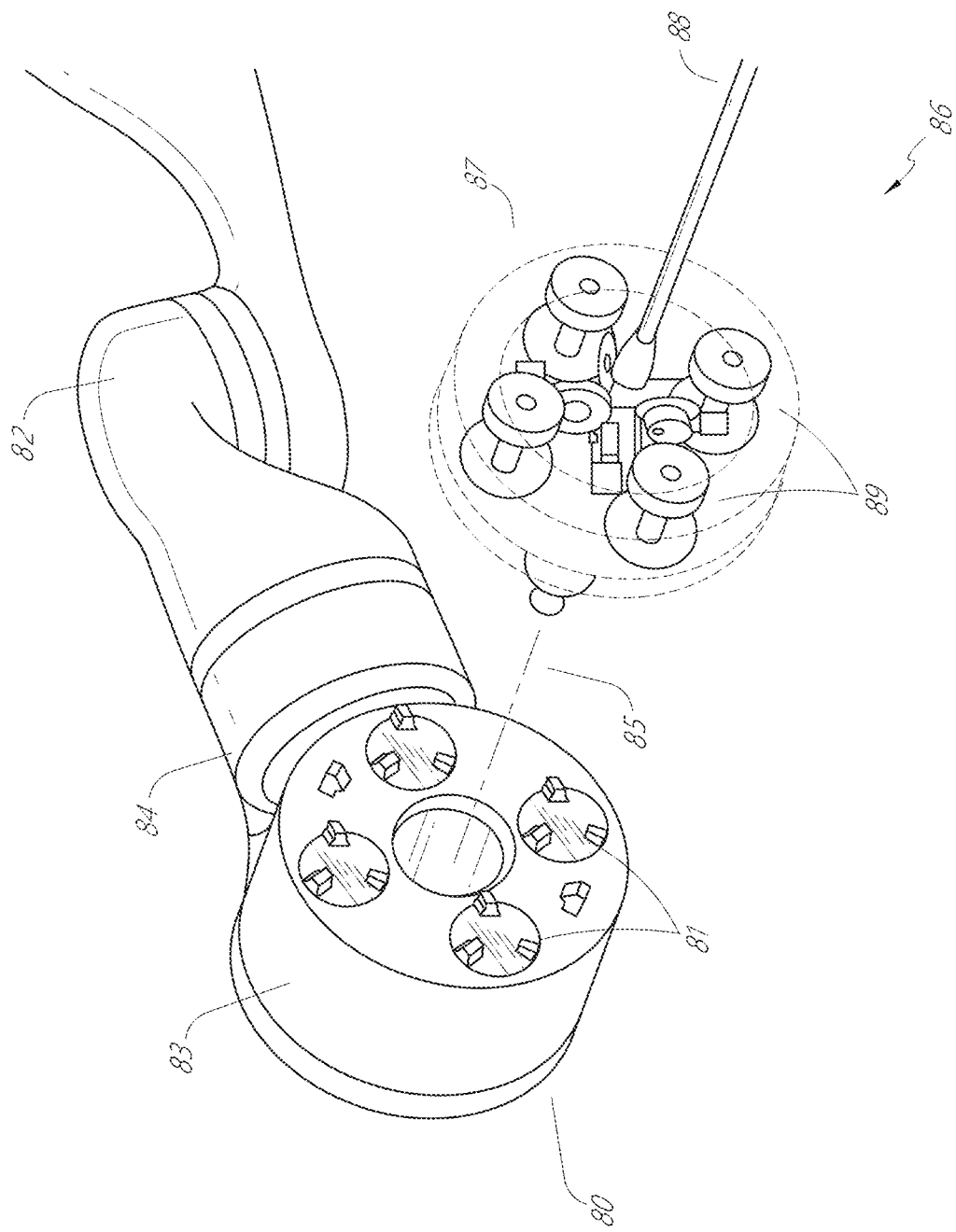
FIG. 14 illustrates an alternative design for an instrument driver and instrument where the axes of the drive units are parallel to the axis of the elongated shaft of the instrument.

FIG. 14 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver. Power and controls signals may be communicated from the non-rotational portion 84 of the instrument driver 80 to the rotational assembly 83 through electrical contacts may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise of an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, instrument shaft 88 extends from the center of instrument base 87 with an axis substantially parallel to the axes of the drive inputs 89, rather than orthogonal as in the design of FIG. 13.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

E. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 15:
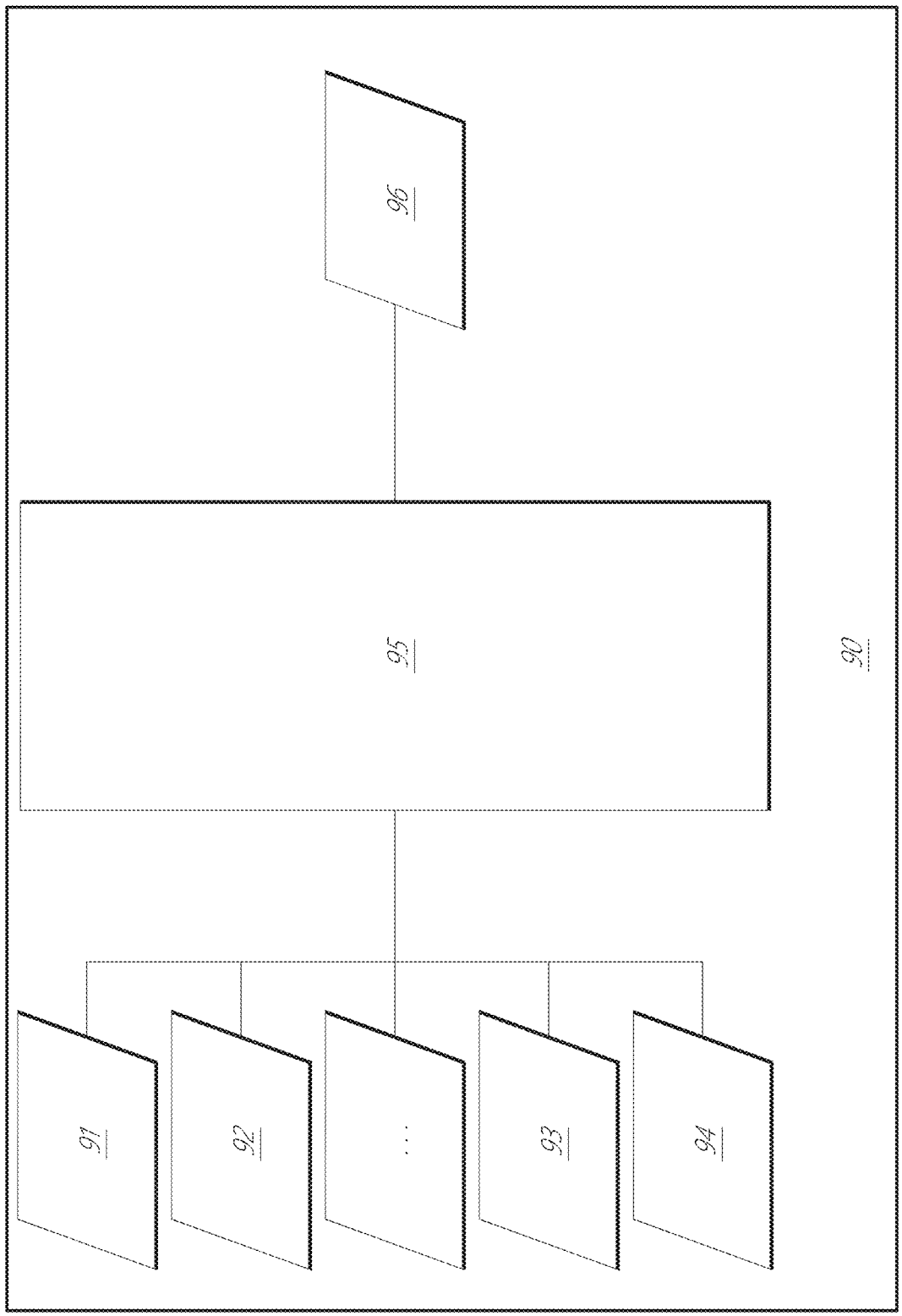
FIG. 15 depicts a block diagram illustrating a localization system that estimates a location of one or more elements of the robotic systems of FIGS. 1-10, such as the location of the instrument of FIGS. 13 and 14, in accordance to an example embodiment.

FIG. 15 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart shown in FIGS. 1-4, the beds shown in FIGS. 5-10, etc.

As shown in FIG. 15, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Pre-operative mapping may be accomplished through the use of the collection of low dose CT scans. Pre-operative CT scans are reconstructed into three-dimensional images, which are visualized, e.g., as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as preoperative model data 91. The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data 92. The localization module 95 may process the vision data to enable one or more vision-based location tracking. For example, the preoperative model data may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some feature of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 15 shows, a number of other input data can be used by the localization module 95. For example, although not shown in FIG. 15, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Medical Instrument Driving.

Embodiments of this disclosure relate to systems and techniques for driving a medical instrument having an inner body and an outer body. For example, a medical instrument may comprise two or more telescoping bodies which can be independently driven (e.g., advanced, retracted, articulated, rotated, etc.) based on commands received from a user of the system. As the number of independently controllable bodies increases, the number of commands which may be independently mapped to controlling the driving of the medical instrument also increases, thereby increasing the complexity of the system. Additionally, each body may be provided with a number of degrees of freedom available for controlling the corresponding body, leading to an even greater complexity in the number of control variables. The higher medical instrument control complexity may be associated with a greater number of available driving techniques which may not be achievable with a less complicated driving system.

For example, a standard single body endoscope may be configured to provide multiple degrees of freedom to the user, such as: insertion, roll, and articulation in various directions. In an example multibody endoscope including an inner body and an outer body, the system may provide 10 degrees of freedom (e.g., for each body, the degrees of freedom may include: 1 insertion degree of freedom and 4 independent pull wires, each providing an independent articulation degree of freedom). Other implementations may include greater or fewer degrees of freedom, which may provide, for example, roll of one or more of the outer and inner bodies. With 10 degrees of freedom, there may be a number of different combinations of techniques for achieving similar driving functionality. Additionally, certain techniques may have advantages over other techniques, such as reducing stress or wear on the medical instrument, thereby allowing the medical instrument, or portions thereof, to be used for a longer duration before replacement is required.

Although certain aspects of this disclosure may be described in accordance with a two body system including an outer body and an inner body, this disclosure is not limited to a two body medical instrument. For example, the medical instrument may further include a robotically controlled surgical instrument configured to be driven through a lumen in the inner body. The surgical instrument may be connected to a third robotic arm assembly to be independently controlled thereby. Accordingly, one skilled in the art would recognize that the concepts described below as generally applying to a medical instrument including an outer body and an inner body can also be applied to a three body system, or a system including greater number of independently driven bodies.

In order to reduce the cognitive load on a user of the system, the system may include a user input device configured to receive input commands in fewer degrees of freedom than achievable based on the structure of the medical instrument. For example, the user input device may be configured to receive user commands mapping to three degrees of freedom (e.g., insertion, yaw, and pitch). The system may then map these user commands to robot commands which correspond to the physical degrees of freedom used to control the inner and outer bodies of the medical instrument. This mapping may involve, among other things, determining to which of the inner and outer bodies to apply the command, which may involve driving both the inner and outer bodies in certain applications and/or coordinating movement of the inner and outer bodies in sequential or coordinated manner.

Figure 16:
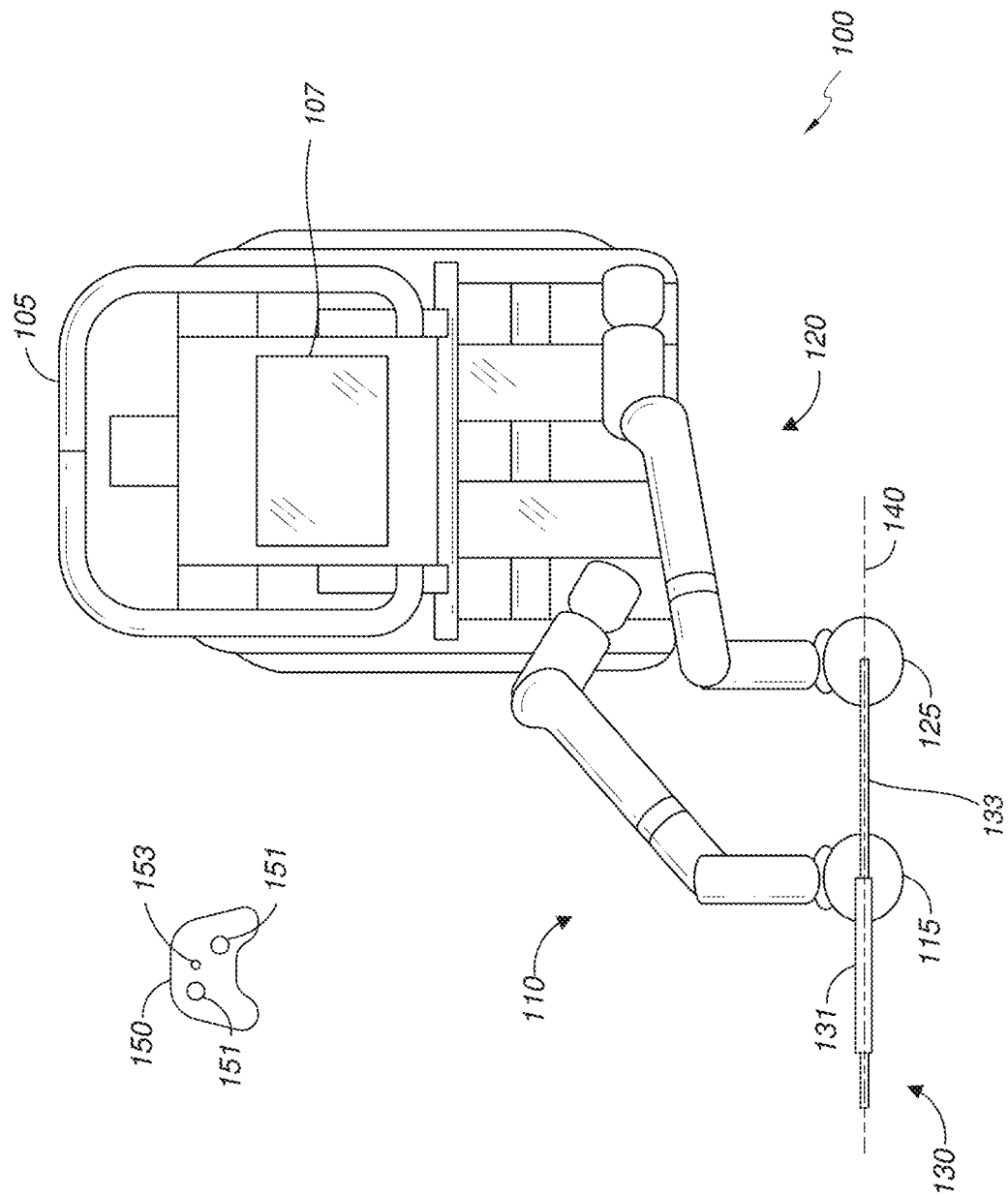
FIG. 16 illustrates an embodiment of a surgical robotic system which may be configured to drive a medical instrument having outer and inner bodies in accordance with aspects of this disclosure.

FIG. 16 illustrates an embodiment of a surgical robotic system which may be configured to drive a medical instrument having outer and inner bodies in accordance with aspects of this disclosure. Although FIG. 16 is directed to an embodiment in which the robotic arm(s) and/or instrument manipulators are attached to a cart, this disclosure is not limited thereto, and the techniques described herein are be applicable robotic arm(s) and/or instrument manipulators which may be attached to a column supporting a patient platform as shown in FIG. 6.

Returning to FIG. 16, illustrated is a system 100 that may include a cart 105, one or more instrument manipulators 115 and 125, and a medical instrument 130. The cart 105 may include a processor (not illustrated), a memory (not illustrated), a display 107 configured to render encoded data related to the navigation and/or driving of the medical instrument 130, and a set of one or more user input devices 150 (e.g., a pendant, master controller, or other user input controller). However, depending on the embodiment, one or more of the processor, the memory, and the display 107 may be located on or within another device, such as on the moveable tower 30 illustrated in FIG. 1. Additionally, in other implementations, a feedback device other than the display 107 may be used in place of, or in addition to, the display 107. Other feedback devices which may be employed include haptic devices, speakers, force-feedback actuated via one or more of the instrument manipulators 115 and 125, one or more light-emitting diode(s) LED(s), etc.

In certain implementations, the one or more user input devices 150 includes one or more joysticks 151 and a toggle input 153 (such as a button). The one or more joystick may function as inputs that can be used to generate commands for insertion and/or retraction of the medical instrument and articulation of an articulating portion of the medical instrument 130. The toggle input 153 may be used by the system to generate a change drive mode command (e.g., a toggle drive mode command) to change between various drive modes of the medical instrument 130. Further detail regarding the drive modes and the conditions for changing or toggling between the drive modes will be provided below.

The instrument manipulators 115 and 125 may include a first instrument manipulator and a second instrument manipulator 125, respectively driven by a first robotic arm 110 and a second robotic arm 120. However, aspects of this disclosure are also applicable to system having one or more instrument manipulators 115 and 125 which may be driven by other actuating mechanism(s) other than the first and second robotic arms 110 and 120. As used herein, the term instrument manipulator (also referred to as an instrument device manipulator (IDM)) may generally refer to an assembly providing a detectable connection to a medical instrument (or a portion thereof). IDMs (such as the drive unit 63 illustrated in FIG. 12) may be configured to control the movement and/or manipulation of the medical instrument, including any end effectors attached thereto. The first instrument manipulator 115 may be connected to a distal end of the first robotic arm 110 and the second instrument manipulator may be connected to a distal end of the second robotic arm 120. By actuating motor(s) of the first robotic arm 110, the motor(s) may be operable to adjust the posture or pose of the first robotic arm 110, and thus the instrument manipulator 115 (e.g., by adjusting the position and/or orientation of one or more joints 113 of the first arm) and thereby control a steerable instrument 130 attached to the instrument manipulator 115. Similar to the first robotic arm 110, the second robotic arm 120 may be operable to drive the second instrument manipulator 125 to operate the steerable instrument 130.

The medical instrument 130 in the FIG. 16 embodiment comprises an outer body 131 attached to the first instrument manipulator 115 and an inner body 133 attached to the second instrument manipulator 125 120. However, the illustrated example in FIG. 16 is merely one example medical instrument 130 and other embodiments may include a medical instrument 130 that is controlled by a single instrument manipulator 115 or a medical instrument 130 that requires three or more instrument manipulators for operation. Depending on the embodiment and the medical procedure being performed, each of the first and second medical instruments may comprise one of an inner leader portion, an outer sheath portion, a needle, forceps, a brush, etc.

The outer and inner bodies 131 and 133 may be configured to be advanced/inserted into (or retracted from) a patient along a first axis 140. As discussed above, the first axis 140 may be termed a virtual rail. The virtual rail may be defined by the axis of alignment of the instrument manipulators 115 and 125, and thus, may also be coincident with a central axis of the medical instrument 130. Movement of the first and second instrument manipulators 115 and 125 along the virtual rail 140 may control the advancing and retracting of the outer and inner bodies 131 and 133 into and out of the patient.

In one embodiment, one of the joysticks 151 is used to control articulation of the medical instrument 130, including one or more of the inner and outer bodies 131 and 133 another one of the joysticks 151 is used to control articulation of the medical instrument 130, including one or more of the inner and outer bodies 131. Depending on the drive mode, the input(s) received from the joysticks 151 may be mapped to both the inner and out bodies 131 and 133, or may be mapped to only one of the inner and out bodies 131 and 133 at a time.

A. Example Medical Instrument and Driving Modes.

Figure 17A:
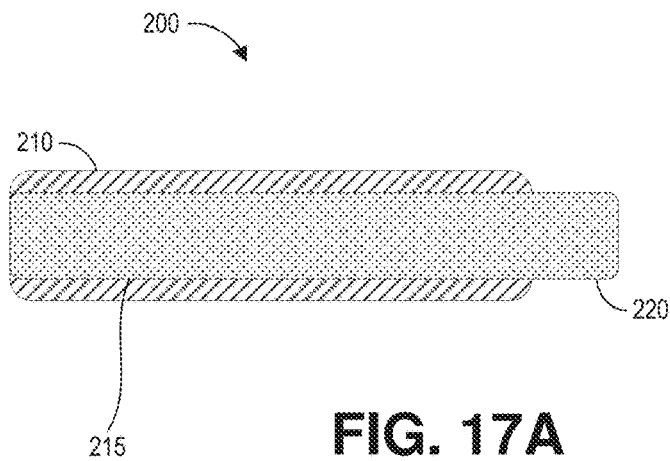
FIG. 17A depicts an embodiment of a medical instrument in accordance with aspects of this disclosure.

FIG. 17A depicts an embodiment of a medical instrument in accordance with aspects of this disclosure. The illustrated medical instrument 200 includes an outer body 210 (also referred to as a sheath) and an inner body 220 (also referred to as a leader). In certain implementations, a robotic surgical system may comprise a set of one or more robotic arm assemblies configured to control movement of the outer and inner bodies. For example, the outer body 210 and the inner body 220 may be respectively coupled to instrument manipulators connected to robotic arms (see, for example, FIG. 16). Accordingly, the outer and inner bodies 210 and 220 may be independently driven via the manipulation of the corresponding robotic arms and the instrument manipulators connected thereto. The outer body 210 may further define a lumen 215 through which the inner body 220 is configured to be driven.

Figure 17B:
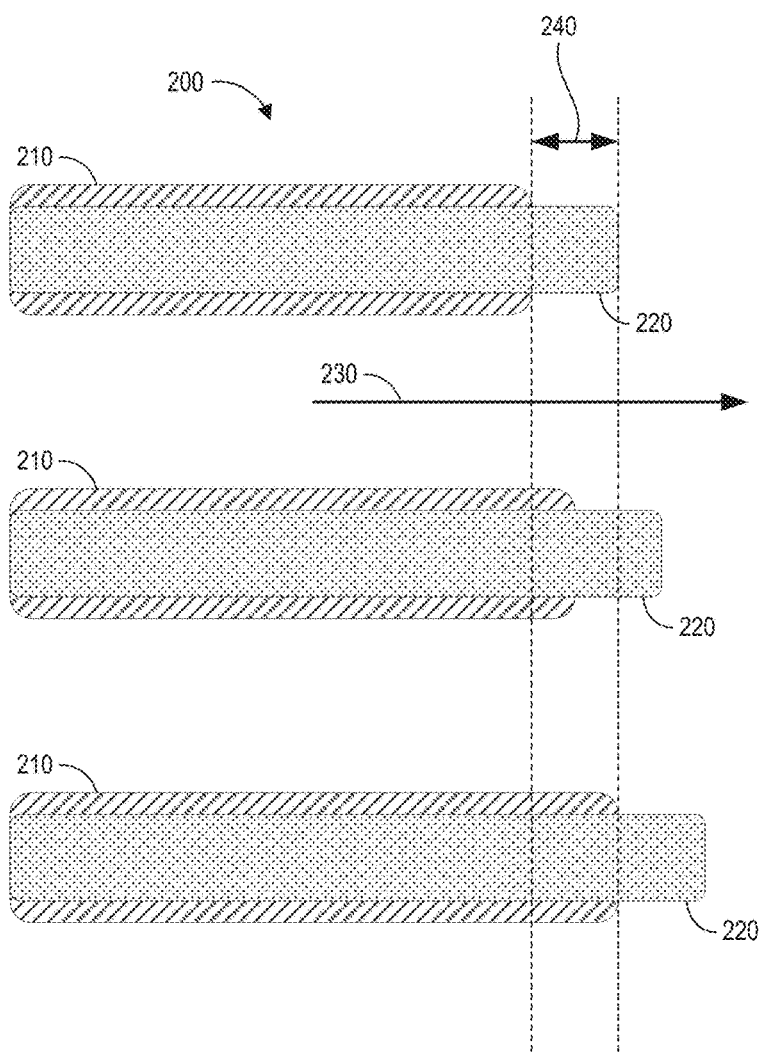
FIG. 17B illustrates an embodiment of a paired drive mode for a medical instrument in accordance with aspects of this disclosure.

FIG. 17B illustrates an embodiment of a paired drive mode for a medical instrument in accordance with aspects of this disclosure. The system may be configured to drive the medical instrument in one of a plurality of drive modes, which may include a paired drive mode and at least one unpaired drive mode.

Figure 18:
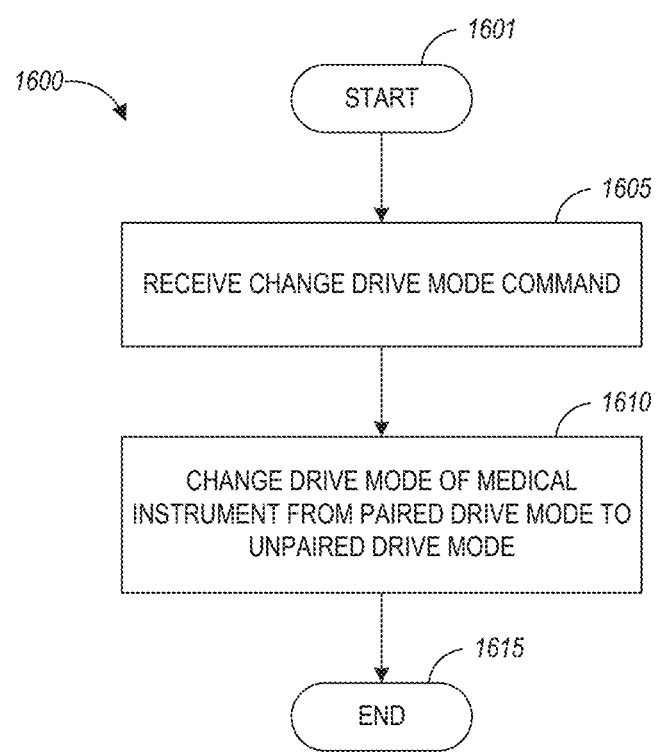
FIG. 18 is a flowchart illustrating an example method operable by a surgical robotic system, or component(s) thereof, for changing the drive mode of a medical instrument in accordance with aspects of this disclosure.

FIG. 18 is a flowchart illustrating an example method operable by a surgical robotic system, or component(s) thereof, for changing the drive mode of a medical instrument in accordance with aspects of this disclosure. For example, the steps of method 1600 illustrated in FIG. 18 may be performed by a processor of a surgical robotic system. For convenience, the method 1600 is described as performed by the processor of the system.

The method 1600 begins at block 1601. The processor may be included as a part of a system, including a medical instrument comprising an outer body and an inner body configured to be driven through a lumen in the outer body, a set of one or more instrument manipulators (e.g., which may be coupled to robotic arm assemblies) configured to control movement of the outer and inner bodies, a set of one or more user input devices, a set of one or more processors, and at least one computer-readable memory in communication with the set of processors and having stored thereon computer-executable instructions to cause the set of processors to perform the method 1600.

At block 1605 the processor receives, via a user input device (e.g., the user input device 150 of FIG. 16), a change drive mode command. The system may further be configured to, in response to receiving the change drive mode command, change a drive mode of the medical instrument 200 from the paired drive mode to the unpaired drive mode. Thus, at block 1610, in response to receiving the change drive mode command, the processor changes a drive mode of the medical instrument from a paired drive mode to an unpaired drive mode in which a distance between a distal end of the inner body and a distal end of the outer body is maintained at a predetermined distance in response to receiving a drive command from the set of input devices while in the paired drive mode. The method 1600 ends at block 1615.

With continued reference to FIGS. 16, 17A, and 17B, in certain implementations, in the paired drive mode a distance between a distal end of the inner body 220 and a distal end of the outer body 210 is maintained at a predetermined distance 240. The predetermined distance 240 between the distal ends of the outer and inner bodies 210, 220 may be maintained in response to receiving a drive command from the set of input devices. The drive command may include one or more commands to manipulate medical instrument. For example, the drive command may comprise one or more of: an insertion command (e.g., to advance or retract the medical instrument) and/or an articulation command (e.g., to increase or decrease the bending or articulation of the distal end of the medical instrument). It is to be appreciated that the term "distance," as used herein, may refer to a single length (e.g., 5 mm) or a range of lengths (5 mm-8 mm).

Referring again to FIG. 17B, a number of snapshots of medical instrument 200 are shown in sequence from top to bottom as the medical instrument 200 is inserted along an insertion direction 230. Dashed lines are provided with respect to the initial position of the predetermined distance 240 between the distal ends of the outer and inner bodies 210 and 220. As the medical instrument 200 is advanced in the illustrated snapshots, the predetermined distance 240 is maintained between the distal ends of the outer and inner bodies 210 and 220. In the paired driving mode, the predetermined distance 240 may also be maintained for other manipulation commands. For example, the predetermined distance 240 may be maintained in response to a retraction command and in response to an articulation command.

As illustrated in FIGS. 17A and 17B, the distal ends of the inner body 220 and the outer 210 body may be chamfered. These chamfered edges may allow the distal ends of the inner body 220 and the outer 210 body to more easily advance through the luminal network during a medical procedure. Additionally, when the inner body 220 includes chamfered edges, there may be certain advantages to maintain the predetermined distance 240 such that the distal end of the inner body 220 extends from the distal end of the outer body 210. For example, the chamfer on each of the distal ends the outer and inner bodies 210 and 220 may allow the distal ends to more easily advance along the luminal network without being caught on features of the walls of the luminal network. If the distal end of the inner body 220 is not extended from the distal end of the outer body 210, the advantages associated with the chamfer on the distal end of the inner body 220 cannot be taken advantage of.

The predetermined distance 240 may be selected based on one or more considerations of the physical structure of the medical instrument 240 and/or the robotic arms. For example, the length of each of the outer and inner bodies 210 and 220 may have a certain amount of manufacturing variation, which may lead to the distance between the distal ends of the outer and inner bodies 210 and 220 being offset from a corresponding distance between distal ends of outer and inner bodies that do not have such manufacturing variations. The lengths of the outer and inner bodies 210 and 200 may also change over time, for example, shrinking in length, which may result in a difference between the distance between the distal ends of the outer and inner bodies 210 and 220 as calculated by the system and the distance between the distal ends in practice.

Additionally, when the distance between distal ends of the outer and inner bodies 210 and 220 is less than a threshold distance, the image data captured by a camera formed on the distal end of the inner body may be occluded by the outer body 210, which may be visible in the images captured by the camera. Thus, it may be desirable to extend the distal end of the inner body 220 from the distal end of the outer body 210 such that distal end of the outer body 220 is not visible in the captured images.

Accordingly, the predetermined distance 240 may be selected to be greater than the tolerance for such manufacturing differences in length such that the distal end of the inner body 210 will extend from the distal end of the outer body 220 when loaded onto the instrument manipulators of the robotic arms. In other implementations, the predetermined distance 240 may also be selected to account for any differences in the positioning of the instrument manipulators from the commanded positioning, which may have a tolerance error for positioning. Thus, the predetermined distance 240 may also account for differences introduced into the distance between the distal ends of the outer and inner bodies 210 and 220 due to differences in positioning of the instrument manipulators and the commanded positions.

Another consideration which may be used to select the predetermined distance 240 may include a distance between the distal ends of the outer and inner bodies 210 and 220 beyond which insertion of the medical instrument 200 may be hindered. For example, as discussed below, the outer and inner bodies 210 and 220 may be articulated together to provide more articulation than achievable by one of the bodies 210 and 200 alone. As used herein, the cooperative articulation of the outer and inner bodies 210 and 220 in the same direction may be generally referred to as "co-articulation." When the distal end of the inner body 220 extends too far from the distal end of the outer body 210, the co-articulation of the medical instrument 200 may cause an undesirable sweeping motion, which may be difficult for a user to manipulate effectively. Accordingly, the predetermined distance 240 may be selected to be less than a threshold at which co-articulation results in an undesirable sweeping motion.

In certain embodiments, the distal end of the inner body 220 may be retracted into the outer body 210 such that the distance between the distal ends of the outer and inner bodies 210 and 220 is maintained at a predetermined distance. By maintaining the distal end of the inner body 220 within the lumen defined in the outer body 210, wear on the inner body 220 may be reduced, thereby increasing the life of the inner body 220. In certain implementations, it may be desirable to drive the medical instrument 200 with the distal end of the inner body 220 retracted into the outer body 210. For example, when the inner body 220 comprises a sharp edge, such as a needle, driving with the inner body 220 extending from the outer body 210 may cause inadvertent damage to the patient. When driving with the inner body 220 retracted, the medical instrument 200 may experience less sweeping during articulation, may having a tighter turn radius, and may protect the distal end of the inner body 220. However, this retracted driving may also result in occlusion of the field of view of a camera positioned on the distal end of the inner body 220. Further, a tighter turn radius may result in premature damage to the inner body 220.

The predetermined distance 240 which can be maintained between the distal ends of the outer and inner bodies 210 and 220 while driving in the paired mode may comprise a range of distances. For example, range of distances may be selected based on the above discussed considerations affecting the driving of the medical instrument 200 in the paired mode such that driving the medical instrument 200 does not suffer from the adverse effects associated with too small of a distance between the distal ends or too great of a distance between the distal ends. The system may monitor the distance between the distal ends of the outer and inner bodies 210 and 220 during driving in the paired mode, and adjust the distance therebetween in response to the measured distance being less than a first threshold distance or greater than a second threshold distance. By maintaining the distance between the distal ends within the range of distances, the system may be able to compensate for measurement errors, which may be introduced due to errors in the instrument manipulators positions, extension or contraction of one or more of the outer and inner bodies 210 and 220 during or prior to the procedure, etc.

In certain embodiments, the system may store a plurality of predetermined distances from which a particular predetermined distance may be selected for driving in the paired mode. The predetermined distances may be associated with a user's preferences, a type of the medical procedure being performed (e.g., bronchoscopy, ureteroscopy, gastroenterology, etc.), and/or each individual medical instrument. The system may receive a selection identifying a preference for a value of the predetermined distance. The selection may include an identification of a user of the system and the identified user may be associated with a given predetermined distances preselected according to the user's preferences. The system may adjust the predetermined distance based on the received selection. For example, the system may have various modes, such as a sport mode or conservative mode, to allow different performance profiles to be selected, possibly based on user preference. Each mode may have different parameters for the predetermined distances and/or articulation factors. The predetermined distances and co-articulation factors can impact the articulation profiles and, conversely, the wear and tear on the medical device.

In certain embodiments, the system may adjust the predetermined distance based on a location of the distal end of the outer body with respect to a luminal network of a patient when the drive mode of the medical instrument is changed from the paired drive mode to the unpaired drive mode or vise-versa. Changing the predetermined distance and co-articulation factor to achieve articulation profiles can be desirable for a given anatomy.

In maintaining the predetermined distance between the distal ends of the outer and inner bodies 210 and 220 when driving in the paired mode, the system may determine that the distance between the distal end of the inner body and the distal end of the outer body is not equal to the predetermined distance (or not within the range of distances). In certain embodiments, the system may determine the distance between the distal ends of the inner and outer bodies based on the respective lengths of the inner and outer bodies and the robot insertion data which may be used to determine to distance that the corresponding inner or outer body has been inserted into the patient. In one implementation, system may store the lengths of the inner and outer bodies in a memory device, which may be installed on a portion of the inner and outer bodies. For example, an RFID tag may be installed into each of the inner and outer bodies and the system may be configured to read the lengths of the inner and outer bodies from the RFID tags. The lengths of the inner and outer bodies may be measured after manufacturing and the measured values may be stored in the memory device.

The system may, in response to determining that the distance between the distal end of the inner body and the distal end of the outer is not equal to the predetermined distance, advance or retract one of the outer and inner bodies until the distance between the distal end of the inner body and the distal end of the outer body is maintained at the predetermined distance. For example, the system may transition into an outer body drive mode to advance the outer body 210 or may transition into an inner body drive mode to retract the inner body 220 until the distance is substantially equal to (e.g., within a defined tolerance range of) the predetermined distance. The system may transition back in the paired mode so as to drive, via the set of instrument manipulators, both the outer and inner bodies to maintain the predetermined distance in response to bringing the distance back within the tolerance range of the predetermined distance.

In particular, the system may determine that the distal end of the inner body extends from the distal end of the outer body by less than the predetermined distance, and in response to determining that the distal end of the inner body extends from a distal end of the outer by less than the predetermined distance, change the drive mode of the medical instrument into an inner body drive mode and advance, based on an insertion command received from a user, the inner body until the distal end of the inner body extends from the distal end of the outer body the predetermined distance. The system may then change the drive mode into the paired drive mode. Alternatively, the system may determine that the distal end of the inner body extends from the distal end of the outer body by greater than the predetermined distance, and in response to determining that the distal end of the inner body extends from a distal end of the outer by greater than the predetermined distance, change the drive mode of the medical instrument into an outer body drive mode and advance, based on an insertion command received from a user, the outer body until the distal end of the inner body extends from the distal end of the outer body the predetermined distance. The system may then change the drive mode into the paired drive mode.

The system may further be configured to operate in an inner body drive mode (also referred to as a leader drive mode). In the inner body drive mode, the system may be configured to map input received from the user input device to drive commands to the inner body, without providing further commands to the outer body. In certain implementations, the system may be configured to receive, via a set of user input devices, an inner body drive mode command and, in response to receiving the inner body drive mode command, change the drive mode of the medical instrument to an inner body drive mode in which the inner body is advanced or retracted while the outer body remains stationary. The inner body drive mode may also map articulation commands to the inner body. In certain embodiments, the system may also articulate the outer body in the inner body drive mode. Techniques used for mapping articulation commands to the inner and outer bodies depending on the drive mode will be discussed in greater detail below.

Figure 19:
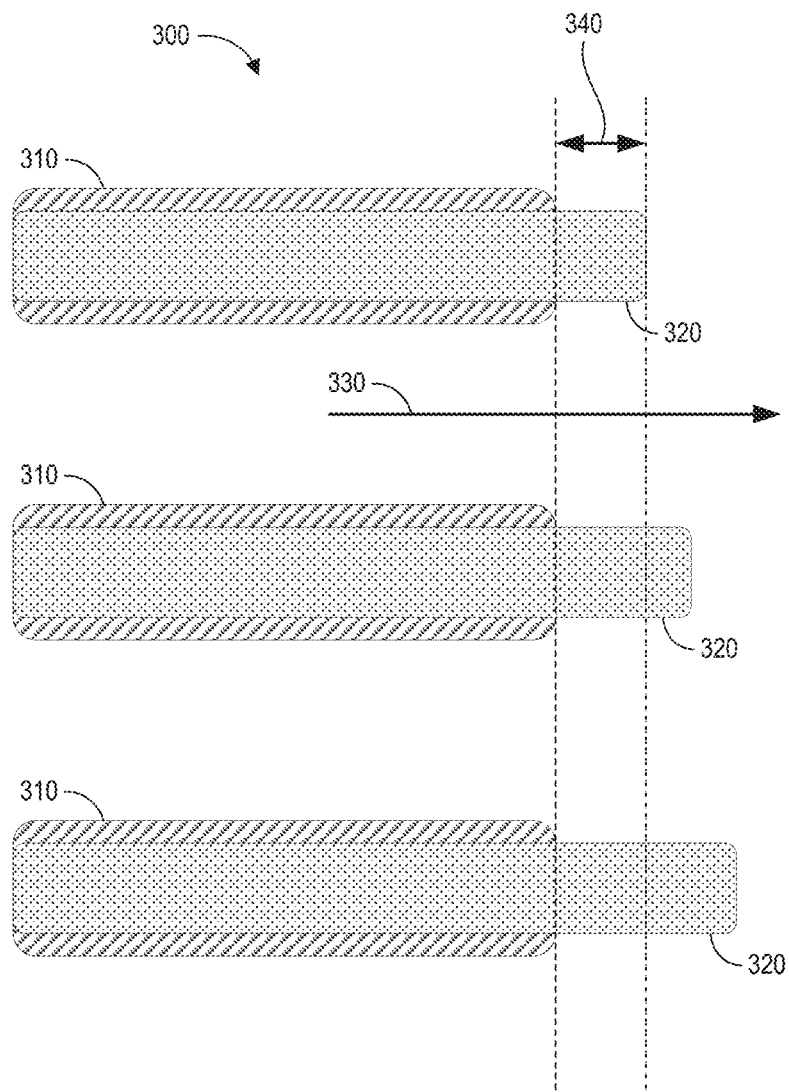
FIG. 19 illustrates an embodiment of an inner body drive mode for a medical instrument in accordance with aspects of this disclosure.

FIG. 19 illustrates an embodiment of an inner body drive mode for a medical instrument in accordance with aspects of this disclosure. The system may be configured to receive, via a user input device, an inner body drive mode command. The system may further be configured to, in response to receiving the inner body drive mode command, change the drive mode of the medical instrument 300 to the inner body drive mode. In the inner body drive mode, insertion and retraction commands may be mapped to the inner body while the outer body remains substantially stationary.

In FIG. 19, a number of snapshots of medical instrument 300 are shown in sequence from top to bottom as the inner body 320 is inserted along an insertion direction 330 while the position of the outer body 310 is substantially maintained. Dashed lines are provided with respect to the initial position of the predetermined distance 340 between the distal ends of the outer and inner bodies 310 and 320. For example, when switching to the inner body drive mode from the paired drive mode, the distal ends of the outer and inner bodies 310 and 320 may be initially separated by a distance within a threshold range of the predetermined distance 340. As the inner body 320 is advanced in the illustrated snapshots in response to an advance command, the outer body 310 remains substantially stationary. Although the position of the distal end of the outer body 310 is illustrated as being stationary, changes in the environment (e.g., breathing motion of the patient) and/or forces exerted on the outer body 310 due to the movement of the inner body 320 may result in the position of the outer body 310 being minimally changed. Although an advance command is illustrated in FIG. 19, a retract command may also be performed in the inner body drive mode in which the inner body 320 is retracted towards the distal end of the outer body 310, while the outer body remains 310 substantially stationary.

The system may further be configured to operate in an outer body drive mode (also referred to as a sheath drive mode). In the outer body drive mode, the system may be configured to map input received from the user input device to drive commands to the outer body, without providing further commands to the inner body. In certain implementations, the system may be configured to receive, via a set of user input devices, an outer body drive mode command and, in response to receiving the outer body drive mode command, change the drive mode of the medical instrument to an outer body drive mode in which the outer body is advanced or retracted while the inner body remains stationary. The outer body drive mode may also map articulation commands to the inner body, as is discussed in detail below.

Figure 20:
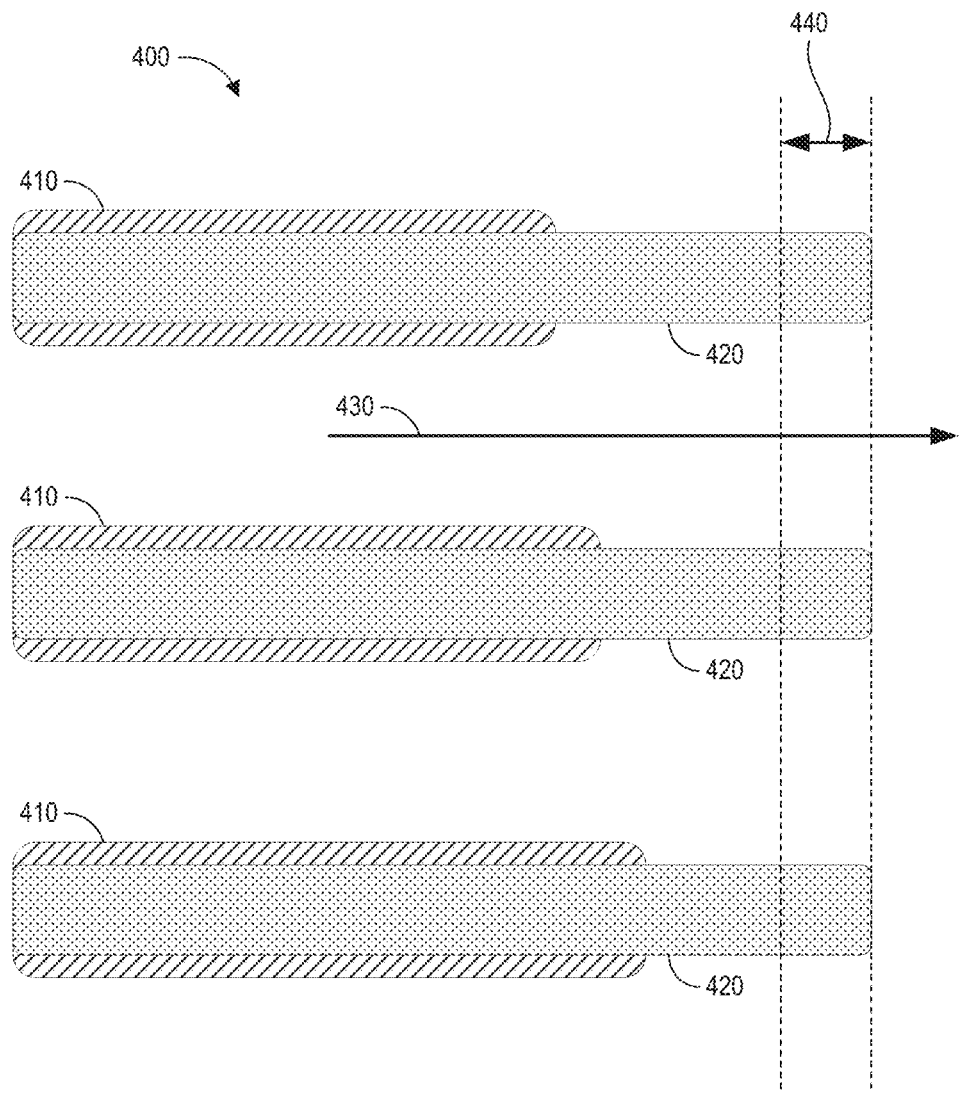
FIG. 20 illustrates an embodiment of an outer body drive mode for a medical instrument in accordance with aspects of this disclosure.

FIG. 20 illustrates an embodiment of an outer body drive mode for a medical instrument in accordance with aspects of this disclosure. The system may be configured to receive, via a user input device, an outer body drive mode command.

The system may further be configured to, in response to receiving the outer body drive mode command, change the drive mode of the medical instrument 300 to the outer body drive mode. In the outer body drive mode, insertion and retraction commands may be mapped to the outer body while the inner body remains substantially stationary.

In FIG. 20, a number of snapshots of medical instrument 400 are shown in sequence from top to bottom as the outer body 410 is advanced along an insertion direction 430 while the position of the inner body 420 is substantially maintained. Dashed lines are provided with respect to a position of the predetermined distance 440 between the distal ends of the outer and inner bodies 410 and 420 at which further advancing of the outer body 410 would automatically switch into paired mode. As the distal end of the outer body 410 is advanced in the illustrated snapshots in response to an advance command, the inner body 420 remains substantially stationary. Although the position of the distal end of the inner body 420 is illustrated as being stationary, changes in the environment (e.g., breathing motion of the patient) and/or forces exerted on the inner body 420 due to the movement of the outer body 410 may result in the position of the inner body 420 being minimally changed. Although an advance command is illustrated in FIG. 20, a retract command may also be performed in the outer body drive mode in which the distal end of the outer body 410 is retracted away from the distal end of the inner body 420, while the inner body 420 remains substantially stationary.

Figure 21:
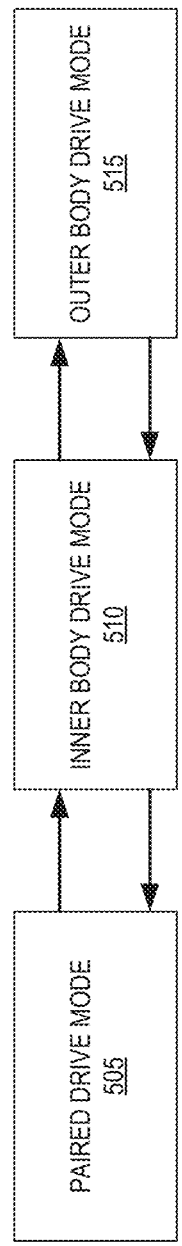
FIG. 21 provides a block diagram which illustrates a technique for changing the drive mode of a medical instrument in accordance with aspects of this disclosure.

FIG. 21 provides a block diagram which illustrates a technique for changing the drive mode of a medical instrument in accordance with aspects of this disclosure. In the illustrated embodiment, the medical instrument may be driven in one of a paired drive mode 505, an inner body drive mode 510, and an outer body drive mode 515. In certain implementations, the user input device may comprise a button configured to receive a command from a user of the system to change the current drive mode. The system may respond to the change drive mode command differently depending on the current state of the system. For example, when the system is driving the medical instrument in a paired drive mode 505 command and receives a change drive mode command, the system may change the drive mode into the inner body drive mode 510. This change may involve parking the sheath and initiating driving of the inner body.

When in the inner body drive mode 510, the system's response to receipt of a change drive mode command may depend on whether the distance between the distal ends of the inner body and the outer body is within a threshold distance of the predetermined distance (e.g., the medical instrument is in a paired position, see FIG. 17A). When the distance between the distal ends of the inner body and the outer body is within a threshold distance of the predetermined distance, the system may change the drive mode to the paired drive mode 505 in response to receiving a change drive mode command. When the distance between the distal ends of the inner body and the outer body is not within a threshold distance of the predetermined distance, the system may change the drive mode to the outer body drive mode 515 in response to receiving a change drive mode command.

Finally, when in the outer body drive mode 515, the system may change the drive mode into the inner body drive mode 510 in response to receiving a change drive mode command. This change in drive mode may involve parking the outer body at the outer body's current position and initiating driving of the inner body. The system may not require a command to transition directly from the outer body drive mode 515 to the paired drive mode 505 since, as discussed below, the system may automatically make this change in drive modes under certain conditions.

In certain embodiments, the system may be configured to drive the medical instrument at a greater speed in the paired drive mode 505 than in either of the inner body drive mode 510 or the outer body drive mode 515. For example, driving of the medical instrument through the initial portion of the luminal network closer to the access point may require less precision than a portion of the luminal network near the target at which the user may select the inner body or outer body drive modes 510 or 515. Accordingly, the system may drive the medical instrument at a greater speed in paired drive mode 505 when less precision is required. Alternatively, the system may drive the medical instrument at a greater speed when within a threshold insertion distance from the access point and limit the speed after the insertion distance is greater than the threshold insertion distances. The speed of driving may include at least one of: an articulation speed, a relaxation speed, an insertion speed, and a retraction speed.

Figure 22:
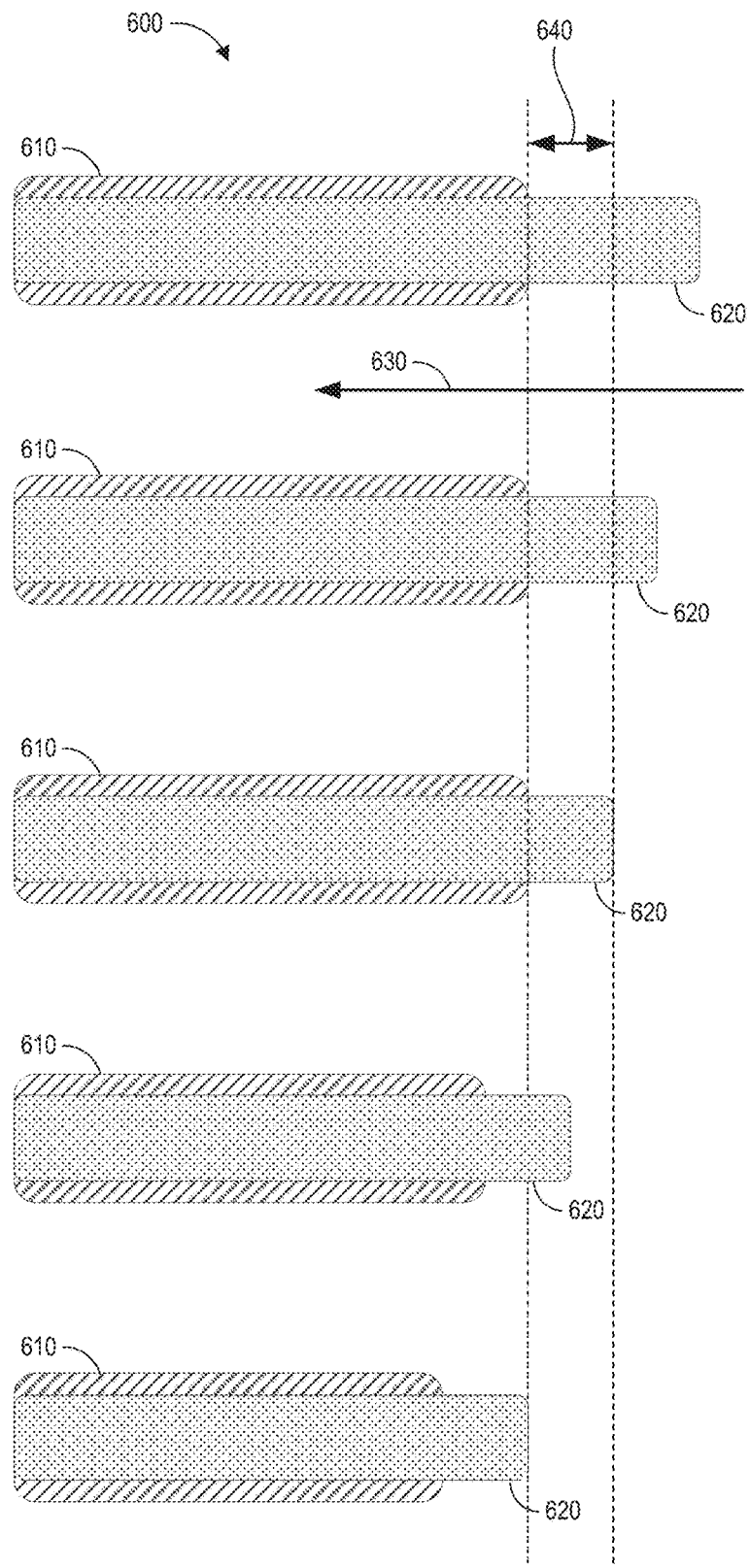
FIG. 22 illustrates an embodiment of auto-pairing for a medical instrument in accordance with aspects of this disclosure.

The system may also be configured to perform "auto-pairing" (e.g., automatically transitioning from either of the inner body drive mode 510 or the outer body drive mode 515) by changing the drive mode to the paired drive mode 505 when the driving in the current drive mode approaches the paired position. FIG. 22 illustrates an embodiment of auto-pairing for a medical instrument in accordance with aspects of this disclosure. Specifically, in FIG. 22, a number of snapshots of medical instrument 600 are shown in sequence from top to bottom as the inner body 620 is retracted along a retraction direction 630. In this case, the system is driving the inner body 620 in the inner body drive mode and the distal end of the inner body 620 extends from the distal end of the outer body 610 by a distance greater than the predetermined distance 640, illustrated with dashed lines. For example, the system may be configured to receive, via a set of user input devices in the inner body drive mode, a retraction command to retract. In response to receiving the retraction command, the system may retract the inner body 620 via the set of instrument manipulators of the robotic arm assemblies.

In certain embodiments, once the distal end of the inner body 620 reaches the predetermined distance 640 from the distal end of the outer body 610 (e.g., the medical instrument 600 is in the paired position), the system may automatically enter the paired drive mode. That is, the system may determine that the distance between the distal end of the inner body 620 and the distal end of the outer body 610 is within a tolerance range of the predetermined distance 640. In response to determining that the distance between the distal end of the inner body 620 and the distal end of the outer body 610 is within the tolerance range of the predetermined distance 640, the system may change the drive mode of the medical instrument 600 to the paired drive mode. Thereafter, further drive commands may be mapped by the system to both of the outer and inner bodies 610 and 620 according to the paired drive mode. In the example illustrated in FIG. 22, the retraction command is maintained and both of the outer and inner bodies 610 and 620 are retracted to maintain the predetermined distance 640 therebetween.

Figure 23:
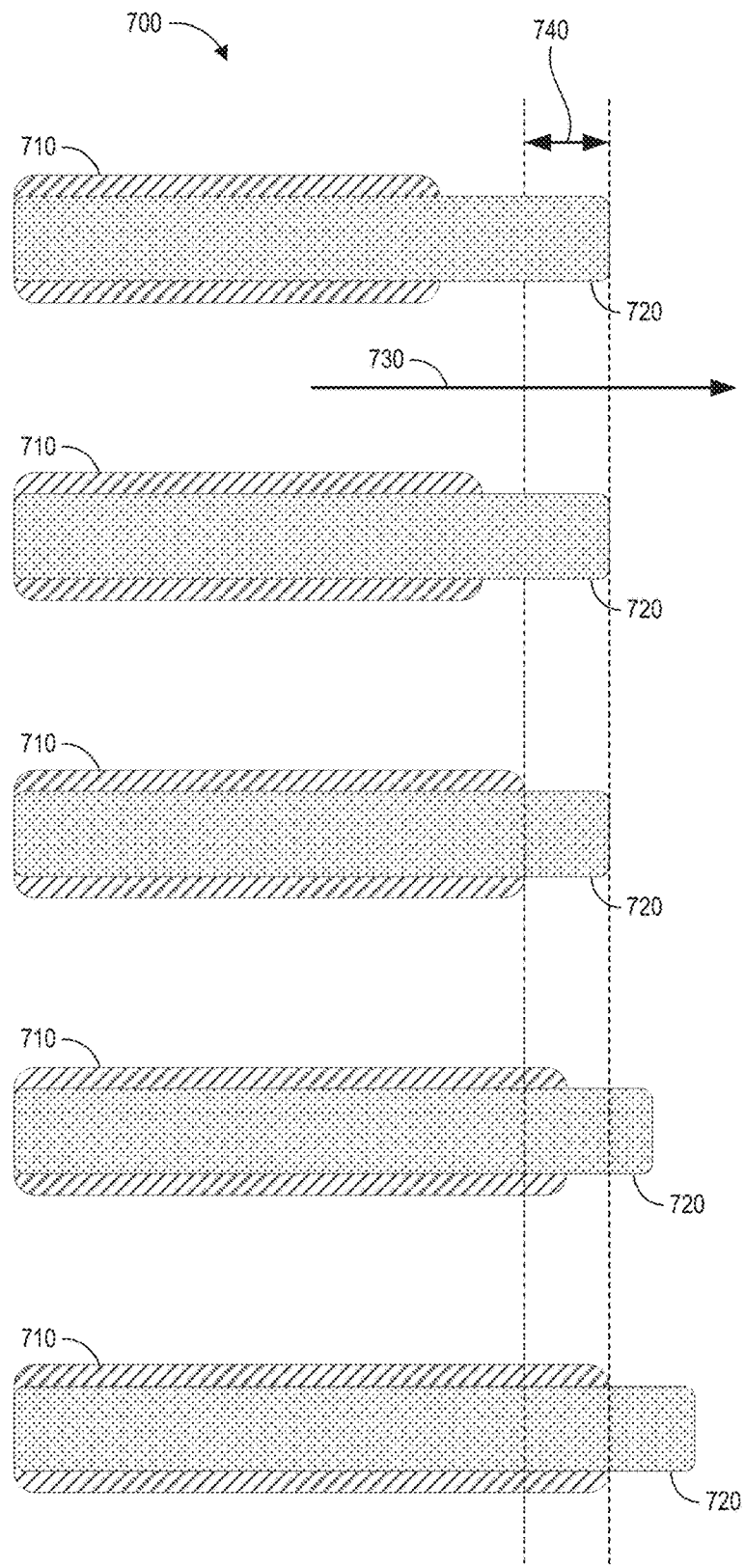
FIG. 23 illustrates another embodiment of auto-pairing for a medical instrument in accordance with aspects of this disclosure.

The system may be further configured to perform "auto-pairing" from the outer body drive mode. FIG. 23 illustrates another embodiment of auto-pairing for a medical instrument in accordance with aspects of this disclosure. Specifically, in FIG. 23, a number of snapshots of medical instrument 700 are shown in sequence from top to bottom as the outer body 710 is inserted along an insertion direction 730. In this case, the system is driving the outer body 710 in the outer body drive mode and the distal end of the inner body 720 extends from the distal end of the outer body 710 by a distance greater than the predetermined distance 740, illustrated with dashed lines. For example, the system may be configured to receive, via a set of user input devices in the outer body drive mode, an insertion command to insert. In response to receiving the insertion command, the system may insert the outer body 710 via the set of instrument manipulators of the robotic arm assemblies.

In certain embodiments, once the distal end of the outer body 710 reaches the predetermined distance 740 from the distal end of the inner body 720 (e.g., the medical instrument 700 is in the paired position), the system may automatically enter the paired drive mode. That is, the system may determine that the distance between the distal end of the inner body 720 and the distal end of the outer body 710 is within a tolerance range of the predetermined distance 740. In response to determining that the distance between the distal end of the inner body 720 and the distal end of the outer body 710 is within the tolerance range of the predetermined distance 740, the system may change the drive mode of the medical instrument 700 to the paired drive mode. Thereafter, further drive commands may be mapped by the system to both of the outer and inner bodies 710 and 720 according to the paired drive mode. In the example illustrated in FIG. 23, the insertion command is maintained and both of the outer and inner bodies 710 and 720 are inserted to maintain the predetermined distance 740 therebetween.

Figure 24:
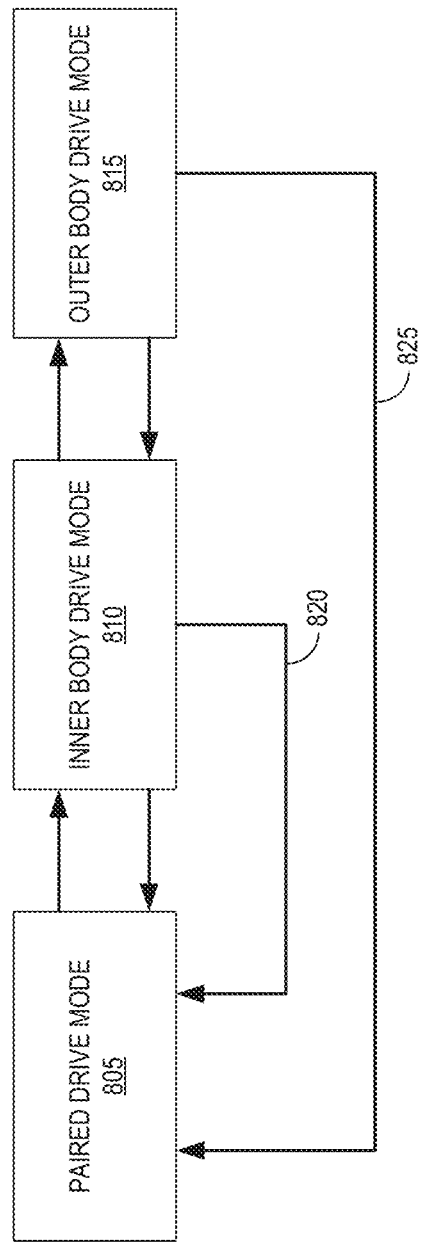
FIG. 24 provides a block diagram which illustrates another technique for changing the drive mode of a medical instrument in accordance with aspects of this disclosure.

FIG. 24 provides a block diagram which illustrates another technique for changing the drive mode of a medical instrument in accordance with aspects of this disclosure. Specifically, FIG. 24 illustrates the "auto-pairing" transitions discussed in connection with FIGS. 22 and 23 above. In a first auto-pairing technique 820, the system may automatically transition from the inner body drive mode 810 to the paired drive mode 805 in response to retracting the distal end of the inner body into the paired position (e.g., within a tolerance range of the predetermined distance). In a second auto-pairing technique 825, the system may automatically transition from the outer body drive mode 815 to the paired drive mode 805 in response to inserting the distal end of the outer body into the paired position (e.g., within a tolerance range of the predetermined distance).

In certain implementations, the system may determine whether a timing condition is satisfied when performing one of the first and second auto-pairing techniques 820 and 825. For example, when in the inner body drive mode 810, the user may retract the inner body until the distance between the distal ends of the inner and outer bodies is in the paired position. Upon reaching the paired position, the system may begin a timer or otherwise track or measure the duration in which the inner instrument has been commanded to retract since reaching the paired position. If the system received a command to stop retracting or to advance the medical instrument while the time elapsed is less than a threshold time period, the system may return to or remain in the inner body drive mode 810. Otherwise, if the time condition has been satisfied, then the system may change the drive mode to paired mode. Such time conditions may serve as a technique to prevent the system from automatically changing from one mode to the paired drive mode 805 when the user does not intend to enter the paired drive mode 805.

Similarly, the time condition can be used to determine whether an outer instrument insertion command will cause the system from transitioning from the sheath drive mode to the paired drive mode.

Figure 25:
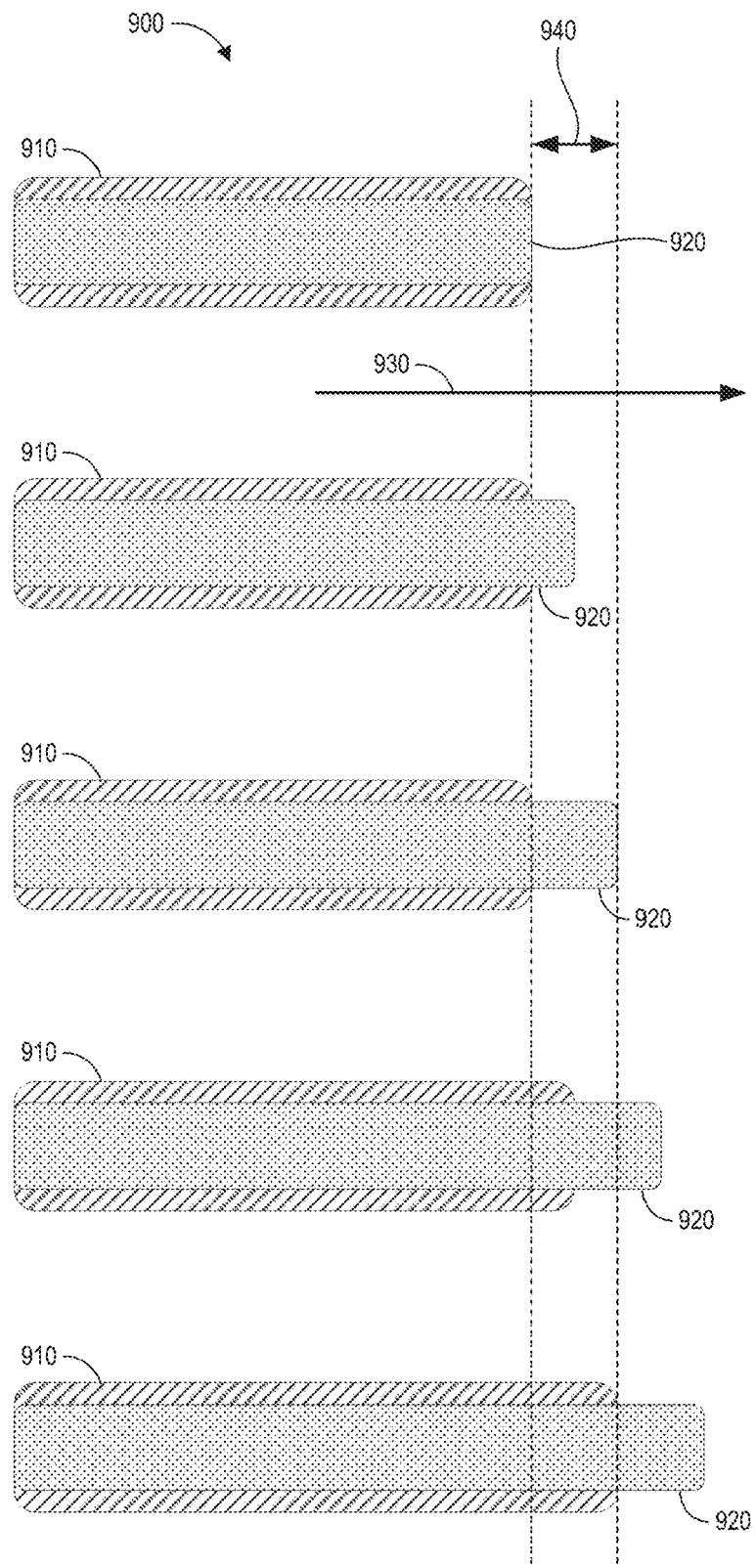
FIG. 25 illustrates an embodiment of initial catch up for a medical instrument in accordance with aspects of this disclosure.

The system may also be configured to perform initial adjustments following the start of a medical procedure to address misalignment of the distal ends of the inner body and the outer body. FIG. 25 illustrates an embodiment of initial catch up for a medical instrument in accordance with aspects of this disclosure. In certain implementations, the system may be configured to automatically start a procedure in the paired drive mode. However, after initial setup of the robotic surgical system, the distal ends of the outer and inner bodies 910 and 920 may not be positioned in the paired position (e.g., within a threshold distance of the predetermined distance 940). This may occur, for example, due to the length of each of the outer and inner bodies 910 and 920 having a certain amount of manufacturing difference, which may lead to the distance between the distal ends of the outer and inner bodies 210 and 220 being offset from the predetermined distance based on the loading position of the robotic arms. The system may store the lengths of inner and outer bodies 910 and 920 as measured after manufacturing in RFID tags respectively attached to the inner and outer bodies 910 and 920. Thus, the system may be able to read the lengths of the inner and outer bodies 910 and 920 taking into account manufacturing differences which were measured after manufacturing. One possible misalignment initial condition is illustrated in FIG. 25, in which the distance between the distal ends of the outer and inner bodies 910 and 920 is less than the predetermined distance 940.

In response to receiving an insertion command, the system may drive only the inner body 920 until the distance between the outer and inner bodies 910 and 920 reaches the predetermined distance 940. Thereafter, the system may drive the outer and inner bodies 910 and 920 together in the paired mode.

Figure 26:
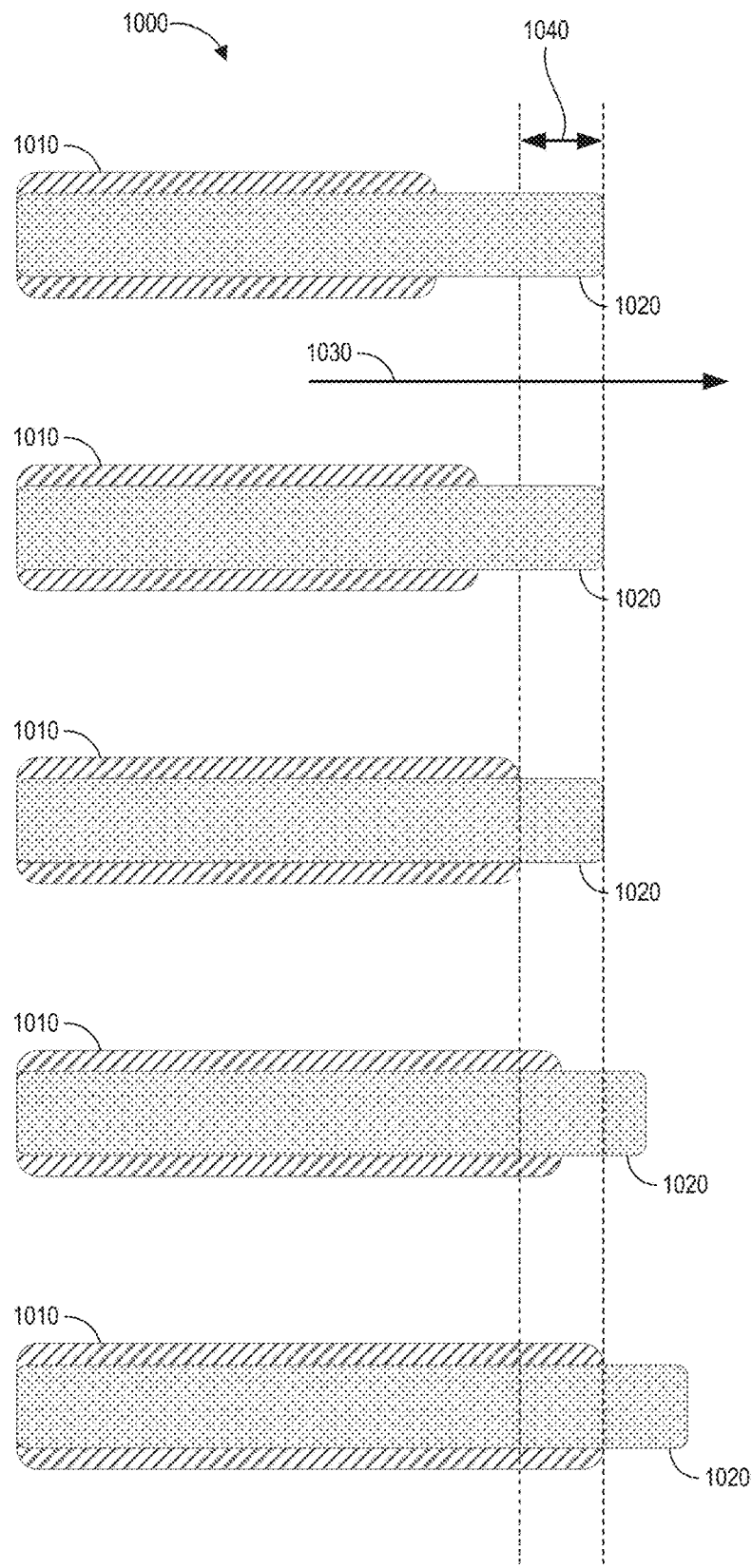
FIG. 26 illustrates another embodiment of initial catch up for a medical instrument in accordance with aspects of this disclosure.

FIG. 26 illustrates another embodiment of initial catch up for a medical instrument in accordance with aspects of this disclosure. For example, another misalignment that may occur includes the distance between the distal ends of the outer and inner bodies 1010 and 1020 being greater than the predetermined distance 1040. As described above, the system may be configured to automatically start a procedure in the paired drive mode. However, after initial setup of the robotic surgical system, the distal ends of the outer and inner bodies 1010 and 1020 may not be positioned in the paired position (e.g., within a threshold distance of the predetermined distance 940). Another possible misalignment initial condition is illustrated in FIG. 26, in which the distance between the distal ends of the outer and inner bodies 1010 and 1020 of the medical instrument 1000 is greater than the predetermined distance 1040.

In response to receiving an insertion command, the system may drive only the outer body 1010 until the distance between the outer and inner bodies 1010 and 1020 reaches the predetermined distance 1040. Thereafter, the system may drive the outer and inner bodies 1010 and 1020 together in the paired mode.

Figure 27:
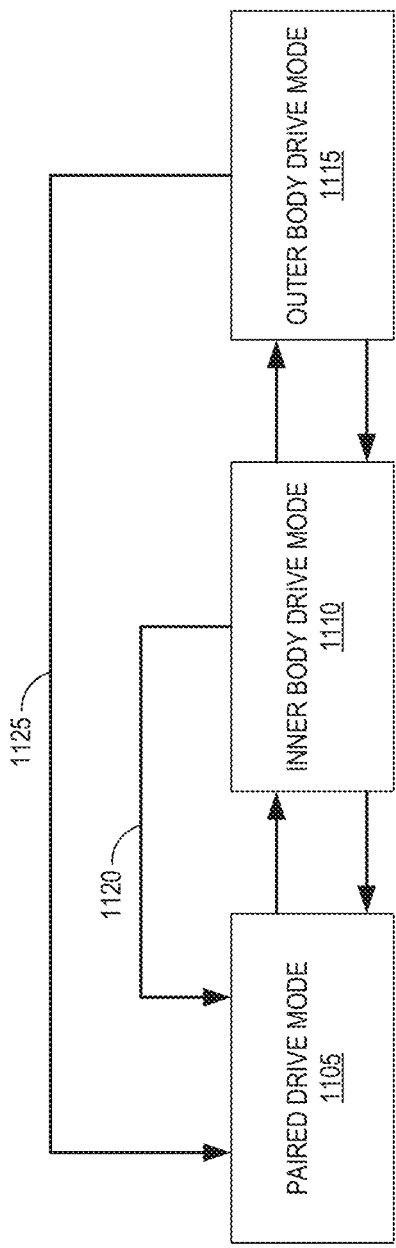
FIG. 27 provides a block diagram which illustrates yet another technique for changing the drive mode of a medical instrument in accordance with aspects of this disclosure.

FIG. 27 provides a block diagram which illustrates yet another technique for changing the drive mode of a medical instrument in accordance with aspects of this disclosure. Specifically, FIG. 27 illustrates the "initial catch-up" transitions discussed in connection with FIGS. 25 and 26 above. In a first initial catch-up technique 1120, the system may automatically transition from the inner body drive mode 1110 to the paired drive mode 1105 in response to the distance between the distal ends of the outer and inner bodies and being less than the predetermined distance. In a second initial catch-up technique 1125, the system may automatically transition from the outer body drive mode 1115 to the paired drive mode 1105 in response to the distance between the distal ends of the outer and inner bodies and of the medical instrument being greater than the predetermined distance.

B. Co-Articulation Between Medical Instrument Bodies.

In order to advance through a patient's luminal network, it may be necessary for a portion of the medical instrument, near the distal end, to articulate so as to adjust the insertion direction of the medical instrument along a desired lumen in the luminal network. When the system is configured to drive the medical instrument in various drive modes (e.g., the paired drive mode, the inner body drive mode, and the outer body drive mode), the system may map articulation commands received via the set of one or more user input devices based on the current drive mode.

Figure 28:
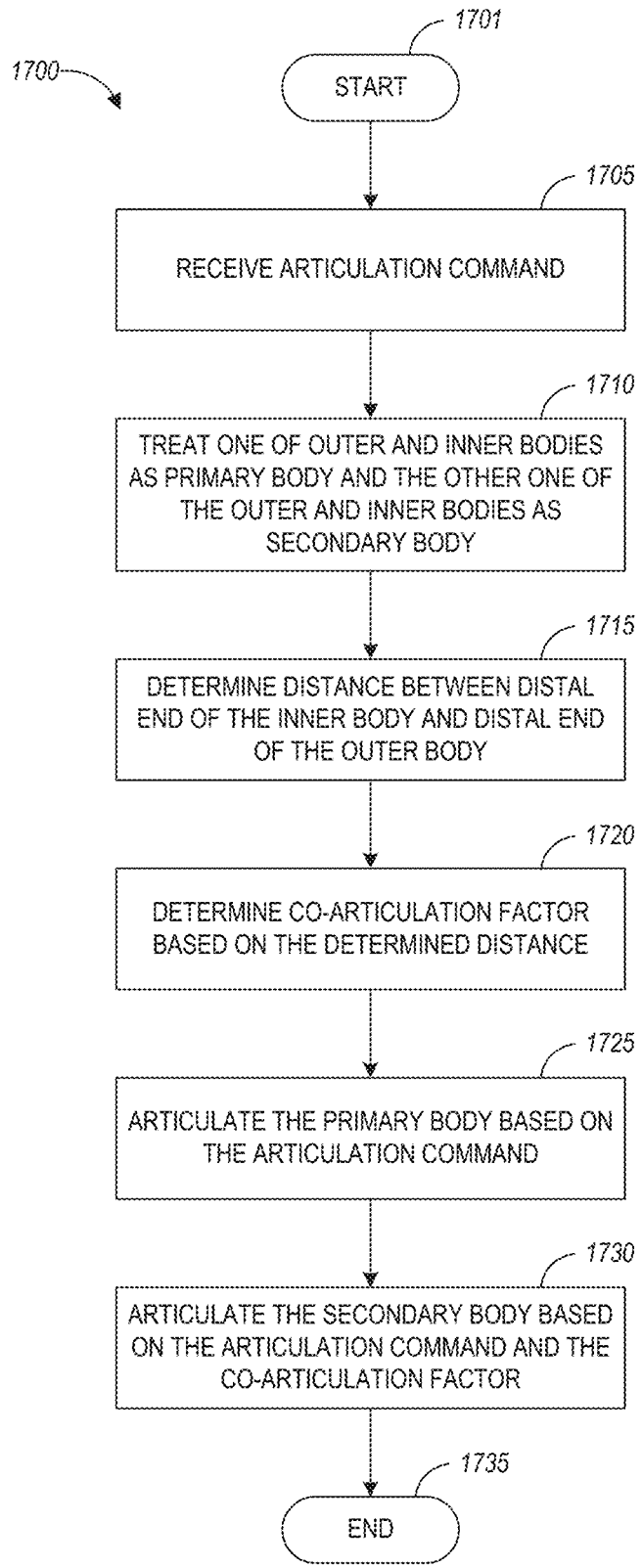
FIG. 28 is a flowchart illustrating an example method operable by a surgical robotic system, or component(s) thereof, for co-articulating the outer and inner bodies of a medical instrument in accordance with aspects of this disclosure.

FIG. 28 is a flowchart illustrating an example method operable by a surgical robotic system, or component(s) thereof, for co-articulating the outer and inner bodies of a medical instrument in accordance with aspects of this disclosure. For example, the steps of method 1700 illustrated in FIG. 28 may be performed by a processor of a surgical robotic system. For convenience, the method 1700 is described as performed by the processor of the system.

The method 1700 begins at block 1701. The processor may be included as a part of a system, including a medical instrument comprising an outer body and an inner body configured to be driven through a lumen in the outer body, a set of one or more instrument manipulators (e.g., coupled to robotic arm assemblies) configured to control movement of the outer and inner bodies, a set of one or more user input devices, a set of one or more processors, and at least one computer-readable memory in communication with the set of processors and having stored thereon computer-executable instructions to cause the set of processors to perform the method 1700.

At block 1705, the processor receives, via a set of user input devices, an articulation command to articulate the medical instrument. In certain embodiments, the articulation command may not include an selection of the outer or inner body of the medical instrument for articulation. Accordingly, the system may be configured to map the articulation command to one or both of the outer and inner bodies based on the current drive mode. For example, when in the inner body drive mode, the user may wish to articulate the distal end of the inner body. However, depending on the distance between the distal ends of the inner and outer bodies, it may be desirable to articulate both of the inner and outer bodies, to provide additional articulation (e.g., a smaller radius of curvature) or to avoid the articulation of the inner and outer bodies from counteracting each other.

One potential issue which may arise when articulating only one of the outer and inner bodies at a time is "muscling." As used herein, muscling generally refers to a situation in which the articulation applied to one of the outer and inner bodies opposes the articulation in the other body. This may occur, for example, when a first force is applied to a tendon in the outer body to maintain the current articulation of the outer body, while a second force is applied to the inner body in response to an articulation command. Accordingly, muscling may occur between the first and second forces result in opposing forces being generated between the outer and inner bodies.

To prevent undesirable muscling and to improve the amount of articulation achievable by the medical instrument, the system may "co-articulate" the outer and inner bodies in response to receiving an articulation command. In certain implementations, the amount of co-articulation may depend on the distance between the distal ends of the outer and inner bodies and may also depend on the current drive mode. In the method 1700 of FIG. 28, at block 1701, the processor treats one of the outer and inner bodies as a primary body and the other one of the outer and inner bodies as a secondary body. The system may then apply the articulation command to the primary body and may co-articulate the secondary body. The system may select the primary and secondary bodies based on the current drive mode. The below table summarizes one technique for selecting the primary and secondary bodies.

TABLE 1

| Drive Mode | Primary Body | Secondary Body |
| --- | --- | --- |
| Paired Drive Mode | Outer Body | Inner Body |
| Inner Drive Mode | Inner Body | Outer Body |
| Outer Drive Mode | Outer Body | Inner Body |

The above technique for selecting the primary and secondary bodies is only one embodiment, and other techniques may be employed, for example, by selecting the inner body as the primary body and the outer body as the secondary body in the paired drive mode.

In performing co-articulation, at block 1715, the processor determines the distance between a distal end of the inner body and a distal end of the outer body. The system may be able to determine the distance between the distal ends by one of a number of different techniques, for example, based on the robot data defining the positions of the instrument manipulators. At block 1720, the processor determines a co-articulation factor based on the determined distance between the distal ends of the outer and inner bodies. In certain embodiments, the co-articulation factor may vary depending on the distance between the distal ends of the outer and inner bodies. In other embodiments, the co-articulation factor may be a static value that is applied when the distance between the distal ends of the outer and inner bodies is within a predetermined range of distances.

At block 1725, the processor articulates, via the set of instrument manipulators, the primary body based on the articulation command. That is, the system may apply the full amount of articulation received in the articulation command to the primary body. However, this disclosure is not limited thereto and the system may adjust the amount of articulation applied to the primary body in certain circumstances. At block 1730, the processor articulates, via the set of instrument manipulators, the secondary body based on the articulation command and the co-articulation factor. The co-articulation factor may define a technique for determining the amount of articulation to apply to the secondary body based on one or more of: the articulation command, the amount of articulation applied to the primary body, and the current drive mode. The method ends at block 1735.

In certain embodiments, the co-articulation factor includes a co-articulation ratio that relates an amount of articulation applied to the primary body to an amount of articulation applied to the secondary body. That is, the co-articulation ratio may define a ratio used to determine the amount of articulation to be applied to the secondary body based on the amount of articulation to be applied to the primary body. In some implementations, the co-articulation ratio is determined based on the distance between the distal ends of the outer and inner bodies. Accordingly, the amount of articulation applied to the secondary body may vary based on the distance between the distal ends. Additionally, the technique used for determining the co-articulation ratio may be dependent on the current drive mode.

Since the system maintains the distance between the distal ends of the outer and inner bodies when in paired drive mode, the co-articulation ratio may be substantially constant. However, in other embodiments, the co-articulation ratio may be adjusted in the paired drive mode based on, for example, a command received via the set of user input devices. Accordingly, in certain implementations, the user may be able to select the co-articulation ratio to adjust the amount of articulation achievable by the medical instrument. In these implementations, the user may also be able to manually select the co-articulation ratio in the other drive modes (e.g., the outer drive mode and the inner drive mode).

Figure 29A:
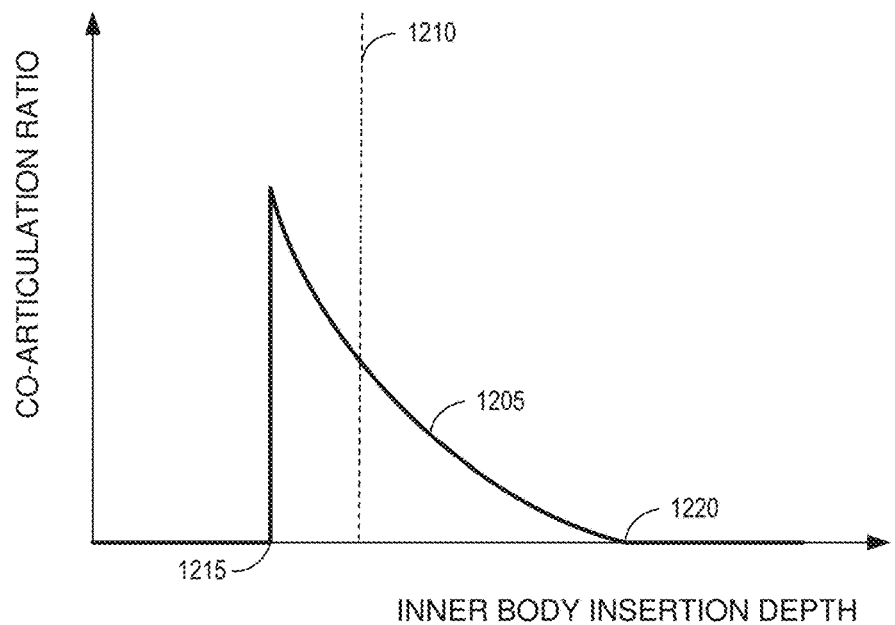
FIG. 29A includes a graph illustrating a technique for determining a co-articulation ratio in the inner body drive mode in accordance with aspects of this disclosure.

FIG. 29A includes a graph illustrating a technique for determining a co-articulation ratio in the inner body drive mode in accordance with aspects of this disclosure. In the FIG. 29A embodiment, the co-articulation ratio is illustrated by the curve or slope 1205. The inner body insertion depth (which is related to the distance between the distal ends of the outer and inner bodies) is plotted along the X-axis and the value of the co-articulation ratio is plotted along the y-axis. The graph includes a dashed line 1210 illustrating the paired position, a point 1215 representing the start of the co-articulation zone and a point 1220 representing the end of the co-articulation zone. In certain implementations, the point 1215 may be point at which the distal ends of the outer and inner bodies are aligned (e.g., no distance between the distal ends) and the point 1220 may represent an inner body insertion depth beyond which the co-articulation ratio falls to zero.

In the illustrated embodiment, co-articulation is disabled (which may involve setting the co-articulation value to zero) outside of a predetermined range of distances between the distal ends of the outer and inner bodies. The predetermined range of distances is illustrated by the inner body insertion depths between points 1215 and 1220. Outside of this range, the system may not co-articulate the secondary device, providing the articulation command only to the primary device. At the start of the co-articulation zone at point 1215, the co-articulation ratio may be set to a predetermined value. Further, the co-articulation ratio may be determined based on a predetermined function that relates the determined distance to the co-articulation ratio when the distance between the distal ends of the outer and inner bodies falls within the predetermined range of distances. As shown in FIG. 29A, the co-articulation ratio determined based on the predetermined function may decrease as the determined distance (e.g., the inner body insertion depth) increases. The curve defined by the function may be a smooth curve 1205 that defines a gradual transition from the start of the co-articulation zone 1215 to the end of the co-articulation zone 1220. In certain implementations, the predetermined function may be defined by a sigmoid function having parameters which may be selected to control the speed and shape of the curve 1205.

The system may use co-articulation factor determined based on the function defining the curve 1205 illustrated in FIG. 29A to determine an amount of articulation to be applied to the outer body (e.g. a tension to be applied to one or more tendons of the outer body) based on an articulation command received in the inner body drive mode. For example, the system may apply the full amount of the articulation command to the inner body and apply some fraction of the articulation command to the outer body, as determined using the articulation ratio.

Figure 29B:
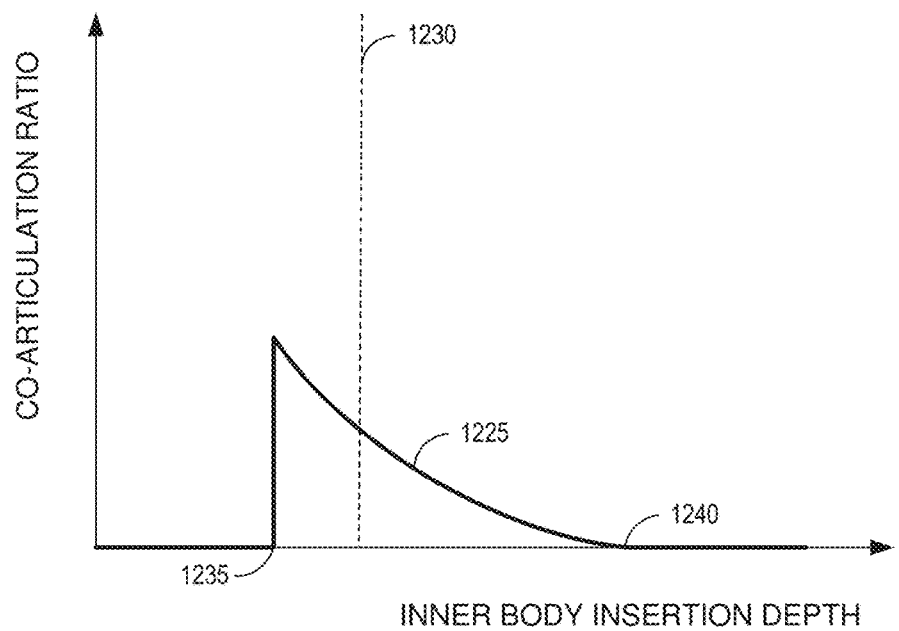
FIG. 29B includes a graph illustrating a technique for determining a co-articulation ratio in the outer body drive mode in accordance with aspects of this disclosure.

FIG. 29B includes a graph illustrating a technique for determining a co-articulation ratio in the outer body drive mode in accordance with aspects of this disclosure. In the FIG. 29A embodiment, the co-articulation ratio is illustrated by the curve or slope 1225 similar to the curve 1205 illustrated in FIG. 29A. The graph includes a dashed line 1230 illustrating the paired position, a point 1235 representing the start of the co-articulation zone and a point 1240 representing the end of the co-articulation zone. In certain implementations, the point 1235 may be point at which the distal ends of the outer and inner bodies are aligned (e.g., no distance between the distal ends) and the point 1240 may represent an inner body insertion depth beyond which the co-articulation ratio falls to zero.

The curve 1225 may be defined in a similar fashion to the curve 1205 in the inner body drive mode. However, in certain implementations, the initial value at the start of the co-articulation zone 1235 for the outer body drive mode may have a lower value than that of the inner body drive mode. Alternatively, the parameters defining the features of the curve 1225 (e.g., the speed and shape of the curve) may be adjusted in a different manner than in the inner body drive mode.

The system may use co-articulation factor determined based on the function defining the curve 1225 illustrated in FIG. 29A to determine an amount of articulation to be applied to the inner body (e.g. a tension to be applied to one or more tendons of the inner body) based on an articulation command received in the outer body drive mode. For example, the system may apply the full amount of the articulation command to the outer body and apply some fraction of the articulation command to the inner body, as determined using the articulation ratio.

The system may also be configured to use the co-articulation factor (as determined according to one of the above embodiments) based on a relaxation command to relax the medical instrument received via the set of user input devices. In certain embodiments, the system may relax, via the set of instrument manipulators of the robotic arm assemblies, the primary body based on the relaxation command, and relax, via the set of instrument manipulators of the robotic arm assemblies, the second body based on the relaxation command and the co-articulation factor. The co-articulation factor may be determined based on one or more of: the distance between the distal ends of the outer and inner bodies, the current drive mode, and the relaxation command. The relaxation command may comprise a command to relax the tension in one or more of the tendons, previously used to articulate the outer and/or inner bodies. Additionally, the outer and inner bodies may be treated as primary and secondary bodies according to table 1, similar to the co-articulation embodiments discussed above.

In certain situations, once the primary body is relaxed (e.g., no more tension is applied to the tendons in the primary body), the secondary body may still have tension in one or more of the tendons therein. Accordingly, in response to the determining that the primary body has relaxed, the system may relax, via the set of instrument manipulators of the robotic arm assemblies, the second body based on the relaxation command independent of the co-articulation factor. For example, it may not be necessary to adjust the articulation to the secondary device once the primary device is relaxed since certain issues such as muscling will no longer occur when there is no tension in the tendons of the primary body. Thus, if the system receives a relaxation command after the primary body has relaxed, the system will apply the relaxation command to the secondary body without adjusting the relaxation command based on the co-articulation ratio.

In certain implementations, the system may also be configured to receive a disable co-articulation command via the set of user input devices. The system may disable the co-articulation ratio by articulating, via the set of instrument manipulators of the robotic arm assemblies, the primary body based on the articulation command without articulating the secondary body in response to receiving the disable co-articulation command. This may provide the user additional options for manual control over each of the outer and inner bodies, which may be used to perform more complex articulation maneuvers. For example, the user may apply a certain amount of muscling between the outer and inner bodies, to provide additional support to the inner body based on the articulation of the outer body.

Figure 30:
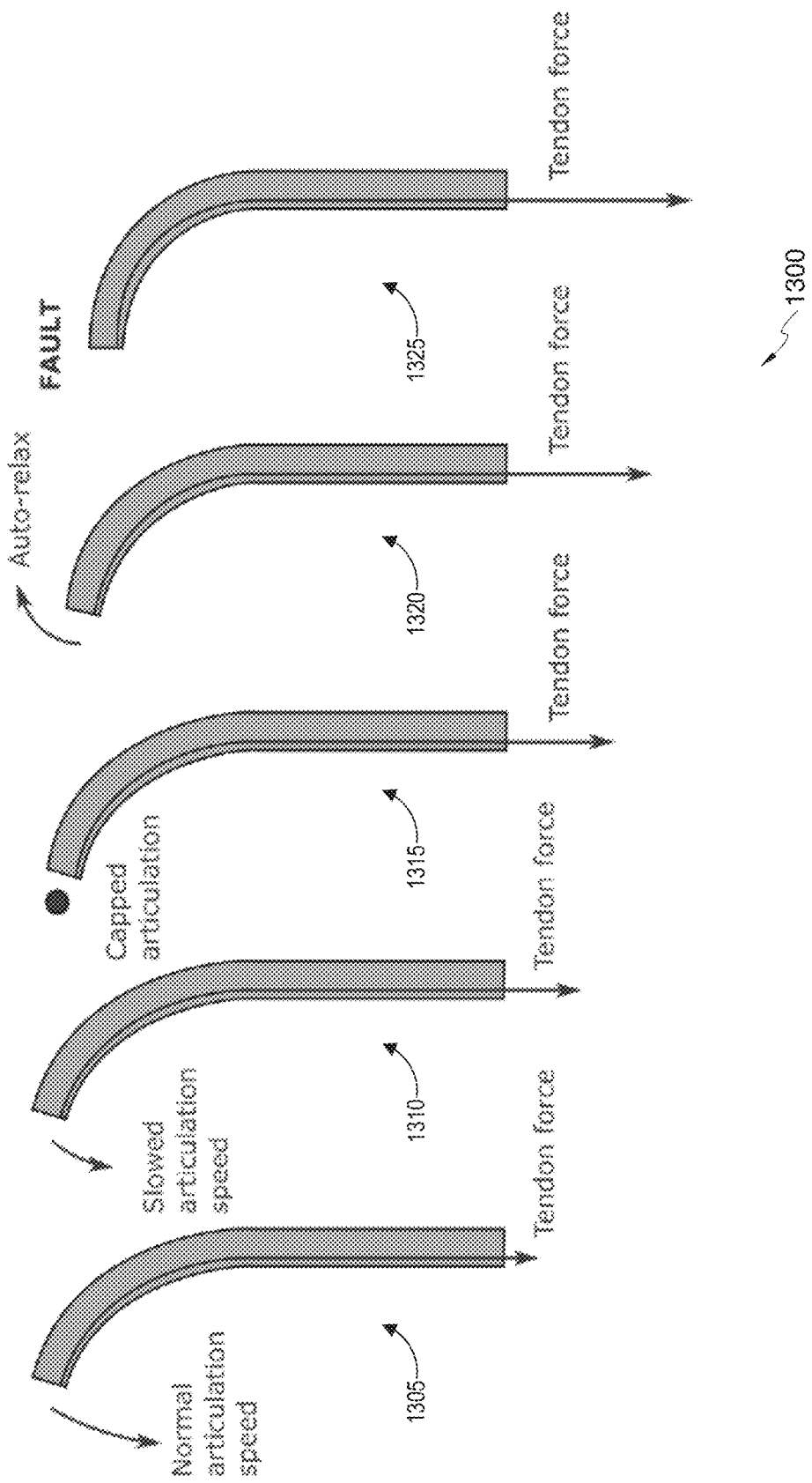
FIG. 30 illustrates an embodiment of tension monitoring for a medical instrument in accordance with aspects of this disclosure.

FIG. 30 illustrates an embodiment of tension monitoring for a medical instrument in accordance with aspects of this disclosure. In particular, FIG. 30 illustrates a number of articulation actions 1300 which may be taken by the system based on a comparison of the tension measured in one or more of the tendons of a one of the outer and inner bodies to four threshold tension values. While the tension monitoring may be applied to each of the outer and inner bodies on an individual basis, an example of tension monitoring will be described for the inner body for ease of description. A similar technique may be applied to the outer body, which may include the same or different values for the tension threshold values. In certain implementations, the system may individually monitor the tension values of each tendon in a given inner or outer body. However, in other implementations, the system may determine the norm of the tension values in each of the tendons of the corresponding inner or outer body.

In the illustrated implementation, when the measured tension in a tendon of the inner body is less than a first threshold value, the system may articulate the inner body at a normal articulation speed 1305. For example, when the tension is less than the threshold value, the system may not alter the articulation applied to the inner body. When the measured tension is greater than the first threshold value, but less than a second threshold value, the system may slow the articulation speed 1310. By slowing the articulation speed, the system may prevent the articulation of inner body from to quickly applying additional force to the lumen of the patient, thereby decreasing the chance of injury to the patient.

When the measured tension is greater than the second threshold value, but less than a third threshold value, the system may cap the amount of articulation 1315. When the amount of articulation is capped, the force applied to the patient's lumen (e.g., through additional articulation) is prevented, lowering the risk of injury. When the measured tension is greater than the third threshold value, but less than a fourth threshold value, the system may automatically relax the inner body 1320. After the articulation is capped, the tension in the tendon may increase in certain situations, such as when retracting the inner body into a portion of the lumen, or the lumen changing shape and applying a force to the tendon. The system may normally adjust the force applied to the tendons in response to external forces applied to the tendon, and thereby, increase the force to the tendon in order to maintain the current amount of articulation. By providing an auto-relax function 1320 when the tension is greater than third threshold value, the system may prevent the forces applied by the inner body to the lumen from reaching a level that may cause injury to the patient.

When the measured tension is greater than the fourth threshold value, the system may generate a fault 1325. Although the auto-relax function 1320 is meant to prevent the tension from reaching dangerous levels, the fourth threshold may be set to catch cases where the system is malfunctioning, not relaxing fast enough, or to catch any other unanticipated events. In response to the generated fault, the system may disable operation of the robotic system. Further, the system may require the medical procedure to be halted, and require the medical instrument to be removed from the patient. The system may then be reset so that the medical procedure can be restarted.

The system may further be configured to automatically deactivate the slowed articulation speed function 1310 and/or the capped articulation function 1315. In certain embodiments, in response to either of the slowed articulation speed function 1310 or the capped articulation function 1315 being activated, the system may deactivate the corresponding function 1310 or 1315 in response to the measured tension in the tendon staying below the corresponding threshold value (e.g., the first or second threshold value) for longer than a threshold period of time. The system may store a different threshold period of time for deactivating each of the slowed articulation speed function 1310 and the capped articulation function 1315.

Figure 31:
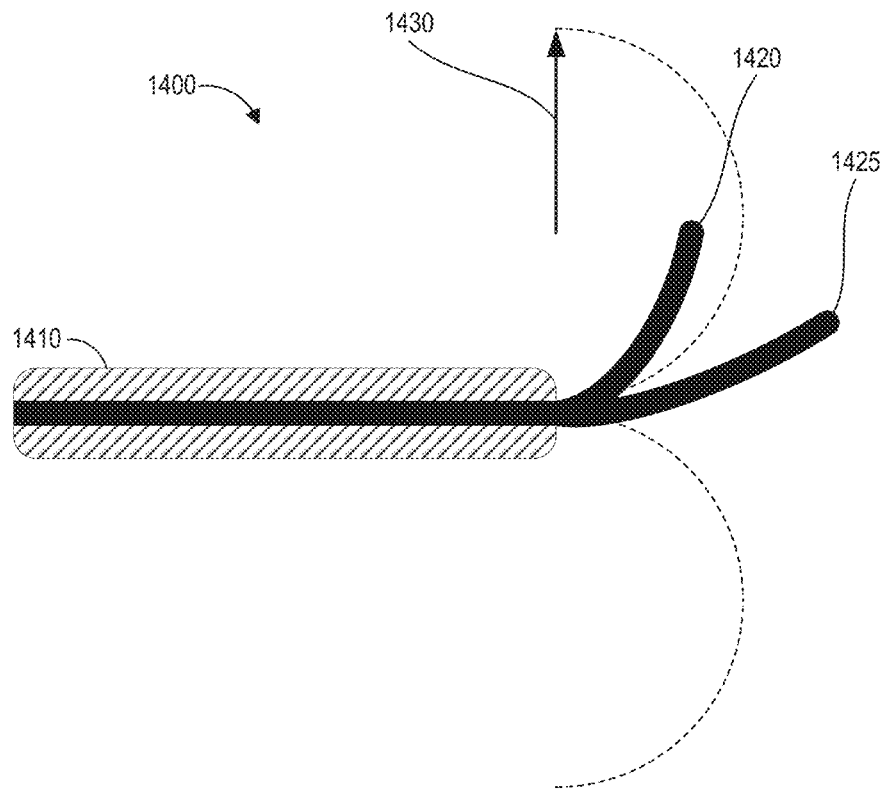
FIG. 31 illustrates an embodiment of automatic relaxation during retraction for a medical instrument in accordance with aspects of this disclosure.

FIG. 31 illustrates an embodiment of automatic relaxation during retraction for a medical instrument in accordance with aspects of this disclosure. In the embodiment of FIG. 31, the medical instrument 1400 comprises an outer body 1410 and an inner body which may be in a first position 1420 or a second position 1425. When the inner body is in the first articulation position 1420, the inner body may be articulated to have a radius of curvature that is less than a threshold radius of curvature 1430, illustrated by the dashed line. When the inner body is in the second articulation position 1425, the inner body may be articulated to have a radius of curvature that is greater than the threshold radius of curvature 1430.

One technique for automatically relaxing the medical instrument during retraction is based on the distance of retraction without receiving a user command other than retraction. For example, the system may also automatically relax the medical instrument 1400 upon retraction after the medical instrument has been retracted by greater than a threshold distance. For example, the system may determine that a distance the medical instrument has retracted is greater than a threshold distance, and in response to determining that the distance the medical instrument has retracted is greater than a threshold distance, automatically relax the medical instrument. The retraction by greater than the threshold distance may comprise a retraction of the medical instrument without receiving any insertion or articulation commands. When the system receives an articulation or insertion command, the system may prevent and/or exit the auto-relaxation command, thereby allowing the user to override the automatic relaxation. The system may preform automatic relaxation in any one of the drive modes (e.g., paired drive mode, inner body drive mode, outer body drive mode) and the determined distance of the retraction may be measured based on the primary body corresponding to the current drive mode.

Automatic relaxation based on the distance of retraction may assist the user in relaxing the medical instrument when the medical instrument is being retracted over long distance (e.g., removing the medical device after the medical procedure is complete). Generally, it is desirable to have the medical instrument relaxed when retracting over long distances, so the system may assist the user when the user forgets to manually relax the medical instrument.

Another implementation of automatic relaxation may involve a measurement of the radius of curvature of the medical instrument 1400. In response to receiving a retraction command from a set of user input device, the system may be configured to determine that a curvature of the medical instrument (e.g., the curvature of the inner body at the first position 1420 in the example of FIG. 31) is less than the threshold curvature 1430. In response to determining that curvature of the medical instrument is less than the threshold curvature 1430, the system may automatically relax the medical instrument while retracting the medical instrument. By automatically relaxing the medical instrument 1400, the system may prevent muscling of the medical instrument due to the tension in the portion of the inner body 1420 being retracted into the outer body 1410. Since muscling may lead to premature wear on the outer and/or inner bodies 1410 and 1420, this automatic relaxation may lead to a longer life for the medical instrument 1400. In certain embodiments, this implementation of automatic relaxation may occur immediately upon retraction without measuring the distance of the retraction. Alternatively, the radius of curvature auto-retraction may only occur when the articulated portion (e.g., a length of the inner body 1420 near the distal end thereof) is being retracted into the outer body 1410. The radius of curvature of the inner body 1420 may be determined based on the commanded angle (or alternatively the commanded amount of articulation) and commanded amount of insertion to the inner body 1420.

The automatic relaxation of the medical instrument may also use the co-articulation ratio for commanded relaxation as discussed above. However, in certain embodiments, during automatic relaxation, one the primary body is relaxed, the system may continue to use the co-articulation ratio in articulating the secondary body. This continued use of co-articulation may prevent the outer body from losing support for the inner body too early during automatic relaxation.

C. Outer Body Parking.

By enabling the drive mode to be selected and changed between the paired, outer body, and inner body drive modes, the system may allow for easier access to portions of the luminal network. For example, a particularly tight turn may require a small radius of curvature during articulation, which may be achieved through co-articulation in the inner body drive mode. Further, due to the diameter of the outer body, it may be necessary to park the outer body and continue advancing into the luminal network in the inner body drive mode to fit the medical instrument into a lumen having a diameter that is less than that of the outer body.

The system may have access to a pre-operative and/or intra-operative model of the luminal network through which the medical instrument is being advanced. The model may be stored in memory and may include a mapped portion of the luminal network. The memory may further store a position of a target with respect to the model and a path along the model from an access point to the target. By using the model, the position of the target, and/or the path, the system may be able to determine a position in which the sheath may be parked in order to follow the path and/or reach the target.

Figure 32:
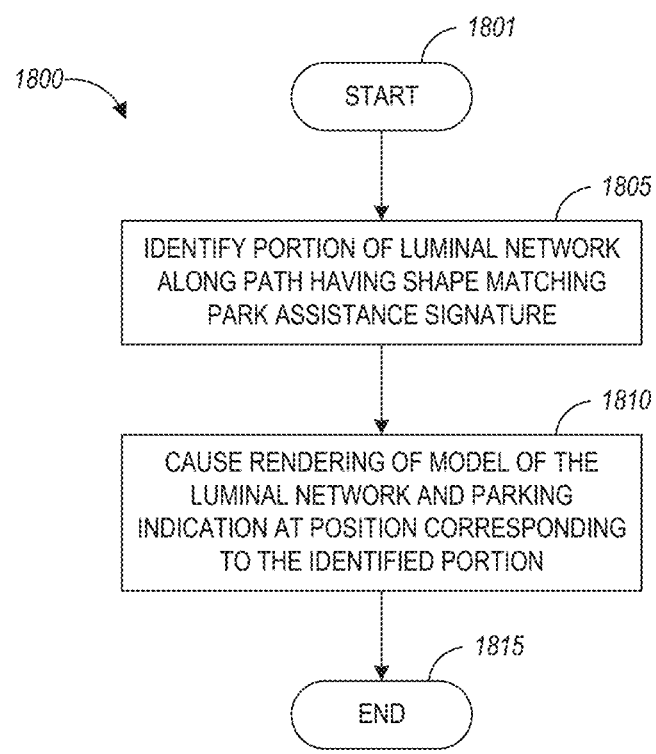
FIG. 32 is a flowchart illustrating an example method operable by a surgical robotic system, or component(s) thereof, for park assistance of a medical instrument in accordance with aspects of this disclosure.

FIG. 32 is a flowchart illustrating an example method operable by a surgical robotic system, or component(s) thereof, for park assistance of a medical instrument in accordance with aspects of this disclosure. For example, the steps of method 1800 illustrated in FIG. 32 may be performed by a processor of a surgical robotic system. For convenience, the method 1800 is described as performed by the processor of the system.

The method 1800 begins at block 1801. The processor may be included as a part of a system, including a medical instrument comprising an outer body and an inner body configured to be driven through a lumen in the outer body, a set of one or more instrument manipulators (e.g., coupled to robotic arm assemblies) configured to control movement of the outer and inner bodies, a set of one or more feedback devices, a set of one or more processors, and at least one computer-readable memory in communication with the set of processors and having stored thereon computer-executable instructions to cause the set of processors to perform the method 1800.

At block 1805, the processor identifies a portion of the luminal network along the path having a shape matching a park assistance signature. The park assistance feature may include, for example, a portion of the luminal network having a radius of curvature that is less than a threshold value, a diameter of the luminal network that is less than a threshold value, or a pre-planned location, optionally selected by the user, for parking the outer body. At block 1810, the processor causes, on at least a portion of a set of feedback devices, a parking indication at a position corresponding to the identified portion with respect to the model, the parking indication representing a place to park the distal end of the outer body. The method 1800 ends at block 1815.

Figure 33:
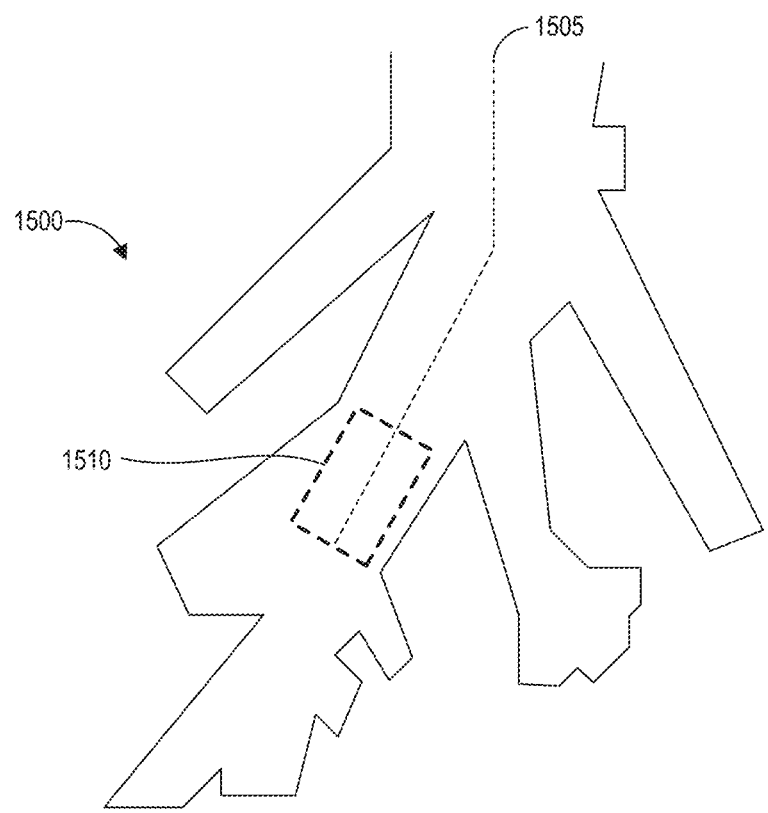
FIG. 33 illustrates an example of a parking indication in accordance with aspects of this disclosure.

FIG. 33 illustrates an example of a parking indication in accordance with aspects of this disclosure. The model 1500 illustrated in FIG. 33 may be rendered on a display and may further include a path 1505, which may be a pre-planned path to navigate the medical instrument towards a target (not illustrated), and a parking indication 1510. The parking indication may be a visual representation of a location within the model at which to park the outer body and change the drive mode to the inner body drive mode for further advancing the inner body. In other embodiments, rather than or in addition to rendering the parking indication on a display, the system may comprise a set of one or more feedback devices including at least one of: a display, a haptic feedback device, and a speaker. Accordingly, the system may provide the parking indication to the user via one or more of the above-listed feedback mechanisms. For example, the system may provide an audible and/or haptic feedback to the user when the distal end of the medical instrument is within a threshold distance of the parking indication, and provide a different type of feedback when the distal end of the medical instrument reaches the position of the parking indication.

In certain embodiments, the system may not provide a parking indication until the target is reachable in the inner body drive mode. For example, the inner body may only be able to extend from the distal end of the outer body by a threshold insertion distance. Accordingly, the system may determine that a distance from the identified portion to the target is less than the threshold insertion distance for the inner body, and in response to determining that the distance from the identified portion to the target is less than the threshold insertion distance for the inner body, cause the rendering of the parking indication. By delaying the provision of the parking indication until the distal end of the medical instrument is within the threshold insertion distance from the target, the system may prevent the user from prematurely parking the outer body at a position which would not allow the inner body to reach the target.

The system may be further configured to receive an outer body park instruction to park the outer body at a current location. The system may determine that a distance from the current location to the target is more than a threshold insertion distance for the inner body, and in response to determining that the distance from the current location to the target is more than a threshold insertion distance for the inner body cause, on at least a portion of the set of displays, a rendering of an indication that the target is not reachable by the inner body with the outer body parked at the current location. Thus, the system may be able to provide a warning to the user that parking the outer body at the current position for the remainder of the medical procedure may result in the target being unreachable. The user may be able to use that information to determine whether to continue in the paired mode without parking the outer body, or whether to use the outer body drive mode to catch the outer body up with the inner body after advancing through a portion of the luminal network.

The system may also be configured to determine the park assistance feature based on data gathered from previously performed medical procedure. For example, the park assistance signature may be determined based on previously performed medical procedures, each comprising a path having a shape matching the park assistance signature. Accordingly, the system may determine that users were more likely to park the outer body along certain paths having a shape matching the park assistance signature. The system may then be more likely to provide an indication of the parking position based on this analysis of the previously performed medical procedures. The system may also be configured to receive a selection identifying the portion of the luminal network and use the received selection in providing the parking indication.

In certain embodiments, the system may be configured to identify a location along the path at which a diameter of a lumen in the luminal network is within a threshold range of a diameter of the outer body. The system may identify the portion of the luminal network based on the identified location along the path. As such, the system may determine the parking indication based on a location within the luminal network at which the luminal network narrows to a point at which it may be difficult to further advance the outer body.

In other embodiments, the system may be further configured to detect that the medical instrument is prolapsing, and cause, on at least a portion of the set of displays, a rendering of an indication that the medical instrument is prolapsing. This feedback may be used by a user to correct the prolapsing before continuing with the procedure. One technique that may be used to detect prolapsing may include comparing the commanded advancing of the medical instrument to one or more measurements of the position of the distal end of the medical instrument (e.g., visual information from a camera in the medical instrument, position data received from an EM sensor, etc.). When the measured position data indicates that the distal end of the medical instrument has not moved in response to a command to advance the medical instrument, the system may be able to determine that the medical instrument is prolapsing. The system may also be able to provide any indication of a technique for alleviating the prolapsing depending on the severity of the prolapse. For example, a prolapse that is less than a threshold amount may be solved by advancing the outer body in the outer body drive mode, while a more sever prolapse greater than the threshold amount may require the retraction of the medical instrument.

In one embodiment, the system may be configured to detect prolapsing in response to receiving an inner body advancement instruction to advance the inner body. The system may instruct the set of instrument manipulators of the robotic arm assemblies to advance the inner body and in response instructing the set of instrument manipulators of the robotic arm assemblies to advance the inner body, determine that the position of the distal end of the inner body has not moved based on output from the one or more sensors. The system may detect that the medical instrument is prolapsing based on determining that the position of the distal end of the inner body has not moved.

3. Implementing Systems and Terminology.

Implementations disclosed herein provide systems, methods and apparatuses for driving a medical instrument having an inner body and an outer body.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The functions for driving a medical instrument described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A robotic surgical system, comprising:
a medical instrument comprising an outer body and an inner body configured to be driven through a lumen in the outer body;
a set of one or more instrument manipulators configured to control movement of the outer and inner bodies;
a set of one or more user input devices;
a set of one or more processors; and
at least one computer-readable memory in communication with the set of one or more processors and having stored thereon computer-executable instructions to cause the set of one or more processors to:
receive, via the set of one or more user input devices, an articulation command to articulate the medical instrument;
select one of the outer and inner bodies as a primary body and another of the outer and inner bodies as a secondary body;
determine a distance between a distal end of the inner body and a distal end of the outer body;
determine a co-articulation factor based on the distance;
articulate, via the set of one or more instrument manipulators, the primary body based on the articulation command; and
articulate, via the set of one or more instrument manipulators, the secondary body based on the articulation command and the co-articulation factor.

2. The robotic surgical system of claim 1, wherein the computer-executable instructions are further configured to cause the set of one or more processors to:
receive, via the set of one or more user input devices, a drive mode command for driving the medical instrument in one of a plurality of drive modes, and
control movement of the primary and secondary bodies based on the drive mode command.

3. The robotic surgical system of claim 1, wherein the co-articulation factor comprises a co-articulation ratio relating an amount of articulation applied to the primary body to an amount of articulation applied to the secondary body.

4. The robotic surgical system of claim 3, wherein the computer-executable instructions are further configured to cause the set of one or more processors to:
determine that the distance between the distal end of the inner body and the distal end of the outer body falls outside of a predetermined range of distances; and
in response to determining that the distance falls outside of the predetermined range of distances, disable the articulation of the secondary body.

5. The robotic surgical system of claim 3, wherein the computer-executable instructions are further configured to cause the set of one or more processors to:
determine that the distance between the distal end of the inner body and the distal end of the outer body falls within a predetermined range of distances; and
in response to determining the distance falls within the predetermined range of distances, determine the co-articulation ratio based on a predetermined function relating the distance to the co-articulation ratio,
wherein the predetermined function causes the co-articulation ratio to decrease as the distance increases.

6. The robotic surgical system of claim 5, wherein the predetermined function comprises a first function used in response to the primary body being the inner body and a second function used in response to the primary body being the outer body.

7. The robotic surgical system of claim 1, wherein the computer-executable instructions are further configured to cause the set of one or more processors to:
receive, via the set of one or more user input devices, a relaxation command to relax the medical instrument;
cause the set of one or more instrument manipulators to relax the primary body based on the relaxation command; and
cause the set of one or more instrument manipulators to relax the secondary body based on the relaxation command and the co-articulation factor.

8. The robotic surgical system of claim 7, wherein the computer-executable instructions are further configured to cause the set of one or more processors to:
determine that the primary body has relaxed; and
in response to determining that the primary body has relaxed, cause the set of one or more instrument manipulators to relax the secondary body based on the relaxation command independent of the co-articulation factor.

9. The robotic surgical system of claim 1, wherein the computer-executable instructions are further configured to cause the set of one or more processors to:
receive, via the set of one or more user input devices, a disable co-articulation command; and
in response to receiving the disable co-articulation command, cause the set of one or more instrument manipulators to articulate the primary body without articulating the secondary body.

10. The robotic surgical system of claim 1, wherein:
each of the outer and inner bodies comprises:
a set of one or more tendons configured to articulate a corresponding one of the outer or inner body, and
a set of one or more tension monitors configured to monitor tension in a corresponding one or more of the set of one or more tendons, and
the computer-executable instructions are further configured to cause the set of one or more processors to:
measure the tension in one of the set of one or more tendons of at least one of the outer or inner bodies based on an output received from a corresponding tension monitor;
compare the measured tension to one or more threshold values; and
modify articulation applied to the at least one of the outer or inner bodies in response to the measured tension being greater than at least one of the one or more threshold values.

11. The robotic surgical system of claim 10, wherein:
the one or more threshold values comprise a first threshold value, a second threshold value, a third threshold value, and a fourth threshold value, and
the computer-executable instructions are further configured to cause the set of one or more processors to:
slow a speed of articulation in response to the measured tension being greater than the first threshold value;
limit articulation to a maximum articulation value in response to the measured tension being greater than the second threshold value;
relax the at least one of the outer or inner bodies in response to the measured tension being greater than the third threshold value; and
generate a fault condition in response to the measured tension being greater than the fourth threshold value.

12. The robotic surgical system of claim 1, wherein the computer-executable instructions are further configured to cause the set of one or more processors to:
receive, via the set of one or more user input devices, a retraction command to retract the medical instrument;
in response to receiving the retraction command, cause the set of one or more instrument manipulators to retract the medical instrument;
determine that a distance the medical instrument has retracted is greater than a threshold distance; and
in response to determining the distance the medical instrument has retracted is greater than the threshold distance, cause the set of one or more instrument manipulators to relax the medical instrument.

13. The robotic surgical system of claim 1, wherein the computer-executable instructions are further configured to cause the set of one or more processors to:
receive, via the set of one or more user input devices, a retraction command to retract the medical instrument;
determine that a radius of curvature of the medical instrument is less than a threshold radius of curvature; and
in response to determining the curvature of the medical instrument is less than the threshold radius of curvature, cause the set of one or more instrument manipulators to relax the medical instrument.

14. The robotic surgical system of claim 1, wherein the computer-executable instructions are further configured to cause the set of one or more processors to:
receive, via the set of one or more user input devices, an indication of a user of the robotic surgical system; and
determine the co-articulation factor based on the indication of the user.

15. A method of navigating a medical instrument comprising an outer body and an inner body configured to be driven through a lumen in the outer body, the method comprising:
receiving, via a set of one or more user input devices, an articulation command to articulate the medical instrument;
selecting one of the outer and inner bodies as a primary body and another of the outer and inner bodies as a secondary body;
determining a distance between a distal end of the inner body and a distal end of the outer body;
determining a co-articulation factor based on the distance;
articulating, via a set of one or more instrument manipulators, the primary body based on the articulation command; and
articulating, via the set of one or more instrument manipulators, the secondary body based on the articulation command and the co-articulation factor.

16. The method of claim 15, further comprising:
receiving, via the set of one or more user input devices, a drive mode command for driving the medical instrument in one of a plurality of drive modes; and
controlling movement of the primary and secondary bodies based on the drive mode command.

17. The method of claim 15, wherein the co-articulation factor comprises a co-articulation ratio relating an amount of articulation applied to the primary body to an amount of articulation applied to the secondary body.

18. The method of claim 17, further comprising:
determining that the distance between the distal end of the inner body and the distal end of the outer body falls outside of a predetermined range of distances; and
in response to determining that the distance falls outside of the predetermined range of distances, disabling the articulation of the secondary body.

19. The method of claim 18, further comprising:
determining that the distance between the distal end of the inner body and the distal end of the outer body falls within the predetermined range of distances; and
in response to determining the distance falls within the predetermined range of distances, determining the co-articulation ratio based on a predetermined function relating the distance to the co-articulation ratio,
wherein the predetermined function causes the co-articulation ratio to decrease as the distance increases.

20. The method of claim 19, wherein the predetermined function comprises a first function used in response to the primary body being the inner body and a second function used in response to the primary body being the outer body.

21. The method of claim 15, further comprising:
receiving, via the set of one or more user input devices, a relaxation command to relax the medical instrument;
cause the set of one or more instrument manipulators to relax the primary body based on the relaxation command; and
cause the set of one or more instrument manipulators to relax the secondary body based on the relaxation command and the co-articulation factor.

22. The method of claim 21, further comprising:
determining that the primary body has relaxed; and
in response to determining that the primary body has relaxed, cause the set of one or more instrument manipulators to relax the secondary body based on the relaxation command independent of the co-articulation factor.

23. The method of claim 15, further comprising:
receiving, via the set of one or more user input devices, a disable co-articulation command; and
in response to receiving the disable co-articulation command, cause the set of one or more instrument manipulators to articulate the primary body without articulating the secondary body.

24. The method of claim 15, wherein:
each of the outer and inner bodies comprises:
a set of one or more tendons configured to articulate a corresponding one of the outer or inner body, and
a set of one or more tension monitors configured to monitor tension in a corresponding one or more of the set of one or more tendons, and the method further comprises:
- measuring the tension in one of the set of one or more tendons of at least one of the outer or inner bodies based on an output received from a corresponding tension monitor;
- comparing the measured tension to one or more threshold values; and
- modifying articulation applied to the at least one of the outer or inner bodies in response to the measured tension being greater than at least one of the one or more threshold values.

25. The method of claim 24, wherein:

the one or more threshold values comprise a first threshold value, a second threshold value, a third threshold value, and a fourth threshold value, and the method further comprises:
- slowing a speed of articulation in response to the measured tension being greater than the first threshold value;
- limiting articulation to a maximum articulation value in response to the measured tension being greater than the second threshold value;
- relaxing the at least one of the outer or inner bodies in response to the measured tension being greater than the third threshold value; and
- generating a fault condition in response to the measured tension being greater than the fourth threshold value.

26. A non-transitory computer readable storage medium having stored thereon instructions that, when executed, cause at least one computing device to:
- receive, via a set of one or more user input devices, an articulation command to articulate a medical instrument, the medical instrument comprising an outer body and an inner body configured to be driven through a lumen in the outer body;
- select one of the outer and inner bodies as a primary body and another of the outer and inner bodies as a secondary body;
- determine a distance between a distal end of the inner body and a distal end of the outer body;
- determine a co-articulation factor based on the distance;
- articulate, via a set of one or more instrument manipulators, the primary body based on the articulation command; and
- articulate, via the set of one or more instrument manipulators, the secondary body based on the articulation command and the co-articulation factor.

27. The non-transitory computer readable storage medium of claim 26, wherein the instructions, when executed, further cause the at least one computing device to:
- receive, via the set of one or more user input devices, a drive mode command for driving the medical instrument in one of a plurality of drive modes; and
- control movement of the primary and secondary bodies based on the drive mode command.

28. The non-transitory computer readable storage medium of claim 26, wherein the co-articulation factor comprises a co-articulation ratio relating an amount of articulation applied to the primary body to an amount of articulation applied to the secondary body.

29. The non-transitory computer readable storage medium of claim 26, wherein the instructions, when executed, further cause the at least one computing device to:
- determine that the distance between the distal end of the inner body and the distal end of the outer body falls outside of a predetermined range of distances; and
- in response to determining that the distance falls outside of the predetermined range of distances, disable articulation of the secondary body.

30. The non-transitory computer readable storage medium of claim 28, wherein the instructions, when executed, further cause the at least one computing device to:
- determine that the distance between the distal end of the inner body and the distal end of the outer body falls within a predetermined range of distances; and
- in response to determining the distance falls within the predetermined range of distances, determine the co-articulation ratio based on a predetermined function relating the distance to the co-articulation ratio,
- wherein the predetermined function causes the co-articulation ratio to decrease as the distance increases.

* * * * *